US009403880B2

(12) United States Patent
Eloit et al.

(10) Patent No.: US 9,403,880 B2
(45) Date of Patent: Aug. 2, 2016

(54) IDENTIFICATION OF A HUMAN GYROVIRUS AND APPLICATIONS

(75) Inventors: Marc Eloit, Paris (FR); Justine Cheval, Paris (FR); Virginie Sauvage, Reims (FR)

(73) Assignees: INSTITUT PASTEUR, Paris (FR); ECOLE NATIONALE VETERINAIRE D'ALFORT, Maison Alfort (FR); PATHOQUEST, Paris (FR)

( * ) Notice: Subject to any disclaimer, the term of this patent is extended or adjusted under 35 U.S.C. 154(b) by 297 days.

(21) Appl. No.: 13/989,628

(22) PCT Filed: Nov. 25, 2011

(86) PCT No.: PCT/EP2011/071086

§ 371 (c)(1), (2), (4) Date: Sep. 12, 2013

(87) PCT Pub. No.: WO2012/069657

PCT Pub. Date: May 31, 2012

(65) Prior Publication Data

US 2013/0345400 A1 Dec. 26, 2013

Related U.S. Application Data

(60) Provisional application No. 61/449,930, filed on Mar. 7, 2011.

(30) Foreign Application Priority Data

Nov. 26, 2010 (EP) .................................... 10306307

(51) Int. Cl.

| | |
|---|---|
| ***C07K 14/005*** | (2006.01) |
| ***C12N 7/00*** | (2006.01) |
| *C07K 19/00* | (2006.01) |
| *A61K 38/00* | (2006.01) |
| *A61K 39/00* | (2006.01) |

(52) U.S. Cl.

CPC ................ *C07K 14/005* (2013.01); *C12N 7/00* (2013.01); *A61K 38/00* (2013.01); *A61K 39/00* (2013.01); *C12N 2750/10021* (2013.01); *C12N 2750/10022* (2013.01)

(58) Field of Classification Search

CPC ........... C07K 14/005; A61K 2039/525; C12N 2740/16222; Y10S 977/916

See application file for complete search history.

(56) References Cited

FOREIGN PATENT DOCUMENTS

WO 96/01116 1/1996

OTHER PUBLICATIONS

Sun, Jun, et al., Int. J. Cancer. vol. 124, pp. 2973-2081 (2009).
Los, Marek, et al., Biochimica et Biophysica Acta, vol. 1793, pp, 1335-1342 (2009).
EMBL Database Entry FR823283.
Sauvage, Virginia, et al., J. Virol., vol. 85, No. 15, pp. 7948-7950 (2011).

*Primary Examiner* — Bao Li
(74) *Attorney, Agent, or Firm* — Law Office of Salvatore Arrigo and Scott Lee, LLP

(57) ABSTRACT

The present invention relates to HGyV, a human gyrovirus related to the chicken anemia virus (CAV). The present invention also relates to a new proteins encoded by HGyV, which proteins display some homology to CAV proteins. Among these new proteins, H-apoptin is of particular interest as it is herein found for the first time in a human virus and can be used for treating cancer. Also provided are methods for detecting the HGyV virus in a subject.

14 Claims, 9 Drawing Sheets

Figure 1:
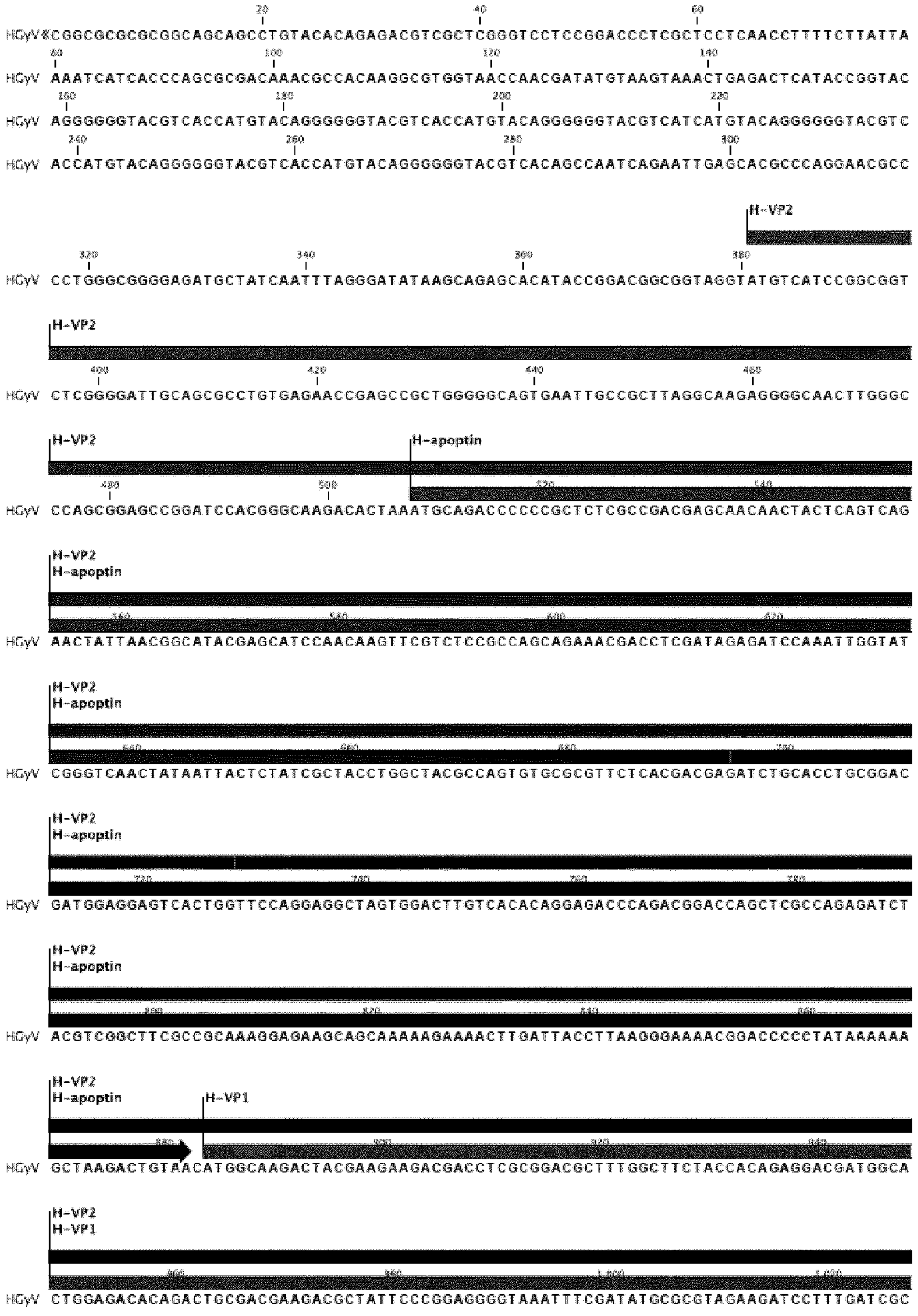
Figure 1:
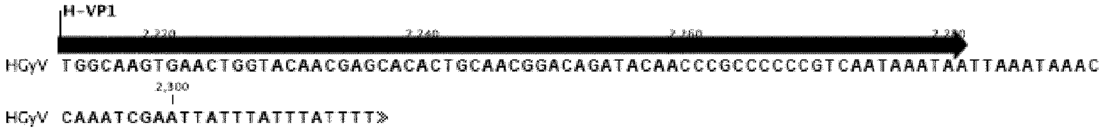

H-VP2
H-VP1
1,040 1,060 1,080 1,100
HGyV CGCGTTAAGAGGAGGATCTTCAACCCACACCCGGGCTCCTATGTGGTAAGGCTACCGAACCCTTACAATAAGCTTACCC

H-VP1
1,120 1,140 1,160 1,180
HGyV TCTTTTTCCAAGGCATTGTATTCATTCCGGAGGCTCAAGCTTTTGTTAAAAGCACCTATAAAAAGACTAACCTTACGGT

H-VP1
1,200 1,220 1,240 1,260
HGyV TTGCCATGTAGCCTCCATAAATGTTAACCTCCGAGAATTTATGCTTGCAACAATGCCTTTAGATGCAAAGAGCAAAATC

H-VP1
1,280 1,300 1,320 1,340
HGyV GGAGGCCCTAACCCTTATCCTCAGCACTTGCAGGGGTGCCAATGGTCAGCACAAACGACGCAGGACGCATGGCCGTACG

H-VP1
1,360 1,380 1,400 1,420
HGyV CAGCGGGCATGTCAGAAACAAAAAGACCCAGCGTACCACCGAGTGAGTGGTGGCGCTGGGCTCTCCTGGTGATGCACCC

H-VP1
1,440 1,460 1,480 1,500
HGyV TAGAGCACCTGGCAGATTTTACAATGCCCCAAAGCTAATGACTCTGGACGCTATGGGAGACCTGTTAGGGGGCTGGCAG

H-VP1
1,520 1,540 1,560 1,580
HGyV CTATTCAGGCATGTAAAAACCAAGTTCAGAGTGCTAGCGACTATGGGACAAGGGGCTTTCTCACCAGTTGCAAGCCTAC

H-VP1
1,600 1,620 1,640
HGyV TTGTACAAAATGACTACTGGAGCAGGAGGCACTTAGAGGGCTTCCCAGTTAAAGGTGCACCACCTATGTGCACCATGCA

H-VP1
1,660 1,680 1,700 1,720
HGyV AAGAAAAACTCAGCAGTACGGCAACGTGGAGTCCAATGCACCGGCAGATGAGCAATGGCTACCCGTAAATCCCCCAGAC

H-VP1
1,740 1,760 1,780 1,800
HGyV CCACCAGTGTACCCAAACCAGGGAGGATGCTCCCAAAACGTGGCTCCAGGCATATACCGGCTTGCAGGCTTAGAAGACA

H-VP1
1,820 1,840 1,860 1,880
HGyV GCAGCAGATGCTTTTATTCAAAGGCTTGTTTCCCCAGCTTTGCAGCGCTTTCTGCTATGGGTGCACCCTGGTCATTTCC

H-VP1
1,900 1,920 1,940 1,960
HGyV TAGCACTCAAAAACCTATTCAAAGAGGCTCATTTAACAAGCACTCCATCACGGGGACAGGGGACCCCCAGGGCCGACGG

H-VP1
1,980 2,000 2,020 2,040
HGyV TGGTTAACACTTGTGCCTAAAGGAGTCGAGTGGATTACTGACGACACCATGGAACCTACGCAACTGGACACAGACATTG

H-VP1
2,060 2,080 2,100 2,120
HGyV CAACACTCTTCTTGGCTCAAGGCAGTCCAGTATGGGCACCCTACAAATTCGGAACTTTTCACAAAGCGATGGCGCTAAC

H-VP1
2,140 2,160 2,180 2,200
HGyV AGCGATGCAGACCACCCCTTGGTGCGTGGTGAAAGTCCGTTCCATCTGGCAGCTCGGCAACCAAAGACAGCCGTACCCA

Figure 1 (continued)

```
                         20                    40
                          |                     |
     HGyV«CGGCGC-GCG CGGCAGC--- ---------- ----AGCCTG 22
   M55918«GAATTCCGAG TGGTTACTAT TCCATCACCA TTCTAGCCTG 40
Consensus NNNNNCCGNG NGGNNNCTAT TCCATCACCA TTCTAGCCTG
                         60                    80
                          |                     |
     HGyV TACACAGAGA CGTCGCTCGG GTCCTCCGGA CCCTCGCTCC 62
   M55918 TACACAGAAA G-----TCAA GATGGACGAA TCGCTCGACT 75
Consensus TACACAGANA NGTCGCTCNN GNNNNNCGNA NCNNNNNNCN
                        100                   120
                          |                     |
     HGyV TCAACCTTTT CTTATTAAAA TCATCACCCA GCGCGACAAA 102
   M55918 TCGCTCGCGA TTCGTCGAAG GCG------- GGGGGCCGGA 108
Consensus TCNNNCNNNN NTNNTNNAAN NCNTCACCCA GNGNGNCNNA
                        140                   160
                          |                     |
     HGyV CGCCACAAGG CGTGGTAACC AACGATATGT AAGTAAACTG 142
   M55918 GGCCCCC--- --CGGTGGCC CCCCTCCAAC GAGTGGA--- 140
Consensus NGCCNCNAGG CGNGGTNNCC NNCNNNNNNN NAGTNNACTG
                        180                   200
                          |                     |
     HGyV AGACTCATAC CGGTACAGGG GGGTACGTCA CCATGTACAG 182
   M55918 --------GC ACGTACAGGG GGGTACGTCA TC-CGTACAG 171
Consensus AGACTCATNC NNGTACAGGG GGGTACGTCA NCANGTACAG
                        220                   240
                          |                     |
     HGyV GGGGGTACGT CACCATGTAC AGGGGGGTAC GTCATCATGT 222
   M55918 GGGGGTACGT CATC-CGTAC AGGGGGGTAC GTCA------ 204
Consensus GGGGGTACGT CANCANGTAC AGGGGGGTAC GTCATCATGT
                        260                   280
                          |                     |
     HGyV ACAGGGGGGT ACGTCACCAT GTACAGGGGG GTACGTCACC 262
   M55918 -CAAAGAGGC GTTCC----C GTACAGGGGG GTACGTCAC- 238
Consensus ACANNGNGGN NNNNCACCAN GTACAGGGGG GTACGTCACC
                        300                   320
                          |                     |
     HGyV ATGTACAGGG GGGTACGTCA CAGCCAATCA GAATTGAGCA 302
   M55918 GCGTACAGGG GGGTACGTCA CAGCCAATCA AAAGCTGCCA 278
Consensus NNGTACAGGG GGGTACGTCA CAGCCAATCA NAANNNNNCA
                        340                   360
                          |                     |
     HGyV CGCC-CAGGA ACGCCCCTGG GCGGGGAGAT GCTATCAATT 341
   M55918 CGTTGCGAAA GTGACGTTTC GAAAATGGGC GGCGCAAGCC 318
Consensus CGNNGCNNNA NNGNCNNTNN GNNNNNNGNN GNNNNNANNN
                        380                   400
                          |                     |
     HGyV TAGGGATATA AGCAGAGCAC ATACCGGACG GCGGTAGGTA 381
   M55918 TCTCTATATA TTGAGCGCAC ATACCGGTCG GCAGTAGGTA 358
Consensus TNNNNATATA NNNAGNGCAC ATACCGGNCG GCNGTAGGTA
                        420                   440
                          |                     |
     HGyV TGTCATCCGG CGGTCTCGGG GATTGCA--G CGCCTGTGAG 419
   M55918 TA-CGCAAGG CGGTCCGGGT GGATGCACGG GAACGGCGGA 397
Consensus TNTCNNNNGG CGGTCNNGGN GNNTGCACGG NNNCNGNGNN
                        460                   480
                          |                     |
     HGyV AACCGAGCCG CTGGGGGCAG TGAATTGCCG CTTAGGCAAG 459
   M55918 CAACCGGCCG CTGGGGGCAG TGAATCGGCG CTTAGCCGAG 437
Consensus NANCNNGCCG CTGGGGGCAG TGAATNGNCG CTTAGNCNAG
                        500                   520
                          |                     |
     HGyV AGGGGCAACT TGGGCCCAGC GGAGCCGGAT CCACGGGCAA 499
   M55918 AGGGGCAACC TGGGCCCAGC GGAGCCGCG- -CAGGGGCAA 475
Consensus AGGGGCAACN TGGGCCCAGC GGAGCCGNNT CCANGGGCAA
                        540                   560
                          |                     |
     HGyV GACACTAAAT GCAGACCCCC CGCTCTCGCC GACGAGCAAC 539
   M55918 GTAATTTCAA ATGAAC---- -GCTCTCCAA GAAGA----- 505
Consensus GNNANTNNAN NNNNACCCCC CGCTCTCNNN GANGAGCAAC
                        580                   600
                          |                     |
     HGyV AACTACTCAG TCAGAACTAT TAACGGCATA CGAGCATCCA 579
   M55918 ---TACTCCA CCCGGACCAT CAACGGTGTT CAGGCCACCA 542
Consensus AACTACTCNN NCNGNACNAT NAACGGNNTN CNNGCNNCCA
                        620                   640
                          |                     |
     HGyV ACAAGTTCGT CTCCGCCAGC AGAAACGACC TCGATAGAGA 619
   M55918 ACAAGTTCAC GGCCGTTGGA AACCCCTCAC TGCAGAGAGA 582
Consensus ACAAGTTCNN NNCCGNNNGN ANNNNCNNNC TNNANAGAGA
                        660                   680
                          |                     |
     HGyV TCCAAATTGG TATCGGGTCA ACTATAATTA CTCTATCGCT 659
   M55918 TCCGGATTGG TATCGCTGGA ATTACAATCA CTCTATCGCT 622
Consensus TCCNNATTGG TATCGNNNNA ANTANAATNA CTCTATCGCT
```

Figure 2

```
                                         700                            720
     HGyV ACCTGGCTAC GCCAGTGTGC GCGTTCTCAC GACGAGATCT 699
   M55918 GTGTGGCTGC GCGAATGCTC GCGCTCCCAC GCTAAGATCT 662
Consensus NNNTGGCTNC GCNANTGNNC GCGNTCNCAC GNNNAGATCT
                                         740                            760
     HGyV GCACCTGCGG ACGATGGAGG AGTCACTGGT TCCAGGAGGC 739
   M55918 GCAACTGCGG ACAATTCAGA AAGCACTGGT TTCAAGAATG 702
Consensus GCANCTGCGG ACNATNNAGN ANNCACTGGT TNCANGANNN
                                         780                            800
     HGyV TAGTGGACTT GTCACACAGG AGACCCAGAC GGACCAGCTC 779
   M55918 TGCCGGACTT GAGGACCGAT CAACCCAAGC ---CTCCCTC 739
Consensus TNNNGGACTT GNNNNNCNNN NNACCCANNC GGACNNNCTC
                                         820                            840
     HGyV GCCAGAGATC TACGTCGGCT TCGCCG--CA AAGGAGAAGC 817
   M55918 GAAGAAGCGA TCCTGCGACC CCTCCGAGTA CAGGGTAAGC 779
Consensus GNNNNAGNNN TNCNNCGNCN NCNCCGAGNA NAGGNNAAGC
                                         860                            880
     HGyV -AGCAAAAAG AAAACTTGAT TACCTTAAGG GAAAACGGAC 856
   M55918 GAGCTAAAAG AAAGCTTGAT TACCACTACT CCCAGCCGAC 819
Consensus GAGCNAAAAG AAANCTTGAT TACCNNNANN NNNANCNGAC
                                         900                            920
     HGyV CCC---CTAT AAAAAAGC-- -TAAGACTGT AACATGGCAA 890
   M55918 CCCGAACCGC AAAAAGGCGT ATAAGACTGT AAGATGGCAA 859
Consensus CCCGAACNNN AAAAANGCGT ATAAGACTGT AANATGGCAA
                                         940                            960
     HGyV GACTACGAAG AAGACGACCT CGCGGACGCT TTGGCTTCTA 930
   M55918 GAC---GAGC TCGCAGACCG AGAGGCCGAT TTTACTCCTT 896
Consensus GACTACGANN NNGNNGACCN NGNGGNCGNT TTNNCTNCTN
                                         980                          1,000
     HGyV CCACAGAGGA CGATGGCACT GGAGACACAG ACTGCGACGA 970
   M55918 CAGAAGAGGA CGGTGGCACC ACCTCAAGCG ACTTCGACGA 936
Consensus CNNNAGAGGA CGNTGGCACN NNNNNNANNG ACTNCGACGA
                                       1,020                          1,040
     HGyV AGACGCTATT CCCGGAGGGG TAAATTTCGA TATGCGCGTA 1010
   M55918 AGATA----- ---------- TAAATTTCGA CATCGGAGGA 961
Consensus AGANNCTATT CCCGGAGGGG TAAATTTCGA NATNNGNGNA
                                       1,060                          1,080
     HGyV GAAGATCCTT TGATCGCCGC GTTAAGAGGA GGATCTT--- 1047
   M55918 GACAGCGGTA TCGTAGACGA GCTTTTAGGA AGGCCTTTCA 1001
Consensus GANNNNNNTN TNNTNGNCGN GNTNNNAGGA NGNNCTTTCA
                                       1,100                          1,120
     HGyV CAACCCACAC CCGGGCTCCT ATGTGGTAAG GCTACCGAAC 1087
   M55918 CAACCCCCGC CCCGGTACGT ATAGTGTGAG GCTGCCGAAC 1041
Consensus CAACCCNCNC CCNGGNNCNT ATNNNGTNAG GCTNCCGAAC
                                       1,140                          1,160
     HGyV CCTTACAATA AGCTTACCCT CTTTTTCCAA GGCATTGTAT 1127
   M55918 CCCCAATCTA CTATGACTAT CCGCTTCCAA GGGGTCATCT 1081
Consensus CCNNANNNTA NNNTNACNNT CNNNTTCCAA GGNNTNNTNT
                                       1,180                          1,200
     HGyV TCATTCCGGA GGCTCAAGCT TTTGTTAAAA GCACCTA--- 1164
   M55918 TTCTCACGGA AGGACTCATT CTGCCTAAAA ACAGCACAGC 1121
Consensus TNNTNNCGGA NGNNCNNNNT NTNNNTAAAA NCANCNNAGC
                                       1,220                          1,240
     HGyV -------TAA AAAGACTAAC CTTACGGTTT GCCATGTAGC 1197
   M55918 GGGGGGCTAT GCAGACCACA TGTACGGGGC GAGA-GTCGC 1160
Consensus GGGGGGCTAN NNAGACNANN NNTACGGNNN GNNATGTNGC
                                       1,260                          1,280
     HGyV CTCCATAAAT GTTAACCTCC GAGAATTTAT GCTTGCAACA 1237
   M55918 CAAGATCTCT GTGAACCTGA AAGAGTTCCT GCTAGCCTCA 1200
Consensus CNNNATNNNT GTNAACCTNN NAGANTTNNT GCTNGCNNCA
                                       1,300                          1,320
     HGyV ATGCCTTTAG ATGCAAAGAG CAAAATCGGA GGCCCTAACC 1277
   M55918 ATGAACCTGA CATACGTGAG CAAAATCGGA GGCCCCATCG 1240
Consensus ATGNNNNTNN NNNNNNNGAG CAAAATCGGA GGCCCNANCN
                                       1,340                          1,360
     HGyV CTTATCCTCA GCACTTGCAG GGGTGCCAAT GGTCAGCACA 1317
   M55918 CCGGTGAGTT GATTGCGGAC GGGTCTAAAT ------CACA 1274
Consensus CNNNTNNNNN GNNNNNGNAN GGGTNNNAAT GGTCAGCACA
```

Figure 2 continued

```
                                              1,380                      1,400
                                                |                          |
     HGyV  AACGACGCAG  GAC--GCATG  GCCGTACGCA  GCGGGCATGT  1355
   M55918  AGCCGCGGAC  AATTGGCCTA  ATTGCTGGCT  GC-----CGC  1309
Consensus  ANCNNCGNAN  NANTGGCNTN  NNNGNNNGCN  GCGGGCANGN
                                              1,420                      1,440
                                                |                          |
     HGyV  CAGAAACAAA  AAGACCCAGC  GTACCACCGA  GTGAGTGGTG  1395
   M55918  TAGATAATAA  CGTGCCCTCC  GCTACACCAT  CGGCATGGTG  1349
Consensus  NAGANANNAA  NNNNCCCNNC  GNNNCACCNN  NNGNNTGGTG
                                              1,460                      1,480
                                                |                          |
     HGyV  GCGCTGGGCT  CTCCTGGTGA  TGCACCCTAG  AGCACCTGGC  1435
   M55918  GAGATGGGCC  TTAATGATGA  TGCAGCCCAC  GGACTCTTGC  1389
Consensus  GNGNTGGGCN  NTNNTGNTGA  TGCANCCNAN  NGNNNCTNGC
                                              1,500                      1,520
                                                |                          |
     HGyV  AGATTTTACA  ATGCCCCAAA  GCTAATGACT  CTGGACGCTA  1475
   M55918  CGGTTCTTTA  ATCACCCAAA  GCAGATGACC  CTGCAAGACA  1429
Consensus  NGNTTNTNNA  ATNNCCCAAA  GCNNATGACN  CTGNANGNNA
                                              1,540                      1,560
                                                |                          |
     HGyV  TGGGAGACCT  GTTAGGGGGC  TGGCAGCTAT  TCAGGCATGT  1515
   M55918  TGGGTCGCAT  GTTTGGGGGC  TGGCACCTGT  TCCGACACAT  1469
Consensus  TGGGNNNCNT  GTTNGGGGGC  TGGCANCTNT  TCNGNCANNT
                                              1,580                      1,600
                                                |                          |
     HGyV  AAAAACCAAG  TTCAGAGTGC  TAGCGACTAT  GGGACAAGGG  1555
   M55918  TGAAACCCGC  TTTCAGCTCC  TTGCCACTAA  GAATGAGGGA  1509
Consensus  NNAAACCNNN  TTNNNNNTNC  TNGCNACTAN  GNNNNANGGN
                                              1,620                      1,640
                                                |                          |
     HGyV  GCTTTCTCAC  CAGTTGCAAG  CCTACTTGTA  CAAAATGACT  1595
   M55918  TCCTTCAGCC  CCGTGGCGAG  TCTTCTCTCC  CAGGGAGAGT  1549
Consensus  NCNTTCNNNC  CNGTNGCNAG  NCTNCTNNNN  CANNNNGANT
                                              1,660                      1,680
                                                |                          |
     HGyV  ACTGGAGCAG  GAGGCACTTA  GAGGGCTTCC  CAGTTAAAGG  1635
   M55918  ACCTCA----  ----CGCGTC  GGGACGATGT  TAAGTACAG-  1580
Consensus  ACNNNAGCAG  GAGGCNCNTN  GNGNNNNTNN  NANNTANAGG
                                              1,700                      1,720
                                                |                          |
     HGyV  TGCACCACCT  ATGTGCACCA  TGCAAAGAAA  AACTCAGCAG  1675
   M55918  --CAGCGATC  ACCAGAACCG  -GTGGCAAAA  AGGCGGACAA  1617
Consensus  TGCANCNNNN  ANNNGNACCN  TGNNNNNAAA  ANNNNNNCAN
                                              1,740                      1,760
                                                |                          |
     HGyV  TACGGCAACG  TGGAGTCCAA  TGCACCGGCA  GATGAGCAAT  1715
   M55918  C-CGATGACG  GGGGG--CAT  TGCTTATGCG  ACCGGGAAAA  1654
Consensus  NACGNNNACG  NGGNGTCCAN  TGCNNNNGCN  NNNGNGNAAN
                                              1,780                      1,800
                                                |                          |
     HGyV  GGCTACCCGT  AAATCCCCCA  GACCCACCAG  TGTACCCAAA  1755
   M55918  TGAGACCCGA  CGAGCAACAG  TACCCTGCTA  TGCCCCCAGA  1694
Consensus  NGNNACCCGN  NNANCNNCNN  NACCCNNCNN  TGNNCCCANA
                                              1,820                      1,840
                                                |                          |
     HGyV  CCAGGGAGGA  TGCTCCCAAA  ACGTGGCTCC  AGGCATATAC  1795
   M55918  CCCCCCGATC  ATCACCGCTA  CTACAGCGCA  AGGCACGCAA  1734
Consensus  CCNNNNNNNN  NNCNCCNNNA  NNNNNGCNCN  AGGCANNNAN
                                              1,860                      1,880
                                                |                          |
     HGyV  CGGCTTGCAG  GCTTAGAAGA  CAGCAGCAGA  TGCTTTTATT  1835
   M55918  ------GTCC  GCTGCATGAA  TAGCACGCAA  GCTTGGTGGT  1768
Consensus  CGGCTTGNNN  GCTNNNNNNA  NAGCANNNNA  NNNTNNTNNT
                                              1,900                      1,920
                                                |                          |
     HGyV  CAAAGGCTTG  TTTCCCCAGC  TTTGCAGCGC  TTTCTGCTAT  1875
   M55918  CATGGGACAC  ATATATGAGC  TTTGCAACAC  TCACAGCACT  1808
Consensus  CANNGGNNNN  NTNNNNNAGC  TTTGCANCNC  TNNCNGCNNT
                                              1,940                      1,960
                                                |                          |
     HGyV  GGGTGCACCC  TGGTCATTTC  CTAGCACTCA  AAAACCTATT  1915
   M55918  CGGTGCACAA  TGGTCTTTTC  CTCCAGGGCA  ACGTTCAGTT  1848
Consensus  NGGTGCACNN  TGGTCNTTTC  CTNNNNNNCA  ANNNNCNNTT
                                              1,980                      2,000
                                                |                          |
     HGyV  CAAAGAGGCT  CATTTAACAA  GCACTCCATC  ACGGGGACAG  1955
   M55918  TCTAGACGGT  CCTTCAACCA  CCACAAGGCG  AGAGGAGCCG  1888
Consensus  NNNAGANGNT  CNTTNAACNA  NCACNNNNNN  ANNGGNNCNG
                                              2,020                      2,040
                                                |                          |
     HGyV  GGGACCCCCA  GGGCCGACGG  TGGTTAACAC  TTGTGCCTAA  1995
   M55918  GGGACCCCAA  GGGCCAGAGA  TGGCACACGC  TGGTGCCGCT  1928
Consensus  GGGACCCCNA  GGGCCNNNGN  TGGNNNACNC  TNGTGCCNNN
```

Figure 2 continued

```
                                         2,060                          2,080
                                           |                              |
      HGyV  AGGAGTCGAG  TGGATTACTG  ACGACACCAT  G---GAACCT  2032
    M55918  CGGCACGGAG  ACCATCACCG  ACAGCTACAT  GTCAGCACCC  1968
 Consensus  NGGNNNNGAG  NNNATNACNG  ACNNCNNCAT  GTCAGNACCN
                                         2,100                          2,120
                                           |                              |
      HGyV  ACGC---AAC  TGGACACAGA  CATTGCAACA  CTCTTCTTGG  2069
    M55918  GCATCAGAGC  TGGACACTAA  TTTCTTTACG  CTTTACGTAG  2008
 Consensus  NCNNCAGANC  TGGACACNNA  NNTNNNNACN  CTNTNCNTNG
                                         2,140                          2,160
                                           |                              |
      HGyV  CTCAAGGCAG  TCCAGTATGG  GCACCCTACA  AATTCGGAAC  2109
    M55918  CGCAAGGCAC  AAATAAGTCG  CAACAGTACA  AGTTCGGCAC  2048
 Consensus  CNCAAGGCAN  NNNNNNNTNG  NNACNNTACA  ANTTCGGNAC
                                         2,180                          2,200
                                           |                              |
      HGyV  TTTTCACAAA  GCGATGGCGC  TAACAGCGAT  GCAGACCACC  2149
    M55918  AGCTACATAC  GCGCTAAAGG  AGCCGGTAAT  GAAGAGCGAT  2088
 Consensus  NNNTNNNNAN  GCGNTNNNGN  NNNCNGNNAT  GNAGANCNNN
                                         2,220                          2,240
                                           |                              |
      HGyV  CCTTGGTGCG  TGGTGAAAGT  CCGTTCCATC  TGGCAGCTCG  2189
    M55918  GCATGGGCAG  TGGTACGCGT  CCAGTCGGTC  TGGCAGCTGG  2128
 Consensus  NCNTGGNNNG  TGGTNNNNGT  CCNNTCNNTC  TGGCAGCTNG
                                         2,260                          2,280
                                           |                              |
      HGyV  GCAACCAAAG  ACAGCCGTAC  CCATGGCAAG  TGAACTGGTA  2229
    M55918  GTAACAGGCA  GAGGCCATAC  CCATGGGACG  TCAACTGGGC  2168
 Consensus  GNAACNNNNN  NNNGCCNTAC  CCATGGNANG  TNAACTGGNN
                                         2,300                          2,320
                                           |                              |
      HGyV  CAACGAGCAC  ACTGCAACGG  ACAGATACAA  CCC-------  2262
    M55918  GAAC-AGCAC  CATGTACTGG  G-GGACGCAG  CCCTGAAAAG  2206
 Consensus  NAACGAGCAC  NNTGNANNGG  NCNGANNCAN  CCCTGAAAAG
                                         2,340                          2,360
                                           |                              |
      HGyV  ----------  ----------  ----------  ----------  2262
    M55918  GGGGGGGGGC  TAAAGCCCCC  CCCCCTTAAA  CCCCCCCCTG  2246
 Consensus  GGGGGGGGGC  TAAAGCCCCC  CCCCCTTAAA  CCCCCCCCTG
                                         2,380                          2,400
                                           |                              |
      HGyV  ----------  --------GC  CCCCCGTCAA  TAAATAATTA  2284
    M55918  GGGGGGATTC  CCCCCCAGAC  CCCCCCTTTA  TATAGCACTC  2286
 Consensus  GGGGGGATTC  CCCCCCAGNC  CCCCCNTNNA  TANANNANTN
                                         2,420
                                           |
      HGyV  AATAAACC--  --AAATCGAA  TTATTTATTT  ATTTT  2315
    M55918  AATAAACGCA  GAAAATAGAT  TTATCGCACT  ATC--  2319
 Consensus  AATAAACNCA  GAAAATNGAN  TTATNNNNNT  ATNTT
```

Figure 2 continued

```
                                         20                                40
                                          |                                 |
P69485_VP2  MHGNGG----  ----QPAAGG  SESALSREGQ  PGPSGAAQ-G  31
     H-VP2  -MSSGGLGDC  SACENRAAGG  SELPLRQEGQ  LGPSGAGSTG  39
 Consensus  MXXXGGLGDC  SACEXXAAGG  SEXXLXXEGQ  XGPSGAXXTG
                                         60                                80
                                          |                                 |
P69485_VP2  QVISNER--S  P--RRYSTRT  INGVQATNKF  TAVGNPSLQR  67
     H-VP2  KTLNADPPLS  PTSNNYSVRT  INGIRASNKF  VSASRNDLDR  79
 Consensus  XXXXXXXPLS  PTSXXYSXRT  INGXXAXNKF  XXXXXXXLXR
                                        100                               120
                                          |                                 |
P69485_VP2  DPDWYRWNYN  HSIAVWLREC  SRSHAKICNC  GQFRKHWFQE  107
     H-VP2  DPNWYRVNYN  YSIATWLRQC  ARSHDEICTC  GRWRSHWFQE  119
 Consensus  DPXWYRXNYN  XSIAXWLRXC  XRSHXXICXC  GXXRXHWFQE
                                        140                               160
                                          |                                 |
P69485_VP2  CAGLEDRSTQ  ASLEEAILRP  LRVQGKRAKR  KLDYHYSQPT  147
     H-VP2  ASGLVTQETQ  TDQLARDLRR  LRRKGEAAKR  KLDYLKGKRT  159
 Consensus  XXGLXXXXTQ  XXXXXXXLRX  LRXXGXXAKR  KLDYXXXXXT
                                        180                               200
                                          |                                 |
P69485_VP2  PNRKKVYKTV  RWQ----DEL  ADREADFTPS  EEDGGTTSSD  183
     H-VP2  PYKKA--KTV  TWQDYEEDDL  ADALASTT--  -EDDGTGDTD  194
 Consensus  PXXKXVYKTV  XWQDYEEDXL  ADXXAXXTPS  EEDXGTXXXD
                                        220
                                          |
P69485_VP2  FDED-----I  NFDIGGDSGI  VDELLGRPFT  -TPAPVRIV  216
     H-VP2  CDEDAIPGGV  NFDMRVEDPL  IAALRGGSST  HTRAPMW*-  232
 Consensus  XDEDAIPGGX  NFDXXXXXXX  XXXLXGXXXT  HTXAPXXIV
```

Figure 5

```
                                      20                      40  LRS                       60
                                       |                       |                             |
A-apoptin_P54094  MNALQE----  -DTPPGPSTV  FRPPTSSRPL  ETPHCREIRI  GIAGITITLS  LCGCANARAP  55
       H-apoptin  MQTPRSRRRA  TTTQSELLTA  YEHPTSSSPP  AETTSIEIQI  GIGSTIITLS  LPGYASVRVL  60

                                      80      NLS1           100           NES        120
                                       |                       |                        |
A-apoptin_P54094  TLRSATADNS  ESTGFKNVPD  LRTDQPKPPS  KKRSCDPSEY  -----RVSEL  KESLITTTPS  110
       H-apoptin  TTRSAPADDG  GVTGSRRLVD  LSHRRPR---  --RTSSPEIY  VGFAAKEKQQ  KENLITLREN  115

                     NLS2
A-apoptin_P54094  RPRTARRCIR  L-  121
       H-apoptin  GPPIKK--LR  L*  125
```

Figure 6

IDENTIFICATION OF A HUMAN GYROVIRUS AND APPLICATIONS

This application is the U.S. National Stage of International Application No. PCT/EP2011/071086, filed Nov. 25, 2011, which claims the benefit of European Application No. 10306307.9, filed Nov. 26, 2010, and of U.S. Provisional Application No. 61/449,930, filed Mar. 7, 2011.

The present invention first relates to the identification of a human gyrovirus HGyV, related to the chicken anemia virus (CAV). The present invention also relates to new proteins encoded by HGyV, which proteins display some homology to CAV proteins. Among these new proteins, H-apoptin is of particular interest as it is found for the first time in a human virus and can be used for treating cancer. Also provided are methods for detecting the HGyV virus in biological samples.

INTRODUCTION

During the course of a research program looking for pathogens present in biological samples, we have identified and isolated for the first time a new human virus that we have designated as Human Gyrovirus (HGyV) because of its homology with the chicken anemia virus, the only previously known virus in the Gyrovirus genus.

The chicken anemia virus (CAV) is highly contagious and causes severe anemia, hemorrhaging, and depletion of lymphoid tissue through the destruction of bone marrow erythroblastoid cells in young chicken. CAV is the only species of the genus Gyrovirus, which are a part of the family of Circoviridae, and consists of a non-enveloped, round, icosahedral capsid, 19-27 nm in diameter. The CAV genome consists of a single molecule of circular, single-stranded negative-sense DNA that forms a closed circle. The complete genome is 2290-2320 nucleotides long and contains three partially overlapping open reading frames which produce a single polycistronic unspliced mRNA encoding three proteins VP1, VP2, and VP3. The 5'-nontranscribed sequences of the CAV genome are the sole promoter enhancer for CAV; they comprise 6 direct repeats of sequence AGCTCA similar to the estrogen response element (ERE) consensus half-sites (A)GGTCA (Noteborn et al., *Gene,* 150: 313-318, 1994; Miller et al., *J. Virol.,* 79(5): 2859-2868, 2005).

The VP1 protein is a 51-kDa capsid protein (WO 96/01116). In addition to its structural function, it also contains motifs for rolling circle replication in the C-terminal region. VP2 is a 24-kDa non-structural protein with dual-specificity phosphatase activity. Virions with mutations in SP2 are still replication competent; however, their cytopathic effects are highly attenuated. VP3, also designated apoptin, is a 13-kDa protein that has been shown to independently induce apoptosis in chicken cells both in vitro and in vivo (Koch et al., *Vaccine,* 13: 763-770, 1995; Noteborn et al., *J. Virol.,* 65: 3131-3139, 1991; Noteborn et al., *J. Virol.,* 68: 346-351, 1994; Todd et al., *J. Gen. Virol.,* 71(Pt 4): 819-823, 1990).

Apoptin is composed of 121 amino acids, and does not show significant homology with known cellular proteins. Several proteins motifs, however, can be readily identified in the protein. For example, the C-terminus of apoptin contains a bipartite nuclear-localization sequence (NS) and a putative nuclear export sequence (NES) (Tavassoli et al., *Apoptosis,* 10: 717-724, 2005; Los et al., *Biochim Biophys Acta,* 1793(8): 1335-42, 2009). A phosphorylation site (Thr-108) is located close to the NES; phosphorylation at this site may regulate tumor-specific nuclear accumulation of the protein via inactivation of the NES (WO 02/32954; Rohn et al., *J. Biol. Chem.,* 277: 50820-50827, 2002; Tavassoli et al., *Apoptosis,* 10: 717-724, 2005; Los et al., *Biochim Biophys Acta,* 1793(8): 1335-42, 2009). Apoptin also harbors in its N-terminus a short hydrophobic leucine-rich stretch which is required for self-association as well as binding to other partners (Leliveld et al., *J. Biol. Chem.,* 278: 9042-9051, 2003; Teodoro et al., *Genes Dev.,* 18: 1952-1957, 2004; Maddika et al., *J Cell Sci,* 118(Pt 19): 4485-4493, 2005; Maddika et al., *Cell Prolif,* 40(6): 835-848, 2008; Maddika et al., *Oncogene,* 27: 3060-3065, 2008; Los et al., *Biochim Biophys Acta,* 1793(8): 1335-42, 2009).

Apoptin is capable of inducing apoptosis in human malignant and transformed cell lines, but not in untransformed cell cultures (Danen-van Oorschot et al., *Proc. Natl. Acad. Sci. U.S.A.,* 94: 5843-5847, 1997). In vitro and in vivo, apoptin fails to induce apoptosis in a variety of normal cells, including human endothelial cells, hepatocytes and hematopoietic stem cells. Moreover, the safety of apoptin is confirmed by the fact that continuous expression of apoptin in transgenic mice does not interfere with development and proliferation of both lymphocytes and melanocytes (Pietersen et al., *J. Med. Mol. Biol.,* 2: 321-330, 2005; Los et al., *Biochim Biophys Acta,* 1793(8): 1335-1342, 2009; Xiao et al., *Mol. Cancer,* 9: 10, 2010).

In normal cells, apoptin was found predominantly in the cytoplasm, whereas in transformed or malignant cells, it is located in the nucleus (Tavassoli et al., *Apoptosis,* 10: 717-724, 2005). Nuclear localization of apoptin appears to be important for its cell killing activity (Danen-van Oorschot et al., *J. Biol. Chem.,* 278(30): 27729-27736, 2003; Tavassoli et al., *Apoptosis,* 10: 717-724, 2005; Heilman et al., *J. Virol.,* 80(15): 7535-7545, 2006; Los et al., *Biochim Biophys Acta,* 1793(8): 1335-1342, 2009).

Apoptin-induced apoptosis is largely independent of p53 function. Indeed, apoptin expression is capable of inducing cell-cycle arrest and apoptosis in p53 null cells (WO 96/41191; Teodoro et al., *Genes Dev.,* 18: 1952-1957, 2004; Zuang et al., *Cancer Res.,* 55: 486-489, 1995). The p53 pathway is the major mechanism by which cancer cells are destroyed by chemotherapy and radiotherapy (Soussi and Lozano, *Biochem. Biophys. Res. Commun.,* 331: 834-842, 2005). However, because the p53 gene is mutated in approximately half of all human tumors, cancer cells are often refractory to these forms of therapy (Scherr, *Cell,* 116: 235-246, 2004). The p53-independent and tumor-specific properties associated with apoptin thus make it a very important candidate for cancer therapy.

However, apoptin is derived from a bird-specific virus and therefore, may not be as efficient in inducing apoptosis in human tumor cells as a genuine human protein. It can be anticipated that a human apoptin should be more potent in mammals than its avian counterpart.

Considering the above, we now provide a new human virus which presents oncolytic activities specific to proliferative cells and thus which is directly useful in the treatment of cancer, especially in human. In addition, we also provide the human apoptin protein which can be directly used as a biotherapeutic to treat cancer in human and animals.

DESCRIPTION

In a first aspect, the present invention provides a new human virus homologous to the CAV. This new virus, designated HGyV (for Human Gyrovirus), was identified at the surface of the skin from healthy people. Its genome shows homology with the CAV genome, both at the nucleotide and organizational levels. By "CAV genome", it is herein referred to a genome having a sequence such as in e.g. Genbank accession No M55918 and represented in SEQ ID NO: 8, and comprising a 5' region with promoter features and three overlapping open reading frames. The said open reading frames have nucleotide sequences represented by SEQ ID: 9, SEQ ID: 10, and SEQ ID: 11. The said open reading frames code for the VP1, VP2 and apoptin polypeptides respectively; as an example, such polypeptides may have sequences represented by e.g. SEQ ID: 12, SEQ ID: 13, and SEQ ID: 14. Whereas CAV is specific for avian cells, HGyV is capable of replicating in human cells.

The present invention thus provides an isolated polynucleotide sequence, wherein said polynucleotide is a human virus genome and said sequence comprises a 5' promoter region and/or three partially open reading frames.

In a preferred embodiment, the genome of the HGyV virus contains a 5' region with promoter features. A "promoter" as used herein is a sequence which is capable of directing expression of an open reading frame operationally linked to said sequence. Specific regulatory DNA sequences (cis-elements) in the promoter serve as binding sites for transcription factors (trans-acting factors). The cis-elements found in gene promoters can be divided in two categories. The first category comprises those cis-elements which are involved in initiation of transcription, such as the TATA box and the CAAT box. The second category is composed of cis-elements which are involved in temporal and spatial regulation of gene expression; examples of such cis-elements include the direct repeats of sequence represented by SEQ ID NO: 29: AGCTCA found in the CAV promoter.

Preferably, the said 5' HGyV promoter region includes repeated cis-elements having sequences homologous to the estrogen response element (ERE) consensus half-sites represented by SEQ ID NO 30: (A)GGTCA. More preferably, the said 5' region comprises repeated cis-elements which sequences show at least 85%, preferably at least 90%, more preferably at least 95%, yet still more preferably at least 98% identity with the sequence represented by SEQ ID NO: 31: ACGTCA. In the most preferred embodiment, the said 5' region comprises repeated cis-elements having the sequence represented by SEQ ID NO: 31. Preferably, the said 5' region contains at least 2 repeated cis-elements as defined above, more preferably at least 3, even more preferably at least 4. The said 5' HGyV promoter region may further include a cis-element consisting of a palindromic sequence; preferably, the said palindromic sequence is the sequence represented by SEQ ID NO: 17: CAATCAGAATTG.

According to the present invention, the genome of HGyV virus of the invention may also comprise three partially overlapping open reading frames. The present inventors found in particular that the said open-reading frames show homology at the nucleotide level with the CAV VP1, VP2, and VP3 (apoptin) genes, respectively.

Thus, the invention provides an H-VP1 open reading frame which has a sequence sharing at least 55%, 60%, 65%, 70%, 75%, 80%, 85%, 87.5%, 90%, 92.5%, 95%, 96%, 97%, 98%, 99%, 99.5%, or 99.9% identity with the sequence represented by SEQ ID NO: 2 or with the sequence represented by SEQ ID NO: 34 or with the sequence represented by SEQ ID NO: 38. In a preferred embodiment, the said H-VP1 open reading frame has the sequence represented by SEQ ID NO: 2 or the sequence represented by SEQ ID NO: 34 or with the sequence represented by SEQ ID NO: 38. More preferably, the said H-VP1 open reading frame has the sequence represented by SEQ ID NO: 34. The invention also relates to an H-VP2 gene which sequence has at least at least 65%, 70%, 75%, 80%, 85%, 87.5%, 90%, 92.5%, 95%, 96%, 97%, 98%, 99%, 99.5%, or 99.9% identity with the sequence represented by SEQ ID NO: 4. In another preferred embodiment, the said H-VP2 open reading frame has the sequence represented by SEQ ID NO: 4. The invention also refers to an H-VP3 open reading frame which has a sequence with at least 65%, 70%, 75%, 80%, 85%, 87.5%, 90%, 92.5%, 95%, 96%, 97%, 98%, 99%, 99.5%, 99.9% identity with the sequence represented by SEQ ID NO: 6. In still another preferred embodiment, the said H-VP3 gene has a sequence represented by SEQ ID NO: 6. The invention thus relates to an isolated polynucleotide, wherein the said polynucleotide is selected from the group consisting of:

a H-VP1 gene having a sequence with at least 55% identity with the sequence represented by SEQ ID NO: 2 or with the sequence represented by SEQ ID NO: 34 or with the sequence represented by SEQ ID NO: 37;

a H-VP2 gene having a sequence with at least 65% identity with the sequence represented by SEQ ID NO: 4; and a H-VP3 gene having a sequence with at least 65% identity with the sequence represented by SEQ ID NO: 6.

The HGyV virus of the invention may contain all three of the H-VP1, the H-VP2, and the H-VP3 genes. In a preferred embodiment, the HGyV virus of the invention has a sequence displaying at least 60%, 65%, 70%, 75%, 80%, 85%, 87.5%, 90%, 92.5%, 95%, 96%, 97%, 98%, 99%, 99.5%, 99.9% identity with the sequence represented by SEQ ID NO: 1. In another preferred embodiment, the HGyV virus of the invention has a sequence displaying at least 60%, 65%, 70%, 75%, 80%, 85%, 87.5%, 90%, 92.5%, 95%, 96%, 97%, 98%, 99%, 99.5%, 99.9% identity with the sequence represented by SEQ ID NO: 37. This sequence corresponds to another HGyV molecular clone, wherein a 60-nucleotide insertion is present between positions 2263 and 2264 of the sequence represented by SEQ ID NO: 1 In the most preferred embodiment of the invention, the HGyV virus of the invention has a sequence selected from the group consisting of the sequences represented by SEQ ID NO: 1 and SEQ ID NO: 37.

It also relates to the HGyV virus, in a recombinant form (meaning that the virus displays at least one modification from naturally occurring virus), to the HGyV virus in the form of complementary sequence of SEQ ID NO: 1 or SEQ ID NO: 37, or even to the HGyV virus in the form of complete cDNA of SEQ ID NO: 1 or SEQ ID NO: 37. The invention also encompasses parts of said HGyV virus as defined above comprising at least 100, 200 or 500 consecutive nucleotides of the sequence as defined above (SEQ ID NO: 1 or SEQ ID NO: 37, complementary sequence thereof or cDNA thereof). In another aspect, the invention also relates to an HGyV viral particle containing the said HGyV virus.

The term "sequence identity" refers to the identity between two peptides or between two nucleic acids. Identity between sequences can be determined by comparing a position in each of the sequences which may be aligned for the purposes of comparison. When a position in the compared sequences is occupied by the same base or amino acid, then the sequences are identical at that position. A degree of sequence identity between nucleic acid sequences is a function of the number of identical nucleotides at positions shared by these sequences. A degree of identity between amino acid sequences is a function of the number of identical amino acid sequences that are shared between these sequences. Since two polypeptides may each (i) comprise a sequence (i.e. a portion of a complete polynucleotide sequence) that is similar between two polynucleotides, and (ii) may further comprise a sequence that is divergent between two polynucleotides, sequence identity comparisons between two or more polynucleotides over a "comparison window" refers to the conceptual segment of at least 20 contiguous nucleotide positions wherein a polynucleotide sequence may be compared to a reference nucleotide sequence of at least 20 contiguous nucleotides and wherein the portion of the polynucleotide sequence in the comparison window may comprise additions or deletions (i.e. gaps) of 20 percent or less compared to the reference sequence (which does not comprise additions or deletions) for optimal alignment of the two sequences.

To determine the percent identity of two amino acids sequences or two nucleic acid sequences, the sequences are aligned for optimal comparison. For example, gaps can be introduced in the sequence of a first amino acid sequence or a first nucleic acid sequence for optimal alignment with the second amino acid sequence or second nucleic acid sequence. The amino acid residues or nucleotides at corresponding amino acid positions or nucleotide positions are then compared. When a position in the first sequence is occupied by the same amino acid residue or nucleotide as the corresponding position in the second sequence, the molecules are identical at that position. The percent identity between the two sequences is a function of the number of identical positions shared by the sequences. Hence % identity=number of identical positions/total number of overlapping positions ×100.

In this comparison the sequences can be the same length or can be different in length. Optimal alignment of sequences for determining a comparison window may be conducted by the local homology algorithm of Smith and Waterman (*J. Theor. Biol.,* 91(2): 370-380, 1981), by the homology alignment algorithm of Needleman and Wunsch (*J. Mol. Biol,* 48(3): 443-453, 1972), by the search for similarity via the method of Pearson and Lipman (*Proc. Natl. Acad. Sci. U.S.A.,* 85(5): 2444-2448, 1988), by computerized implementations of these algorithms (GAP, BESTFIT, FASTA and TFASTA in the Wisconsin Genetics Software Package Release 7.0, Genetic Computer Group, 575, Science Drive, Madison, Wis.) or by inspection. The best alignment (i.e. resulting in the highest percentage of identity over the comparison window) generated by the various methods is selected.

The term "sequence identity" means that two polynucleotide or polypeptide sequences are identical (i.e. on a nucleotide by nucleotide or an amino acid by amino acid basis) over the window of comparison. The term "percentage of sequence identity" is calculated by comparing two optimally aligned sequences over the window of comparison, determining the number of positions at which the identical nucleic acid base (e.g. A, T, C, G, U, or 1) occurs in both sequences to yield the number of matched positions, dividing the number of matched positions by the total number of positions in the window of comparison (i.e. the window size) and multiplying the result by 100 to yield the percentage of sequence identity. The same process can be applied to polypeptide sequences. The percentage of sequence identity of a nucleic acid sequence or an amino acid sequence can also be calculated using BLAST software (Version 2.06 of September 1998) with the default or user defined parameter.

The term "sequence similarity" means that amino acids can be modified while retaining the same function. It is known that amino acids are classified according to the nature of their side groups and some amino acids such as the basic amino acids can be interchanged for one another while their basic function is maintained.

The CAV virus mostly infects young chicks of around 10-14 days of age. Outbreaks of the disease are characterized by anemia, thymus atrophy, bone marrow aplasia and immunosuppression. The HGyV virus of the invention should function in a similar way, i.e. young children are expected to be at risk of being affected by an HGyV infection. It is therefore important to be capable of detecting the presence or not of the HGyV virus of the invention, in particular in young children. Detection of the HGyV virus of the infection in pregnant women is also crucial in order to monitor the risk of vertical transmission from the mother to the child.

The invention thus also relates to an in vitro method of detection of an HGyV virus in a a subject, comprising the steps of:

a) determining the presence of the HGyV virus in a biological sample of the said subject.

A "biological sample" may be any sample that may be taken from a subject, and thus includes, but is not limited to, for example, blood, serum, plasma, sputum, urine, stool, skin, cerebrospinal fluid, saliva, gastric secretions, semen, seminal fluid, breast milk, and tears. A sample can be obtained by an oropharyngeal swab, nasopharyngeal swab, throat swab, nasal aspirate, nasal wash, fluid collected from the ear, eye, mouth, or respiratory airway, spinal tissue or fluid, cerebral fluid, trigeminal ganglion sample, a sacral ganglion sample, adipose tissue, lymphoid tissue, placental tissue, upper reproductive tract tissue, gastrointestinal tract tissue, male genital tissue and fetal central nervous system tissue. A sample can also be a pool of individual samples, especially those made during the process of manufacturing of biological samples obtained from humans (blood or urine derived products, for example), or any intermediate product sampled during the manufacturing of such products. Such sample must allow the determination of the presence of HGyV through the methods of the invention.

The presence of the HGyV virus may be determined by any technology known to a man skilled in the art. In particular, the HGyV virus may be detected at the genomic and/or nucleic and/or protein level. The method according to the invention may thus comprise another preliminary step, between the taking of the sample from the patient and step a) as defined above, corresponding to the transformation of the biological sample into a genomic DNA sample, or into an mRNA (or corresponding cDNA) sample, or into a protein sample, which is then ready to use for in vitro detection of HGyV in step a). Once a ready-to-use genomic DNA, mRNA (or corresponding cDNA) or protein sample is available, the detection of the HGyV virus may be performed, depending on the type of transformation and the available ready-to-use sample, either at the genomic DNA (i.e. based on the presence of at least one sequence consisting of at least a part of the HGyV genome as defined above), mRNA (i.e. based on the mRNA content of the sample) or at the protein level (i.e. based on the protein content of the sample).

Methods for detecting a genomic nucleic acid in a biological sample include inter alia hybridization with a labeled probe, genomic PCR, nucleic microarrays, high-throughput sequencing, and all other methods known to the person of skills in the art. The amount of nucleic acid transcripts can be measured by any technology known by the skilled person. In particular, the measure may be carried out directly on an extracted messenger RNA (mRNA) sample, or on retrotranscribed complementary DNA (cDNA) prepared from extracted mRNA by technologies well-known in the art. From the mRNA or cDNA sample, the amount of nucleic acid transcripts may be measured using any technology known by a person skilled in the art, including nucleic microarrays, quantitative PCR, and hybridization with a labeled probe.

In a preferred embodiment, the presence of the said virus is determined by hybridization of probes specific for the said virus or parts thereof with the biological sample. In another embodiment, amplification and/or sequencing of the HGyV sequences is performed in order to assess the presence of the said virus. In yet another embodiment, the presence of the HGyV virus is determined by detecting a protein produced by at least one of the three open reading frames, H-VP1, H-VP2, and H-VP3.

Another object of the invention therefore relates to a probe capable of hybridizing to the genomic DNA of HGyV. By "probe capable of hybridizing", one should understand that the said probe is substantially complementary to at least part of the HGyV virus genome. For example, the said probe comprises a nucleotide sequence displaying at least 50%, 55%, 65%, 70%, 75%, 80%, 85%, 87.5%, 90%, 92.5%, 95%, 96%, 97%, 98%, 99%, 99.5%, 99.9% identity with at least a part of a sequence of the genomic DNA of HGyV. The probe of the invention comprises at least 12 nucleotides, more preferably at least 15 nucleotides, even more preferably at least 20 nucleotides. According to a specific embodiment, the method of the invention is performed by hybridization with the probes of the invention. Detection of a hybridization signal is thus indicative of the presence of a HGyV virus in the biological sample. It is advantageous to use labelled probes in this embodiment.

The present invention also includes primers specific for the HGyV virus. Preferably, the said primers have the sequences as laid out in SEQ ID NOS: 21-28. The said primers can be used for amplification of specific regions of the HGyV virus of the invention. The amplification may be carried out directly on genomic DNA, on an extracted messenger RNA (mRNA) sample, or on retrotranscribed complementary DNA (cDNA) prepared from extracted mRNA by technologies well-know in the art. The said primers of the invention can also be used for sequencing the HGyV virus. Alternatively, the said HGyV virus is detected by high-throughput sequencing. Many such methods are already known to the man of skills in the art; according to some of the methods, amplification of the template prior to sequencing may be required (see, for a few examples, Mitreva & Mardis, *Methods Mol Biol.,* 533:153-87, 2009; Mardis, *Genome Med.,* 1(4): 40, 2009; Cloonan et al., *Nat Methods,* 5(7): 613-619, 2008; Valouev et al., *Genome Res.,* 18(7):1051-63, 2008, Valouev et al., *Nat Methods.,* 5(9): 829-34, 2008; Orscheln et al., *Clin Infect Dis.,* 49(4):536-42, 2009; Walter et al., *Proc Natl Acad Sci USA.,* 106(31):12950-5, 2009; Mardis et al., *N Engl J Med.,* 361(11):1058-66, 2009, Hutchinson, *Nucl. Acids Res.,* 35(18): 6227-6237, 2007; Shendure & Ji, *Nat Biotechnol.,* 26(10):1135-45. 2008; Pihlak et al., *Nat Biotechnol.,* 26(6): 676-684, 2008; Fuller et al., *Nature Biotechnol.,* 27(11): 1013-1023, 2009; Mardis, *Genome Med.,* 1(4): 40, 2009; Metzker, *Nature Rev. Genet.,* 11(1): 31-46, 2010).

An embodiment of the present invention thus provides a method of detection of an HGyV virus comprising a step of amplification and/or sequencing of the said virus using the primers of the invention. In this particular embodiment, amplification or sequencing of nucleic acid using the primers of the invention is indicative of the presence of the HGyV virus in the said sample. When referring to sequencing, it is within the scope of the invention to detect HGyV in samples, or to screen for HGyV in biological materials, with deep sequencing techniques, such as pyro-sequencing.

When the HGyV virus is detected at the protein level, it may be notably performed using specific antibodies, in particular using well known technologies such as cell membrane staining using biotinylation or other equivalent techniques followed by immunoprecipitation with specific antibodies, western blot, ELISA or ELISPOT, antibodies microarrays, or tissue microarrays coupled to immunohistochemistry. Other suitable techniques include FRET or BRET, single cell microscopic or histochemistery methods using single or multiple excitation wavelength and applying any of the adapted optical methods, such as electrochemical methods (voltametry and amperometry techniques), atomic force microscopy, and radio frequency methods, e.g. multipolar resonance spectroscopy, confocal and non-confocal, detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry), cell ELISA, flow cytometry, radioisotopic, magnetic resonance imaging, analysis by polyacrylamide gel electrophoresis (SDS-PAGE); HPLC-Mass Spectroscopy; Liquid Chromatography/Mass Spectrometry/Mass Spectrometry (LC-MS/MS)). All these techniques are well known in the art and need not be further detailed here.

In another aspect, the invention provides a HGyV protein produced by the HGyV virus of the invention. By "HGyV protein", it is herein referred to a protein encoded by one of the open reading frames of the human virus of the invention. The HGyV protein of the invention is thus a protein encoded by anyone of the polynucleotide described above. In particular, the HGyV protein of the invention is encoded by anyone of the three open reading frames of the HGyV virus of the invention, H-VP1, H-VP2, and H-VP3, as defined above.

In a preferred embodiment, the HGyV protein is H-VP1p and has a sequence showing at least 45%, 50%, 55%, 65%, 70%, 75%, 80%, 85%, 87.5%, 90%, 92.5%, 95%, 96%, 97%, 98%, 99%, 99.5%, 99.9% identity with a sequence represented by SEQ ID NO: 3 or with the sequence represented by SEQ ID NO: 35 or with the sequence represented by SEQ ID NO: 39. More preferably, the H-VP1p protein of the invention has the sequence represented by SEQ ID NO: 3 or the sequence represented by SEQ ID NO: 35 or the sequence represented by SEQ ID NO: 39. Even more preferably, the H-VP1p protein of the invention has the sequence represented by SEQ ID NO: 35. In another preferred embodiment, the HGyV protein is a H-VP2p and has a sequence showing at least 50%, 55%, 65%, 70%, 75%, 80%, 85%, 87.5%, 90%, 92.5%, 95%, 96%, 97%, 98%, 99%, 99.5%, 99.9% identity with a sequence represented by SEQ ID NO: 5. Still more preferably, the H-VP2p protein of the invention has the sequence represented by SEQ ID NO: 5. In yet another preferred embodiment, the HGyV protein is H-apoptin and has a sequence showing at least HGyV protein has a sequence showing at least 35%, 40%, 45%, 50%, 55%, 65%, 70%, 75%, 80%, 85%, 87.5%, 90%, 92.5%, 95%, 96%, 97%, 98%, 99%, 99.5%, 99.9% identity with a sequence represented by SEQ ID NO: 7. In a further preferred embodiment, the H-apoptin protein of the invention may comprise one or several protein motifs similar to the ones found in the avian apoptin protein. In particular, the H-apoptin of the invention may contain a leucine-rich stretch, a nuclear exportation signal (NES) and/or at least one nuclear localization signal. Advantageously, the said H-apoptin protein contains in addition a phosphorylation site close to the NES. Preferably, the said phosphorylation site corresponds to the threonine residue at position 110 in SEQ ID NO: 7. In a more preferred embodiment, the H-apoptin protein of the invention has the sequence represented by SEQ ID NO: 7.

The invention thus relates to an isolated polypeptide, wherein the said polypeptide is selected from the group consisting of:

a H-VP1p polypeptide having a sequence with at least 45% identity with the sequence represented by SEQ ID NO: 3 or with the sequence represented by SEQ ID NO: 35 or with the sequence represented by SEQ ID NO: 39;

a H-VP2 polypeptide having a sequence with at least 50% identity with the sequence represented by SEQ ID NO: 5; and a H-apoptin polypeptide having a sequence with at least 35% identity with the sequence represented by SEQ ID NO: 7.

In a particular embodiment, the polypeptide of the invention is associated to a cell-penetrating peptide (CPP). As used herein, "CPP" refers to a small (10-30 residues in length), often positively charged sequence of amino acids which has the ability to enter cells independent of a membrane receptor, and show no cell-type specificity (see Richard et al., *J. Biol. Chem,* 278(1): 585-590, 2003; Patel et al., *Pharm Res,* 24(11): 1977-1992, 2007). The CPPs of the invention facilitate cellular uptake of the said polypeptide, preferentially H-apoptin, through endocytosis with the said polypeptide delivered to the endosomes of living mammalian cells. In a preferred embodiment, the CPP of the invention include such sequences as the nuclear transcription activator Tat protein, Tat-(47-57) (SEQ ID NO: 40; YGRKKRRQRRR), the regulator of expression of virion Rev protein, HIV-1 Rev-(34-50) (SEQ ID NO: 41; TRQARRNRRRR WRERQR), both encoded by HIV-1, the *Drosophila Antennapedia* protein, Antp-(43-58) (SEQ ID NO: 42; RQIKIYFQNRRMKWKK), flock house virus (FHV) coat-(35-49) (SEQ ID NO: 43; RRRRNRTRRNRRRVR), small oligoarginine, $(R)_n$, small oligolysine, $(K)_n$, the model amphipathic peptide MAP, (SEQ ID NO: 44; KLALKLALKALKAALKLA), transportan (SEQ ID NO: 45; GWTLNSAGYLLGKINLKALAALAKKIL), pisl (SEQ ID NO: 46; RVIRVWFQNKRCKDKK), Pep-1 (SEQ ID NO: 47; KETWWVETWWVTEWSQPKKKRRV), the protein transduction domain 4, PTD4 (SEQ ID NO: 48: YARAAARQARA), and the protein transduction domain PTD (SEQ ID NO: 49; ARAAAAQARA). In a further preferred embodiment, the CPP of the invention is PTD4 or PTD. In the most preferred embodiment, the CPP of the invention is PTD.

The CPP of the invention can be associated to the said polypeptide either through non-covalent interactions or through a covalent bond. Preferably, the CPP is associated with the polypeptide of the invention through a covalent bond.

Advantageously, the association of the CPP with the polypeptide of the invention results from a fusion at the genetic level. In this embodiment, the genes of the CPP and of the polypeptide of the invention form a single transcriptional and translational unit leading to the synthesis of a CPP fusion protein. Thus the present invention is also directed to an isolated polynucleotide comprising an open reading frame encoding a CPP fused in frame to an H-apoptin (H-VP3) gene. The invention also provides a fusion protein comprising a CPP domain fused to an H-apoptin polypeptide.

Advantageously, the CPP fusion protein of the invention comprises a linker domain between the CPP and the polypeptide of the invention. Such a linker domain is an amino acid stretch that adopts an extended conformation to allow for maximal flexibility. The linker thus prevents one moiety of the said fusion protein from negatively affecting the function of the other. Linkers have often been used in the art. The skilled person may, for example, refer to the LINKER web server (Xue et al., *Nucleic Acids Res,* 32 (Web Server issue): W562-W565, 2004). A preferred embodiment of the invention is thus directed to an isolated polynucleotide comprising an open reading frame encoding a CPP, an open reading frame encoding a linker, and an H-apoptin (H-VP3) gene, the said polynucleotide encoding a CPP-linker-H-apoptin fusion protein. The invention thus also provides a CPP-linker-H-apoptin fusion protein.

Preferably, the linker has the sequence GGSGGS (SEQ ID NO: 50).

Preferably, the polypeptide of the invention which is associated with CPP is H-apoptin. Apoptin induces apoptosis in tumor cells. The association between H-apoptin and CPP thus improves delivery of apoptin across the cell membrane, into the tumor cell where it exerts its activity. In a further preferred embodiment, H-apoptin is fused to a CPP. Such a CPP-H-apoptin fusion polypeptide is especially useful for cancer therapy. In an even further preferred embodiment, H-apoptin is fused to a CPP which is not PTD4. More preferably, H-apoptin is fused to PTD. Even more preferably, the PTD-H-apoptin fusion comprises a linker. In the most preferred embodiment, the PTD-linker-H-apoptin has the sequence of SEQ ID NO: 58, and is encoded by a polynucleotide having the sequence of SEQ ID NO: 57.

The invention provides recombinant vectors comprising at least one, two or three of the polynucleotides of the invention as defined above, especially at least SEQ ID NO: 7. The polynucleotide of the invention may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art (see, for example, the techniques described in Sambrook et al., 1990, *Molecular Cloning, A Laboratory Manual,* 2d Ed., Cold Spring Harbor Laboratory, Cold Spring Harbor, N.Y. and Ausubel et al., eds., 1998, Current Protocols in Molecular Biology, John Wiley & Sons, NY). Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan. Thus, it is within the scope of the invention to provide a vector for expressing any of the above defined a H-VP1p polypeptide, a H-VP2p polypeptide, a H-apoptin polypeptide, or a CPP-H-apoptin fusion polypeptide, in particular a H-apoptin polypeptide or a CPP-H-apoptin fusion polypeptide.

In order to express the HGyV proteins or CPP fusion proteins of the invention, the polynucleotides encoding said proteins are inserted into expression vectors such that the genes are operatively linked to transcriptional and translational sequences. Expression vectors include plasmids, YACs, cosmids, retrovirus, adenovirus, EBV-derived episomes, and all the other vectors that the skilled man will know to be convenient for ensuring the expression of the protein of interest. Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2p plasmid origin is suitable for yeast, and various viral origins (SV40, polyoma, adenovirus, VSV or BPV) are useful for cloning vectors in mammalian cells. Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

Polynucleotides of the invention and vectors comprising these molecules can be used for the transformation of a suitable host cell. Transformation can be performed by any known method for introducing polynucleotides into a cell host. Such methods are well known of the man skilled in the art and include dextran-mediated transformation, calcium phosphate precipitation, polybrene-mediated transfection, protoplast fusion, electroporation, encapsulation of the polynucleotide into liposomes, biolistic injection and direct microinjection of DNA into nuclei. Therefore, the invention also encompasses a host cell comprising a vector of the invention.

Preferably, the said host cell is a bacterial cell; more preferably, it is a eukaryotic cell; even more preferably it is a mammalian cell. The nature of the host cell will be dictated by the intended use of the vector of the invention. For example, a cloning vector will usually be maintained and propagated in bacterial cells. On the other hand, it will be advantageous to transform an expression vector in a mammalian cell in order to express the HGyV proteins or CPP fusion proteins of the invention. For long-term, high-yield production of recombinant proteins, stable expression is preferred. For example, cell lines which stably express the protein of the invention may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the HGyV protein or CPP fusion protein of the invention. Such engineered cell lines may be particularly useful in screening and evaluation of compounds that interact directly or indirectly with the said HGyV protein.

The protein of the invention may be prepared by growing a culture transformed host cells under culture conditions necessary to express the desired protein. The resulting expressed protein may then be purified from the culture medium or cell extracts. Soluble forms of the protein of the invention can be purified from conditioned media. Membrane-bound forms of protein of the invention can be purified by preparing a total membrane fraction from the expressing cell and extracting the membranes with a non-ionic detergent such as Triton X-100.

The protein can be purified using methods known to those skilled in the art. For example, the protein of the invention can be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) or polyetheyleneimine (PEI) groups. The matrices can be acrylamide, agarose, dextran, cellulose or other types commonly employed in protein purification.

Alternatively, a cation exchange step can be employed. Suitable cation exchangers include various insoluble matrices comprising sulfopropyl or carboxymethyl groups. Sulfopropyl groups are preferred (e.g., S-Sepharose B columns). The purification of the MU-1 protein from culture supernatant may also include one or more column steps over such affinity resins as concanavalin A-agarose, heparin-Toyopearl or Cibacrom blue 3GA Sepharose B; or by hydrophobic interaction chromatography using such resins as phenyl ether, butyl ether, or propyl ether; or by immunoaffinity chromatography. Finally, one or more reverse-phase high performance liquid chromatography (RP-HPLC) steps employing hydrophobic RP-HPLC media, e.g., silica gel having pendant methyl or other aliphatic groups, can be employed to further purify the protein of the invention.

Affinity columns including antibodies to the protein of the invention can also be used in purification in accordance with known methods. Some or all of the foregoing purification steps, in various combinations or with other known methods, can also be employed to provide a substantially purified isolated recombinant protein. Preferably, the isolated protein of the invention is purified so that it is substantially free of other mammalian proteins.

It is thus also an aspect of the invention to provide a method for producing a recombinant HGyV protein or a CPP fusion protein of the invention. According to a particular embodiment, the method of the invention comprises the steps of:

(a) introducing a nucleic acid encoding the recombinant HGyV protein or a CPP fusion protein into one of the host cell described above;

(b) growing the transfected host cell to produce the said HGyV protein or CPP fusion protein; and (c) isolating the recombinant HGyV protein or CPP fusion protein from the host cell.

Proteins of the invention may be used to screen for agents which are capable of binding to the said protein. Binding assays using a desired binding protein, immobilized or not, are well known in the art and may be used for this purpose using the protein of the invention. Purified cell based or protein based (cell free) screening assays may be used to identify such agents. For example, H-apoptin may be immobilized in purified form on a carrier and binding or potential ligands to purified H-apoptin may be measured.

The CAV-encoded A-apoptin has been shown to induce apoptosis in a tumor cells, but not in wild-type cells (Danen-van Oorschot et al., *Proc. Natl. Acad. Sci. U.S.A.,* 94: 5843-5847, 1997). Preclinical studies with A-apoptin showed that gene transfer into tumor cells, using virus methods including viral transfer, either in cell culture or in vivo, led to the rapid death of cells, and that this effect was specific for the tumor cells. For example, in vivo adenovirus-mediated delivery of A-apoptin was efficient against a primary squamous cell carcinoma as a model of head and neck cancers (Schloop et al., *Cancer Biol Ther,* 7(9): 1368-1373, 2008; Schloop et al., *J Mol Histol,* 40(3): 177-81, 2009). A-apoptin sensitizes the activation of apoptosis in radioresistant tumor SQD9 cells, resulting in an additive cytotoxic effect of irradiation and apoptin (Olijslagers et al., *Basic Clin Pharmacol Toxicol,* 100(2): 127-131, 2007). Also, liver, cervix and gastric and hepatocarcinoma carcinoma xenografts treated with A-apoptin exhibited a significant tumor growth inhibition in vivo (Sun et al., *Int. J. Cancer,* 124: 2973-2981, 2009).

The apoptosis-inducing activity of A-apoptin is associated with its nuclear localization, which has been shown to be dependent upon specific motifs found in the protein, e.g. the NLS and NES sequences, the LRS domain, and the phosphorylation site. Since these elements are also found in the sequence of H-apoptin, the said H-apoptin behaves like the CAV protein and thus has pro-apoptotic activity in tumor cells only.

In another aspect, the invention thus relates to a pharmaceutical composition comprising a protein or fusion protein of the invention, purified from cells or recombinantly produced, combined with a pharmaceutically acceptable carrier. Advantageously, H-apoptin is used as a pharmaceutical composition, because of its pro-apoptotic activity in tumor cells. Even more advantageously, CPP-H-apoptin is used as a pharmaceutical composition, because of its facilitated delivery to the tumor cells. In this case, the H-apoptin protein or CPP-H-apoptin fusion protein is administered directly to a subject in need thereof.

As an alternative, it is possible to administer the H-apoptin gene of the invention to the said subject using gene therapy techniques. In this case, the pharmaceutical composition of the invention may contain the HGyV virus. Alternatively, the pharmaceutical composition of the invention may comprise the H-apoptin gene carried by a vector suitable for administration to a patient. Such vectors may be either derived from a virus or from a non-viral origin.

Non-viral vectors include plasmids. Such a plasmid may be a conditionally replicating plasmid that is incapable of replicating in the patients for safety reasons. These plasmids may be based on the plasmids described in the patent PCT applications WO 97/10343 and WO 2009/027351. Naked plasmid DNA can be directly injected into muscle cells (Wolff et al, *Science,* 247: 1465-1468, 1990) or attached to gold particles that are bombarded into the tissue (Cheng et al, *Proc. Natl. Acad. Sci. U.S.A.,* 90: 4455-4459, 1993). Though not very efficient, this can result in prolonged low level expression in vivo. The plasmid DNA can also be transfected into the cell with the use of non-viral gene delivery vectors, termed "self-assembled" systems, based on cationic molecules, which form spontaneous complexes with negatively charged nucleic acids (Eliyahu et al., *Molecules,* 10: 34-64, 2005).

In another aspect of the invention, the vector is a viral vector. By replacing genes that are needed for the replication phase of the virus life cycle (the non-essential genes) with foreign genes of interest, the recombinant viral vectors can transduce the cell type it would normally infect. To produce such recombinant viral vectors the non-essential genes are provided in trans, either integrated into the genome of the packaging cell line or on a plasmid. Several vectors based on viruses such as adenovirus, adeno-associated virus (AAV), lentivirus, or herpes simplex virus 1 (HSV1), are available for gene therapy. All of them are encompassed within this invention.

Adenoviral vectors are currently the most frequently used viral vectors in gene therapy in humans. So-called third-generation (or "gutless") adenoviral vectors (Lindermann and Schnittler, *Thromb. Haemost.,* 102: 1135-1143, 2009) are preferred for use in the present invention. Said vectors need not be detailed here, since the skilled person is fully aware of the characteristics and uses of said adenoviral vectors.

Alternatively the skilled person may use a lentiviral vector to deliver the H-apoptin of the invention. Preferentially, the said lentiviral is a self-inactivating (SIN) lentivirus. In a further preferred embodiment, the lentiviral vector genome comprises, as an inserted cis-acting fragment, at least one polynucleotide consisting in the DNA flap (Zennou et al., *Cell,* 101: 173-185, 2000; WO 99/55892; WO 01/27304; WO 2009/019612) or containing such DNA flap. In a particular embodiment, the DNA flap is inserted upstream of the polynucleotide of interest, advantageously but not necessarily to be located in an approximate central position in the vector genome. Nevertheless, any lentiviral vector can be used in the context of the present invention. The construction and the manipulation of lentiviral vectors are well known to the skilled person.

The preferred viral vectors according to the invention are based on adenoviral-associated virus or AAV. Amongst the 8 serotypes, the AAV used for treating a neuromuscular disease according to the invention is preferentially an AAV1, i.e. its capsid is of the serotype 1. AAV1 has been shown to be the most efficient for muscle cells transduction. On the other hand, the sequences of a viral origin, and in particular the ITRs, associated to the transgene are preferably of AAV2 origin. The resulting AAV-based vector of the invention has, preferentially, a 2/1 pseudotype. The skilled person will easily realize, however, that the invention is not restricted to this particular vector; in fact, all AAV serotypes are equally suited for use in this invention. For example, AAV6, AAV8 or AAV9 also effectively transduce striated muscle cells, while AAV5 is highly efficient in transducing neural cells in the brain (Markakis et al., *Molecular Therapy,* 18: 588-593, 2010); all of them can therefore be used successfully in the context of the invention. Like adenoviral and lentiviral vectors, the AAV-based vectors have already been used extensively by the skilled person for gene therapy purposes (see e.g. Michelfelder and Trepel, *Adv Genet.,* 67: 29-60, 2009); there is thus no need for detailing methods for constructing and using the said AAV vectors.

The pharmaceutical composition of the invention may contain, in addition to the carrier and H-apoptin or CPP-H-apoptin protein or gene or HGyV virus, various diluents, fillers, salts, buffers, stabilizers, solubilizers, and other materials well known in the art.

As used herein, "pharmaceutically acceptable carrier" includes any and all solvents, buffers, salt solutions, dispersion media, coatings, antibacterial and antifungal agents, isotonic and absorption delaying agents, and the like that are physiologically compatible. The type of carrier can be selected based upon the intended route of administration. In various embodiments, the carrier is suitable for intravenous, intraperitoneal, subcutaneous, intramuscular, topical, transdermal or oral administration. Pharmaceutically acceptable carriers include sterile aqueous solutions or dispersions and sterile powders for the extemporaneous preparation of sterile injectable solutions or dispersion. The use of media and agents for pharmaceutically active substances is well known in the art. As detailed herebelow, additional active compounds can also be incorporated into the compositions, such as anti-cancer and/or anti-angiogenesis agents; in particular, the additional active compound can be an anti-angiogenic agent, a chemotherapeutic agent, or a low-molecular weight agent. A typical pharmaceutical composition for intravenous infusion could be made up to contain 250 ml of sterile Ringer's solution, and 100 mg of the combination. Actual methods for preparing parenterally administrable compounds will be known or apparent to those skilled in the art and are described in more detail in for example, Remington's Pharmaceutical Science, 17th ed., Mack Publishing Company, Easton, Pa. (1985), and the $18^{th}$ and $19^{th}$ editions thereof, which are incorporated herein by reference.

H-apoptin or CPP-H-apoptin protein or gene or HGyV virus in the composition preferably is formulated in an effective amount. An "effective amount" refers to an amount effective, at dosages and for periods of time necessary, to achieve the desired result, such as induction of apoptosis in tumor cells. A "therapeutically effective amount" means an amount sufficient to influence the therapeutic course of a particular disease state. A therapeutically effective amount is also one in which any toxic or detrimental effects of the agent are outweighed by the therapeutically beneficial effects.

For therapeutic applications, the H-apoptin or CPP-H-apoptin protein or gene or HGyV virus of the invention is administered to a mammal, preferably a human, in a pharmaceutically acceptable dosage form such as those discussed above, including those that may be administered to a human intravenously as a bolus or by continuous infusion over a period of time, by intramuscular, intraperitoneal, intracerebrospinal, subcutaneous, intraarticular, intrasynovial, intrathecal, oral, topical, or inhalation routes. The H-apoptin or CPP-H-apoptin protein is also suitably administered by intratumoral, peritumoral, intralesional, or perilesional routes, to exert local as well as systemic therapeutic effects. The intraperitoneal route is expected to be particularly useful, for example, in the treatment of ovarian tumors.

Dosage regimens may be adjusted to provide the optimum response. For example, a single bolus may be administered, several divided doses may be administered over time, or the dose may be proportionally reduced or increased. The compositions of the invention can be administered to a subject to effect cell growth activity in a subject. As used herein, the term "subject" is intended to include living organisms in which apoptosis can be induced, and specifically includes mammals, such as rabbits, dogs, cats, mice, rats, monkey transgenic species thereof, and preferably humans.

The H-apoptin protein encoded by the H-VP3 gene of the invention has therapeutic properties, because of its apoptotic activity in tumor cells. The invention thus also relates to the H-apoptin or CPP-H-apoptin protein or gene or HGyV virus as a medicament. More specifically, the H-apoptin or CPP-H-apoptin protein or gene or HGyV virus and the pharmaceutical compositions of the invention are useful in the treatment or prevention of a variety of cancers, including (but not limited to) the following: carcinoma, including that of the bladder, breast, colon, head and neck, kidney, including renal cell carcinoma, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Burkitt's lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyosarcoma, and osteosarcoma; and other tumors, including melanoma, xeroderma pigmentosum, keratoactanthoma, seminoma, thyroid follicular cancer and teratocarcinoma, and other cancers yet to be determined. In a preferred embodiment, the H-apoptin protein of the invention is used to treat melanoma, leukemia, renal cancer, colon cancer, ovarian cancer, prostate cancer, lung cancer, bladder cancer, breast cancer, or head and neck cancer.

The present invention thus relates to the H-apoptin or CPP-H-apoptin protein or gene or HGyV virus described above for use in treating or inhibiting cancer-related diseases in a subject. It is an aspect or object of the present invention to provide a method of treating diseases and processes that result from cancer cell proliferation, and a composition for treating or repressing the growth of a cancer by induction of apoptosis. Yet another aspect of the invention is to provide compositions and methods useful for gene therapy for the modulation of cancer. The method of the present invention may be used in particular for the treatment of melanoma, leukemia, renal cancer, colon cancer, ovarian cancer, prostate cancer, lung cancer, bladder cancer, breast cancer, or head and neck cancer.

The present invention also includes kits, e.g., comprising one or more described H-apoptin or CPP-H-apoptin protein and/or gene and/or HGyV virus and instructions for the use of the said H-apoptin or CPP-H-apoptin protein and/or gene and/or HGyV virus for treating cancer. The instructions may include directions for using the H-apoptin or CPP-H-apoptin protein and/or gene and/or HGyV virus in vitro, in vivo or ex vivo. Typically, the kit will have a compartment containing the H-apoptin or CPP-H-apoptin protein and/or gene and/or HGyV virus. The H-apoptin or CPP-H-apoptin protein and/or gene and/or HGyV virus may be in a lyophilized form, liquid form, or other form amendable to being included in a kit. The kit may also contain additional elements needed to practice the method described on the instructions in the kit, such a sterilized solution for reconstituting a lyophilized powder, additional agents for combining with the H-apoptin or CPP-H-apoptin protein and/or gene and/or HGyV virus prior to administering to a patient, and tools that aid in administering the H-apoptin or CPP-H-apoptin protein and/or vector to a patient.

The effectiveness of the H-apoptin or CPP-H-apoptin protein and/or gene and/or HGyV virus in preventing or treating disease may be improved by administering said protein or gene serially or in combination with another agent that is effective for those purposes, such as one or more conventional therapeutic agents such as, for example, alkylating agents, folic acid antagonists, anti-metabolites of nucleic acid metabolism, antibiotics, pyrimidine analogs, 5-fluorouracil, cisplatin, purine nucleosides, amines, amino acids, triazol nucleosides, or corticosteroids. In another aspect of the invention, the administration is combined with an administration of therapeutically effective amount of chemotherapeutic agent, such as for example, taxol (paclitaxel) or taxotere (docetaxel).

Chemotherapeutic agents include without any limitations, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and antifolate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; and cell cycle signaling inhibitors. In addition, the methods of the invention can be combined with another anti-cancer treatment, anti-angiogenic agent, or chemotherapeutic agent or radiation therapy. A preferred example is docetaxel or taxotere. Other examples include, gemcitabine, cisplatin diterpenoids and vinca alkaloids, paclitaxel, vinblastine, vincristine, and vinorelbine, carboplatin, cyclophosphamide, melphalan, and chlorambucil, busulfan, carmustine, dacarbazine, cyclophosphamide, melphalan, chlorambucil, busulfan, carmustine, dacarbazine, anti-neoplastic agents including, but not limited to, actinomycins such as dactinomycin, anthrocyclins such as daunorubicin and doxorubicin, bleomycins, epipodophyllotoxins, etoposide and teniposide; antimetabolite neoplastic agents, 5-fluorouracil, methotrexate, cytarabine, mecaptopurine, thioguanine, camptothecins, irinotecan HCl, and topotecan HCl.

A variety of different chemotherapeutic agents or anti-cancer polypeptides can also be selected. Information sources such as www.clinicaltrials.gov, vww.ncbi.nlm.nih, and www.druqs.com, include references to polypeptides and agents that can be selected.

Such other agents, e.g. anti-angiogenic agents or chemotherapeutic agents may be present in the composition being administered or may be administered separately. In one aspect of the invention, the administration is performed with the other active principle, either simultaneously, separately or sequentially over time. When the administration is performed simultaneously, the two active principles may be combined in a single pharmaceutical composition, comprising the two compositions, such as a tablet or a gel capsule. On the other hand, the two active principles may, whether or not they are administered simultaneously, be present in separate pharmaceutical compositions. To this end, the combination may be in the form of a kit comprising, on the one hand, the H-apoptin or CPP-H-apoptin protein and/or a H-apoptin-encoding vector, including HGyV, as described above and, on the other hand, the second active principle, the H-apoptin or CPP-H-apoptin protein and/or a H-apoptin-encoding vector as described above and the second active principle being in separate compartments and being intended to be administered simultaneously, separately, or sequentially over time.

The combination according to the present invention can be administered especially for tumor therapy in combination with chemotherapy, protein therapy (i.e. using a therapeutic agent such as an antibody or recombinant protein), gene therapy, radiotherapy, immunotherapy, surgical intervention, or a combination of these. Long-term therapy is equally possible as is adjuvant therapy in the context of other treatment strategies, as described above.

The examples that follow are merely exemplary of the scope of this invention and content of this disclosure. One skilled in the art can devise and construct numerous modifications to the examples listed below without departing from the scope of this invention.

FIGURE LEGENDS

FIG. 1: Nucleotide sequence of HGyV and principal features. Principal features are described by homology with the annotated sequence of CAV (accession number M55918)

FIG. 2: Nucleotide alignment between CAV and HGyV. HGyV was aligned with the CAV sequence (accession number M55918) using the CLC program. The consensus sequence (SEQ ID NO: 18).

Figure 3:
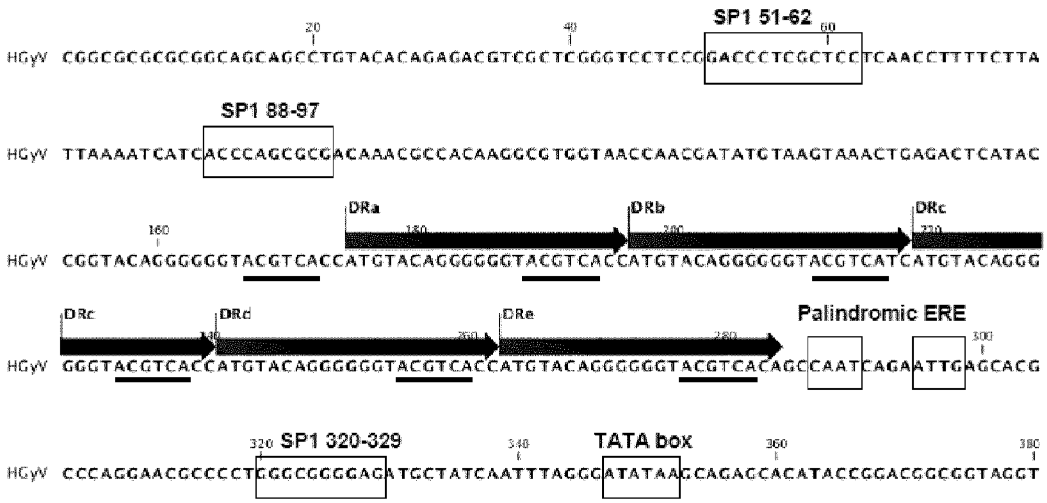

FIG. 3: Nucleotide sequence of the promoter region of HGyV (SEQ ID NO: 15 and principal features (see text). Direct repeats (DRa to DRe) of 22 nt are shown with putative estrogen responsive elements ACGTCA (SEQ ID NO.: 31) that are underlined. Putative SP1 sites are depicted. The palindromic CAAT CAGA ATTG (SEQ ID NO: 17) possible estrogen responsive element is depicted.

Figure 4:
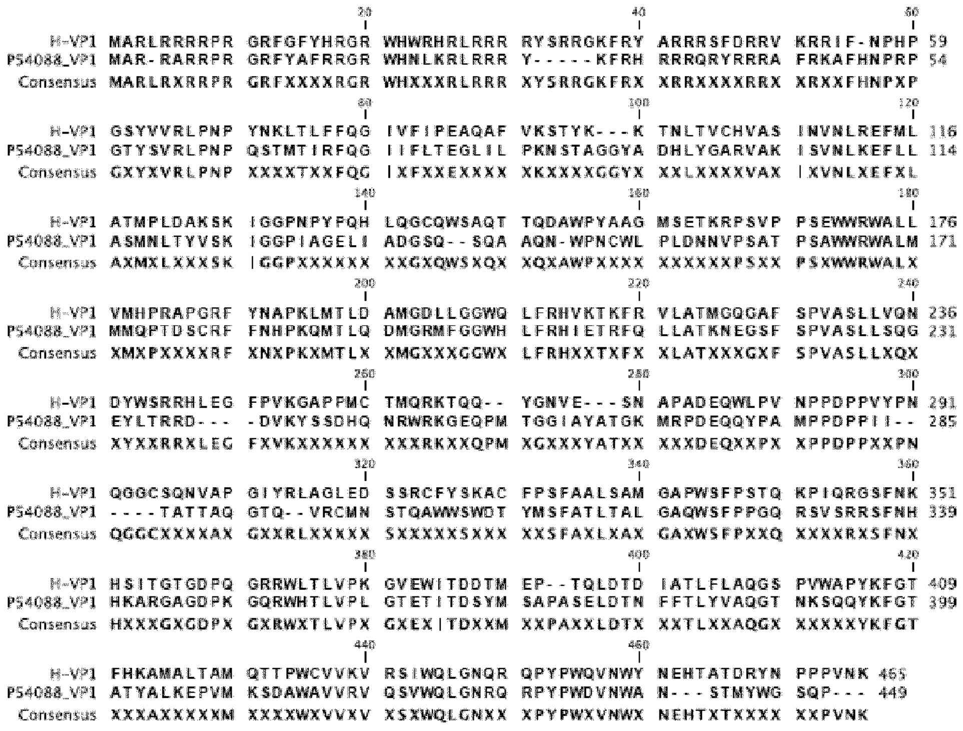

FIG. 4: Comparison between CAV and HGyV VP1 at the amino acids level. HGyV VP1 was aligned with its CAV homolog (accession number P54088) using the CLC program. The consensus sequence (SEQ ID NO: 36).

FIG. 5: Comparison between CAV and HGyV VP2 at the amino acids level. HGyV VP1 was aligned with its CAV homolog (accession number P69485) using the CLC program. The consensus sequence (SEQ ID NO: 20).

FIG. 6: Comparison between CAV and HGyV apoptin at the amino acids level. HGyV apoptin was aligned with its CAV homolog (accession number P54094) using the CLC program. Principal domains of the A-apoptin protein are shown (LRS: leucine rich domain, NLS 1 and 2: Nuclear localization signal, NES: putative nuclear exportation signal). The amino acid Thr in position 108 of A-apoptin is depicted by a red arrow. The phosphorylation site at amino acid Thr-111 of H-apoptin predicted by the Netphos program (www.cbs.dtu.dk/services/NetPhos/) is also shown.

EXPERIMENTAL EXAMPLES

Isolation and Sequencing of HGyV

DNA samples extracted with an automatic EasyMag apparatus (BioMérieux, Marcy l'Etoile, France) from cutaneous swabs taken from healthy people were screened and amplified by the bacteriophage phi29 polymerase based multiple displacement amplification (MDA) assay using random primers. The reaction was performed essentially with the REPLI-g Midi kit (Qiagen) according to the manufacturer's instructions. This provides concateners of high molecular weight DNA.

Sequencing was conducted by an Illumina High Seq sequencer: 5 μg of high molecular weight DNA resulting from isothermal amplification were fragmented into 200 to 350 nt fragments, to which were ligated adapters; 7588712 reads of 100 nt were derived from the sample.

Sorting out the flow of Illumina sequences was first done by a subtractive database comparison procedure. To this end, the whole host genome sequence (NCBI build 37.1/assembly hg19) was scanned with the reads using SOAPaligner (remaining: 4664094 reads). A quick and very restrictive BLASTN study was also performed to eliminate additional host reads (remaining: 4469243 reads). The best parameters to be used have been determined previously. A number of assembly programs dedicated to short or medium-sized reads (Velvet, SOAPdenovo, CLC) have been tested for their efficiency in our pipeline. Optimal parameters have been set. The comparison of the single reads and contigs with already known genomic and taxonomic data was done on dedicated specialized viral, bacterial and generalist databases maintained locally (GenBank viral and bacterial databases, nr). The aforementioned databases were scanned using BLASTN and BLASTX. Binning (or taxonomic assignment) was based on the lowest common ancestor from the best hits among reads with a significant e-value.

Among different contigs found harboring a size compatible with a viral genome, a contig of 2315 nt was more deeply analyzed because it showed some homology with the members of the Circoviridae family and more specifically with the only known member of the genus Gyrovirus, i.e. the Chicken Anemia Virus (CAV). Although CAV was described and isolated more than 30 years ago in chicken showing severe anemia (Yuasa et al., *Avian Dis*, 23: 366-385, 1979), no homolog virus is currently known in humans and thus this result was unexpected. We thus conducted detailed analysis, which showed that this contig corresponded to the full or quasi full length-genome of a new virus species we have named HGyV (Human Gyrovirus), on the basis of the characteristics shown below.

Based on the sequence of this contig, we have defined a set of primers (Table 1) and confirmed the sequence of the whole genome by the Sanger method. The resulting sequence is presented in FIG. 1, which also presents its principal features. Alignment of the whole genome with that of CAV is depicted in FIG. 2. The overall nucleotide identity between the two genomes is low: in the zone of maximal homology, between nt 100 and 700 (CAV accession number M55918), the overall homology is around 70%.

This virus shares the general organization of the CAV genome. It contains:

- a 5' region with the general features of the CAV promoter/enhancer (Miller et al., *J. Virol.*, 79(5): 2859-2868, 2005) (see FIG. 3): like the CAV promoter, it includes repeated regions of 22 nt which were designated DRa to DRe. Like in CAV, the DR regions contain the sequence ACGTCA (AGCTCA in CAV), which both vary by one nucleotide from the estrogen response element (ERE) half site, (A)GGTCA. In fact, there is also one less conserved repetition just upstream of DRa (SEQ ID NO: 16: C/A G/T GTACAGGGGGGTACGTCA T/C C/A, position nt 153-174, that also contains the ACGTCA sequence, not shown in FIG. 3). In HGyV, these DRs are repeated without any space between them. In CAV, these repeats are in the number of 4 to 5 in function of the strains and are separated by insert sequences of 15 bp between the first two or three and the last two. This is not the case for HGyV. We did not evidence the Estrogen Responsive Elements (ERE) found around nt 50 in CAV; nevertheless, we found downstream of DRd a palindromic sequence (CAATCAGAATTG) (SEQ ID NO: 17) which could reveal similar characteristics: in fact ERE generally consists of pentamer or hexamers (A)GGTCA separated by a 2-3 by insert, but this consensus could vary widely (Aumais et al., *J Biol Chem,* 271: 12568-12577, 1996). We have identified Transcription factor binding sites with the help of the programs TFSEARCH and TFBIND. As in CAV several SP1 sites were found (see FIG. 3).

three partially overlapping open reading frames corresponding to different proteins. We have used the names of the CAV counterparts (see details in Table 2). For reason of clarity we have named the CAV protein "avian proteins" (a-proteins) and the HGyV counterpart "human proteins" (h-proteins):

VP1, the protein of nucleocapsid: the alignment of h-VP1 and a-VP1 is shown in FIG. 4.

VP2, the phosphatase: the alignment of h-VP2 with a-VP2 is shown in FIG. 5.

VP3, the non-structural protein, referred in CAV as apoptin. The alignment of H-apoptin with A-apoptin is shown in FIG. 6, together with the domains of A-apoptin that have been shown to be important in functions (review in Los et al., *Biochim Biophys Acta,* 1793(8): 1335-1342, 2009). The overall similarity with A-apoptin is low (less than 40%).

The A-apoptin alone can induce apoptosis in a broad range of transformed and cancer cells but not in non-transformed or primary cells (for a review see Los et al., *Biochim Biophys Acta,* 1793(8): 1335-1342, 2009). It induces the apoptosis by a mechanism implicating the mitochondrial (intrinsic) pathway and is thus independent of the death receptor (extrinsic) pathway. As shown in FIG. 5, the so-called Leucine Rich Stretch seems conserved with a high contents of hydrophobic aliphatic leucine or isoleucine aa. This region seems to interact with different cellular proteins that seem important for its functions (summarized in Los et al., *Biochim Biophys Acta,* 1793(8): 1335-1342, 2009). One of the NLS signal (NLS2) seems also conserved, together with the putative nuclear exportation signal (NES). Importantly, the Netphos 2.0 server predicts a phosphorylation site at position 110, which is located between NLS2 and NES and seems homolog to position Thr-108 of A-apoptin. In fact nuclear accumulation of A-apoptin, which is important for its pro-apoptotic activity, is dependent on the phosphorylation of Thr-108. This phosphorylation is mediated by a kinase active in tumors and transformed cells but not in normal cells.

TABLE 1 primers used for resequencing the HGyV genome with the method of Sanger

| Primer sequence (5'→3') Forward | Reverse | Expected size (bp) |
|---|---|---|
| SEQ ID NO: 21: 5'-tccgttgcagtgtgctcgttg-3' | SEQ ID NO: 22: 5'-gcacttagagggcttcccag-3' | 642 |
| SEQ ID NO: 23: 5'-ctcatctgccggtgcattgg-3' | SEQ ID NO: 24: 5'-ccgggctcctatgtggtaag-3' | 654 |
| SEQ ID NO: 25: 5'-aaagcttgagcctccggaatg-3' | SEQ ID NO: 26: 5'-taggcaagaggggcaacttgg-3' | 698 |
| SEQ ID NO: 27: 5'-tagttgttgctcgtcggcgag-3' | SEQ ID NO: 28: 5'-ctttcaccacgcaccaaggg-3' | 711 |

TABLE 2

Nucleotide positions in the HGyV genome of the three main open reading frames. HGyV Open Reading Frames

| ORF | Position Start | Position End |
|---|---|---|
| H-apoptin | 508 | 882 |
| H-VP1 | 884 | 2281 |
| H-VP2 | 381 | 1076 |

Replication of HGyV in Human Cells

Because of the high homology of HGyV with CAV, it was investigated whether HGyV can replicate in human cells. CAV is known not to be capable of such replication.

Cloning of the HGyV Virus

From the high molecular weight DNA resulting from isothermal amplification from the same swab sample, a full length genome of HGyV was amplified, using the following primers:

HGyV.12F (SEQ ID NO: 51): GAAAGCGCTGCAAAGCTGGGG

HGyV.12R (SEQ ID NO: 52): TGCAGCGCTTTCTGCTATGGG

The genome was cloned in the plasmid PCR2.1 (Invitrogen, TA cloning kit) so as Eco47III sites were located at both sides of the genome. We have named this molecular clone HGyV-PTQ1 and generated its sequence by Sanger sequencing. This sequence, represented by SEQ ID NO.: 37, is identical to the prototypal HGyV sequence, excepted for an insertion of 60 nt between positions 2263 et 2264 of the sequence represented by SEQ ID NO.: 1. This insertion introduces a stop codon, leading to the deletion of 5 amino acids at the C-term part of VP1 (SEQ ID NO.: 39).

Preparation of Circularized HGyV DNA Genome.

Plasmid DNA from HGyV-PTQ1 containing the complete HGyV DNA genome (30 μg) was digested with Eco47III and self-ligated by T4 DNA ligase treatment to circularize the genome (DNA was diluted at 10 ng/μL in order to favor intramolecular ligation). Ligation products were analyzed on a 0.8% agarose gel.

Electroporation Transfection.

Two clones of the lymphoblastoid cell line JURKAT (E6.1 and J77.20) were cotransfected by the Neon Transfection System (Invitrogen) using 3 μg of circularized HGyV DNA in addition to 7 μg of pEGFP-N1 (a plasmid expressing the Green Fluorescent Protein, Clontech Laboratories) allowing for estimating the transfection efficiency. At 48 h after transfection, medium was removed and replaced by new medium in order to reduce the amount of free-non-transfected DNA. Serials passages were made every three days and $2\times10^6$ cells were collected every time for detecting the presence of intracellular HGyV mRNAs. Cells from passage 4 to 7 were analyzed by extraction of total RNA and RT-PCR using the following primers, targeting respectively the VP1 and the VP2 protein:

```
HGyV-VP1-F2q (SEQ ID NO: 53):
TGCTTGCAACAATGCCTTTAGA

HGyV-VP1-R2q (SEQ ID NO: 54):
CGCTGGGTCTTTTTGTTTCTG

HGyV-VP2-F3q (SEQ ID NO: 55):
GGCATACGAGCATCCAACAA

HGyV-VP2-R3q (SEQ ID NO: 56):
TCGTCCGCAGGTGCAGAT
```

VP1 and the VP2 transcripts were detected in the cells. No PCR amplification was obtained in controls in which the reverse transcription step (RT) was omitted, which demonstrates that RNAs were evidenced and not residual amounts of genomic DNA. Because HGyV is a DNA virus, the sustained presence of HGyV RNAs during seven passages is a demonstration of viral replication. The maximum amount of these transcripts was obtained at the $6^{th}$ passage. No transcript of VP1 or VP2 was detected in non-transfected cells.

In Vivo Inhibition of Tumor Growth by PTD4-H-Apoptin Protein Fusion

Expression of Avian and Human Apoptins:

Fusion proteins were constructed by inserting a protein transduction domain (PTD) based on the PTD4 domain described by Ho et al (*Cancer Res,* 61(2): 474-477, 2001), at the N-terminus of the apoptin protein, in order to facilitate apoptin entry into cells. A GGSGGS linker was inserted between the PTD domain and the apoptin moiety. The same constructions were made for H-apoptin and A-apoptin, with the goal of comparing the activity of H-apoptin with A-apoptin (Sun et al., *Int J Cancer,* 124(12): 2973-2981, 2009).

The following fusion proteins were designed:

```
PTD GGSGGS-H-apoptin
                                       (SEQ ID NO: 58)
ARAAAAQARAGGSGGSTPRSRRRATTTQSELLTAYEHPTSSSPPAET
TSIEIQIGIGSTIITLSLPGYASVRVLTTRSAPADDGGVTGSRRLVD
LSHRRPRRTSSPEIYVGFAAKEKQQKENLITLRENGPPIKKLRL*
```

-continued

```
PTD-GGSGGS-A-apoptin
                                       (SEQ ID NO: 60)
ARAAAAQARAGGSGGSNALQEDTPPGPSTVFRPPTSSRPLETPHCRE
IRIGIAGITITLSLCGCANARAPTLRSATADNSESTGFKNVPDLRTD
QPKPPSKKRSCDPSEYRVSELKESLITTTPSRPRTARRCIRL*
```

The genes were synthesized following codon optimisation (GeneArt AG, Regensburg, Germany) for production in *E. coli*. Negative cis-acting sites (such as splice sites, TATA-boxes, etc.) which may negatively influence expression were eliminated wherever possible. GC content was adjusted to prolong mRNA half-life. Codon usage was adapted to the bias of *Escherichia coli*. In addition, a 5' NheI and a 3' BamHI restriction sites were introduced. The resulting genes have the sequences represented by SEQ ID NOs: 57 and 58, respectively.

Each gene was cloned in the NheI and BamHI sites of the plasmid pET-28, downstream of the His-tag sequence. Both proteins were expressed and purified from *E. coli* using standard procedures either from the soluble or non-soluble fraction.

PTD-Apoptin Protein Induces Cell Death in Tumor Cells.

In order to test the pro-apoptotic activity of each fusion protein, the tumor cytotoxicity of PTD GGSGGS-H-apoptin and PTD GGSGGS-A-apoptin is determined in vitro on tumor primary cells isolated from a melanoma cancer xenograft model. The said tumor cells are responsive to adriamycin but not to 5-FU.

A primary cell culture is obtained from a frozen stock of explanted and dissociated xenografts. After thawing, cells are grown in complete growth medium (F12/DMEM supplemented with 8% fetal bovine serum, 100 μg/ml penicillin G sodium, 100 μg/ml streptomycin sulphate). After centrifugation and resuspension in complete growth medium, the cells are plated at a density of ca. 140 000 cells/$cm^2$ in 75 $cm^2$ cell culture flasks and maintained at 37° C. in a humidified atmosphere with 5% $CO_2$ for at least one week. Then, the cells are harvested and seeded in 96-wells plates at a density of $2.5\times10^3$ cells/well for cytotoxicity assays. Cells are incubated 48 h at 37° C. prior to addition of the test molecules and selected comparison compounds and vehicle.

Test drugs are added at desired final concentrations and further incubated for 72 hr.

Cell viability is assessed before drugs' addition (TO) and 72 hrs. after drugs' addition by measuring ATP cell content using CellTiter-Glo® Luminescent Cell Viability Assay (Promega) according to the manufacturer's instructions. Luciferase activity is measured on a luminometer (PerkinElmer® EnVision™)

Each of the fusion protein is diluted in DMEM/F12 medium at the following concentrations: 1000 nM; 333.33 nM; 111.11 nM; 37.04 nM; 12.35 nM; 4.12 nM; 1.37 nM; 0.46 nM; 0.15 nM; and 0.05 nM. Each concentration of the 2 compounds is tested in triplicate and three different experiments are performed. In addition, a positive control (adriamycin) as well as a negative control (vehicle alone) is included in the experiment.

The $IC_{50}$ is the concentration of drug that inhibits cell viability by 50%. Cell viability is calculated as a percentage of ATP value compared to vehicle-treated controls. $IC_{50}$ is determined for each measurement using GraphPad Prism software. $IC_{50}$ determination demonstrates conclusively that the PTD GGSGGS-H-apoptin fusion protein shows at least equivalent or superior activity than the corresponding avian fusion protein.

The invention claimed is:

1. A recombinant fusion protein comprising a cell penetrating peptide (CPP), a linker, and a polypeptide comprising a sequence at least 80% identical to SEQ ID NO: 7.

2. The recombinant fusion protein of claim 1, wherein the CPP comprises the amino acid sequence of SEQ ID NO: 40.

3. The recombinant fusion protein of claim 1, wherein the CPP comprises the amino acid sequence of SEQ ID NO: 41.

4. The recombinant fusion protein of claim 1, wherein the CPP comprises the amino acid sequence of SEQ ID NO: 42.

5. The recombinant fusion protein of claim 1, wherein the CPP comprises the amino acid sequence of SEQ ID NO: 43.

6. The recombinant fusion protein of claim 1, wherein the CPP comprises the amino acid sequence of SEQ ID NO: 44.

7. The recombinant fusion protein of claim 1, wherein the CPP comprises the amino acid sequence of SEQ ID NO: 45.

8. The recombinant fusion protein of claim 1, wherein the CPP comprises the amino acid sequence of SEQ ID NO: 46.

9. The recombinant fusion protein of claim 1, wherein the CPP comprises the amino acid sequence of SEQ ID NO: 47.

10. The recombinant fusion protein of claim 1, wherein the CPP comprises the amino acid sequence of SEQ ID NO: 48.

11. The recombinant fusion protein of claim 1, wherein the CPP comprises the amino acid sequence of SEQ ID NO: 49.

12. The recombinant fusion protein of claim 1, wherein the linker comprises the amino acid sequence represented by SEQ ID NO: 50.

13. The recombinant fusion protein of claim 1, wherein the recombinant fusion protein comprises the amino acid sequence represented by SEQ ID NO: 58.

14. The recombinant fusion protein of claim 1, wherein the recombinant fusion protein is encoded by the sequence represented by SEQ ID NO. 57.

* * * * *

SEQUENCE LISTING

<160> NUMBER OF SEQ ID NOS: 60

<210> SEQ ID NO 1
<211> LENGTH: 2315
<212> TYPE: DNA
<213> ORGANISM: artificial
<220> FEATURE:
<223> OTHER INFORMATION: HGyV

<400> SEQUENCE: 1

```
cggcgcgcgc ggcagcagcc tgtacacaga gacgtcgctc gggtcctccg gaccctcgct     60
cctcaacctt ttcttattaa aatcatcacc cagcgcgaca aacgccacaa ggcgtggtaa    120
ccaacgatat gtaagtaaac tgagactcat accggtacag gggggtacgt caccatgtac    180
aggggggtac gtcaccatgt acaggggggt acgtcatcat gtacaggggg gtacgtcacc    240
atgtacaggg gggtacgtca ccatgtacag gggggtacgt cacagccaat cagaattgag    300
cacgcccagg aacgcccctg ggcggggaga tgctatcaat ttagggatat aagcagagca    360
cataccggac ggcggtaggt atgtcatccg gcggtctcgg ggattgcagc gcctgtgaga    420
accgagccgc tgggggcagt gaattgccgc ttaggcaaga ggggcaactt gggcccagcg    480
gagccggatc cacgggcaag acactaaatg cagacccccc gctctcgccg acgagcaaca    540
actactcagt cagaactatt aacggcatac gagcatccaa caagttcgtc tccgccagca    600
gaaacgacct cgatagagat ccaaattggt atcgggtcaa ctataattac tctatcgcta    660
cctggctacg ccagtgtgcg cgttctcacg acgagatctg cacctgcgga cgatggagga    720
gtcactggtt ccaggaggct agtggacttg tcacacagga gacccagacg gaccagctcg    780
ccagagatct acgtcggctt cgccgcaaag gagaagcagc aaaaagaaaa cttgattacc    840
ttaagggaaa acggaccccc tataaaaaag ctaagactgt aacatggcaa gactacgaag    900
aagacgacct cgcggacgct ttggcttcta ccacagagga cgatggcact ggagacacag    960
actgcgacga agacgctatt cccggagggg taaatttcga tatgcgcgta gaagatcctt   1020
tgatcgccgc gttaagagga ggatcttcaa cccacacccg ggctcctatg tggtaaggct   1080
accgaaccct tacaataagc ttaccctctt tttccaaggc attgtattca ttccggaggc   1140
tcaagctttt gttaaaagca cctataaaaa gactaacctt acggtttgcc atgtagcctc   1200
cataaatgtt aacctccgag aatttatgct tgcaacaatg cctttagatg caaagagcaa   1260
aatcggaggc cctaaccctt atcctcagca cttgcagggg tgccaatggt cagcacaaac   1320
gacgcaggac gcatggccgt acgcagcggg catgtcagaa acaaaaagac ccagcgtacc   1380
accgagtgag tggtggcgct gggctctcct ggtgatgcac cctagagcac ctggcagatt   1440
ttacaatgcc ccaaagctaa tgactctgga cgctatggga gacctgttag gggctggca    1500
gctattcagg catgtaaaaa ccaagttcag agtgctagcg actatgggac aaggggcttt   1560
ctcaccagtt gcaagcctac ttgtacaaaa tgactactgg agcaggaggc acttagaggg   1620
cttcccagtt aaaggtgcac cacctatgtg caccatgcaa agaaaaactc agcagtacgg   1680
caacgtggag tccaatgcac cggcagatga gcaatggcta cccgtaaatc ccccagaccc   1740
accagtgtac ccaaaccagg gaggatgctc ccaaaacgtg gctccaggca tataccggct   1800
tgcaggctta gaagacagca gcagatgctt ttattcaaag gcttgtttcc ccagctttgc   1860
agcgctttct gctatgggtg caccctggtc atttcctagc actcaaaaac ctattcaaag   1920
aggctcattt aacaagcact ccatcacggg gacaggggac ccccagggcc gacggtggtt   1980
aacacttgtg cctaaaggag tcgagtggat tactgacgac accatggaac ctacgcaact   2040
```

```
ggacacagac attgcaacac tcttcttggc tcaaggcagt ccagtatggg caccctacaa   2100

attcggaact tttcacaaag cgatggcgct aacagcgatg cagaccaccc cttggtgcgt   2160

ggtgaaagtc cgttccatct ggcagctcgg caaccaaaga cagccgtacc catggcaagt   2220

gaactggtac aacgagcaca ctgcaacgga cagatacaac ccgccccccg tcaataaata   2280

attaaataaa ccaaatcgaa ttatttattt atttt                              2315
```

<210> SEQ ID NO 2
<211> LENGTH: 1379
<212> TYPE: DNA
<213> ORGANISM: artificial
<220> FEATURE:
<223> OTHER INFORMATION: H-VP1

<400> SEQUENCE: 2

```
atggcaagac tacgaagaag acgacctcgc ggacgctttg gcttctacca cagaggacga     60

tggcactgga gacacagact gcgacgaaga cgctattccc ggaggggtaa atttcgatat    120

gcgcgtagaa gatcctttga tcgccgcgtt aagaggagga tcttcaaccc acacccgggc    180

tcctatgtgg taaggctacc gaacccttac aataagctta ccctcttttt ccaaggcatt    240

gtattcattc cggaggctca agcttttgtt aaaagcacct ataaaaagac taaccttacg    300

gtttgccatg tagcctccat aaatgttaac ctccgagaat ttatgcttgc aacaatgcct    360

ttagatgcaa agagcaaaat cggaggccct aacccttatc ctcagcactt gcaggggtgc    420

caatggtcag cacaaacgac gcaggacgca tggccgtacg cagcgggcat gtcagaaaca    480

aaaagaccca gcgtaccacc gagtgagtgg tggcgctggg ctctcctggt gatgcaccct    540

agagcacctg gcagatttta caatgcccca aagctaatga ctctggacgc tatgggagac    600

ctgttagggg gctggcagct attcaggcat gtaaaaacca agttcagagt gctagcgact    660

atgggacaag ggctttctc accagttgca agcctacttg tacaaaatga ctactggagc     720

aggaggcact tagagggctt cccagttaaa ggtgcaccac ctatgtgcac catgcaaaga    780

aaaactcagc agtacggcaa cgtggagtcc aatgcaccgg cagatgagca atggctaccc    840

gtaaatcccc cagacccacc agtgtaccca aaccagggag gatgctccca aaacgtggct    900

ccaggcatat accggcttgc aggcttagaa gacagcagca gatgctttta ttcaaaggct    960

tgtttcccca gctttgcagc gctttctgct atgggtgcac cctggtcatt tcctagcact   1020

caaaaaccta ttcaaagagg ctcatttaac aagcactcca tcacggggac aggggacccc   1080

cagggccgac ggtggttaac acttgtgcct aaaggagtcg agtggattac tgacgacacc   1140

atggaaccta cgcaactgga cacagacatt gcaacactct tcttggctca aggcagtcca   1200

gtatgggcac cctacaaatt cggaactttt cacaaagcga tggcgctaac agcgatgcag   1260

accacccctt ggtgcgtggt gaaagtccgt tccatctggc agctcggcaa ccaaagacag   1320

ccgtacccat ggcaagtgaa ctggtacaac gagcacactg caacggacag atacaaccc    1379
```

<210> SEQ ID NO 3
<211> LENGTH: 459
<212> TYPE: PRT
<213> ORGANISM: artificial
<220> FEATURE:
<223> OTHER INFORMATION: H-VP1

<400> SEQUENCE: 3

```
Met Ala Arg Leu Arg Arg Arg Arg Pro Arg Gly Arg Phe Gly Phe Tyr
1               5                   10                  15
```

-continued

```
His Arg Gly Arg Trp His Trp Arg His Arg Leu Arg Arg Arg Arg Tyr
            20                  25                  30

Ser Arg Arg Gly Lys Phe Arg Tyr Ala Arg Arg Arg Ser Phe Asp Arg
        35                  40                  45

Arg Val Lys Arg Arg Ile Phe Asn Pro His Pro Gly Ser Tyr Val Val
    50                  55                  60

Arg Leu Pro Asn Pro Tyr Asn Lys Leu Thr Leu Phe Phe Gln Gly Ile
65                  70                  75                  80

Val Phe Ile Pro Glu Ala Gln Ala Phe Val Lys Ser Thr Tyr Lys Lys
                85                  90                  95

Thr Asn Leu Thr Val Cys His Val Ala Ser Ile Asn Val Asn Leu Arg
            100                 105                 110

Glu Phe Met Leu Ala Thr Met Pro Leu Asp Ala Lys Ser Lys Ile Gly
        115                 120                 125

Gly Pro Asn Pro Tyr Pro Gln His Leu Gln Gly Cys Gln Trp Ser Ala
    130                 135                 140

Gln Thr Thr Gln Asp Ala Trp Pro Tyr Ala Ala Gly Met Ser Glu Thr
145                 150                 155                 160

Lys Arg Pro Ser Val Pro Pro Ser Glu Trp Trp Arg Trp Ala Leu Leu
                165                 170                 175

Val Met His Pro Arg Ala Pro Gly Arg Phe Tyr Asn Ala Pro Lys Leu
            180                 185                 190

Met Thr Leu Asp Ala Met Gly Asp Leu Leu Gly Gly Trp Gln Leu Phe
        195                 200                 205

Arg His Val Lys Thr Lys Phe Arg Val Leu Ala Thr Met Gly Gln Gly
    210                 215                 220

Ala Phe Ser Pro Val Ala Ser Leu Leu Val Gln Asn Asp Tyr Trp Ser
225                 230                 235                 240

Arg Arg His Leu Glu Gly Phe Pro Val Lys Gly Ala Pro Pro Met Cys
                245                 250                 255

Thr Met Gln Arg Lys Thr Gln Gln Tyr Gly Asn Val Glu Ser Asn Ala
            260                 265                 270

Pro Ala Asp Glu Gln Trp Leu Pro Val Asn Pro Pro Asp Pro Pro Val
        275                 280                 285

Tyr Pro Asn Gln Gly Gly Cys Ser Gln Asn Val Ala Pro Gly Ile Tyr
    290                 295                 300

Arg Leu Ala Gly Leu Glu Asp Ser Ser Arg Cys Phe Tyr Ser Lys Ala
305                 310                 315                 320

Cys Phe Pro Ser Phe Ala Ala Leu Ser Ala Met Gly Ala Pro Trp Ser
                325                 330                 335

Phe Pro Ser Thr Gln Lys Pro Ile Gln Arg Gly Ser Phe Asn Lys His
            340                 345                 350

Ser Ile Thr Gly Thr Gly Asp Pro Gln Gly Arg Arg Trp Leu Thr Leu
        355                 360                 365

Val Pro Lys Gly Val Glu Trp Ile Thr Asp Asp Thr Met Glu Pro Thr
    370                 375                 380

Gln Leu Asp Thr Asp Ile Ala Thr Leu Phe Leu Ala Gln Gly Ser Pro
385                 390                 395                 400

Val Trp Ala Pro Tyr Lys Phe Gly Thr Phe His Lys Ala Met Ala Leu
                405                 410                 415

Thr Ala Met Gln Thr Thr Pro Trp Cys Val Val Lys Val Arg Ser Ile
            420                 425                 430
```

-continued

Trp Gln Leu Gly Asn Gln Arg Gln Pro Tyr Pro Trp Gln Val Asn Trp
435 440 445

Tyr Asn Glu His Thr Ala Thr Asp Arg Tyr Asn
450 455

<210> SEQ ID NO 4
<211> LENGTH: 696
<212> TYPE: DNA
<213> ORGANISM: artificial
<220> FEATURE:
<223> OTHER INFORMATION: H-VP2

<400> SEQUENCE: 4
atgtcatccg gcggtctcgg ggattgcagc gcctgtgaga accgagccgc tgggggcagt 60
gaattgccgc ttaggcaaga ggggcaactt gggcccagcg gagccggatc cacgggcaag 120
acactaaatg cagacccccc gctctcgccg acgagcaaca actactcagt cagaactatt 180
aacggcatac gagcatccaa caagttcgtc tccgccagca gaaacgacct cgatagagat 240
ccaaattggt atcgggtcaa ctataattac tctatcgcta cctggctacg ccagtgtgcg 300
cgttctcacg acgagatctg cacctgcgga cgatggagga gtcactggtt ccaggaggct 360
agtggacttg tcacacagga gacccagacg gaccagctcg ccagagatct acgtcggctt 420
cgccgcaaag gagaagcagc aaaaagaaaa cttgattacc ttaagggaaa acggaccccc 480
tataaaaaag ctaagactgt aacatggcaa gactacgaag aagacgacct cgcggacgct 540
ttggcttcta ccacagagga cgatggcact ggagacacag actgcgacga agacgctatt 600
cccggagggg taaatttcga tatgcgcgta gaagatcctt tgatcgccgc gttaagagga 660
ggatcttcaa cccacacccg ggctcctatg tggtaa 696

<210> SEQ ID NO 5
<211> LENGTH: 231
<212> TYPE: PRT
<213> ORGANISM: artificial
<220> FEATURE:
<223> OTHER INFORMATION: H-VP2

<400> SEQUENCE: 5

Met Ser Ser Gly Gly Leu Gly Asp Cys Ser Ala Cys Glu Asn Arg Ala
1 5 10 15

Ala Gly Gly Ser Glu Leu Pro Leu Arg Gln Glu Gly Gln Leu Gly Pro
20 25 30

Ser Gly Ala Gly Ser Thr Gly Lys Thr Leu Asn Ala Asp Pro Pro Leu
35 40 45

Ser Pro Thr Ser Asn Asn Tyr Ser Val Arg Thr Ile Asn Gly Ile Arg
50 55 60

Ala Ser Asn Lys Phe Val Ser Ala Ser Arg Asn Asp Leu Asp Arg Asp
65 70 75 80

Pro Asn Trp Tyr Arg Val Asn Tyr Asn Tyr Ser Ile Ala Thr Trp Leu
85 90 95

Arg Gln Cys Ala Arg Ser His Asp Glu Ile Cys Thr Cys Gly Arg Trp
100 105 110

Arg Ser His Trp Phe Gln Glu Ala Ser Gly Leu Val Thr Gln Glu Thr
115 120 125

Gln Thr Asp Gln Leu Ala Arg Asp Leu Arg Arg Leu Arg Arg Lys Gly
130 135 140

Glu Ala Ala Lys Arg Lys Leu Asp Tyr Leu Lys Gly Lys Arg Thr Pro
145 150 155 160

-continued

Tyr Lys Lys Ala Lys Thr Val Thr Trp Gln Asp Tyr Glu Glu Asp Asp
165 170 175

Leu Ala Asp Ala Leu Ala Ser Thr Thr Glu Asp Asp Gly Thr Gly Asp
180 185 190

Thr Asp Cys Asp Glu Asp Ala Ile Pro Gly Gly Val Asn Phe Asp Met
195 200 205

Arg Val Glu Asp Pro Leu Ile Ala Ala Leu Arg Gly Gly Ser Ser Thr
210 215 220

His Thr Arg Ala Pro Met Trp
225 230

<210> SEQ ID NO 6
<211> LENGTH: 375
<212> TYPE: DNA
<213> ORGANISM: artificial
<220> FEATURE:
<223> OTHER INFORMATION: H-apoptin

<400> SEQUENCE: 6
atgcagaccc cccgctctcg ccgacgagca acaactactc agtcagaact attaacggca 60
tacgagcatc caacaagttc gtctccgcca gcagaaacga cctcgataga gatccaaatt 120
ggtatcgggt caactataat tactctatcg ctacctggct acgccagtgt gcgcgttctc 180
acgacgagat ctgcacctgc ggacgatgga ggagtcactg gttccaggag gctagtggac 240
ttgtcacaca ggagacccag acggaccagc tcgccagaga tctacgtcgg cttcgccgca 300
aaggagaagc agcaaaaaga aaacttgatt accttaaggg aaaacggacc ccctataaaa 360
aagctaagac tgtaa 375

<210> SEQ ID NO 7
<211> LENGTH: 124
<212> TYPE: PRT
<213> ORGANISM: artificial
<220> FEATURE:
<223> OTHER INFORMATION: H-apoptin

<400> SEQUENCE: 7

Met Gln Thr Pro Arg Ser Arg Arg Arg Ala Thr Thr Thr Gln Ser Glu
1 5 10 15

Leu Leu Thr Ala Tyr Glu His Pro Thr Ser Ser Ser Pro Pro Ala Glu
20 25 30

Thr Thr Ser Ile Glu Ile Gln Ile Gly Ile Gly Ser Thr Ile Ile Thr
35 40 45

Leu Ser Leu Pro Gly Tyr Ala Ser Val Arg Val Leu Thr Thr Arg Ser
50 55 60

Ala Pro Ala Asp Asp Gly Gly Val Thr Gly Ser Arg Arg Leu Val Asp
65 70 75 80

Leu Ser His Arg Arg Pro Arg Arg Thr Ser Ser Pro Glu Ile Tyr Val
85 90 95

Gly Phe Ala Ala Lys Glu Lys Gln Gln Lys Glu Asn Leu Ile Thr Leu
100 105 110

Arg Glu Asn Gly Pro Pro Ile Lys Lys Leu Arg Leu
115 120

<210> SEQ ID NO 8
<211> LENGTH: 2319
<212> TYPE: DNA
<213> ORGANISM: chicken anemia virus
<220> FEATURE:
<221> NAME/KEY: misc_feature
<223> OTHER INFORMATION: CAV

<400> SEQUENCE: 8
gaattccgag tggttactat tccatcacca ttctagcctg tacacagaaa gtcaagatgg 60
acgaatcgct cgacttcgct cgcgattcgt cgaaggcggg gggccggagg ccccccggtg 120
gcccccctcc aacgagtgga gcacgtacag gggggtacgt catccgtaca ggggggtacg 180
tcatccgtac aggggggtac gtcacaaaga ggcgttcccg tacagggggg tacgtcacgc 240
gtacaggggg gtacgtcaca gccaatcaaa agctgccacg ttgcgaaagt gacgtttcga 300
aaatgggcgg cgcaagcctc tctatatatt gagcgcacat accggtcggc agtaggtata 360
cgcaaggcgg tccgggtgga tgcacgggaa cggcggacaa ccggccgctg ggggcagtga 420
atcggcgctt agccgagagg ggcaacctgg gcccagcgga gccgcgcagg ggcaagtaat 480
ttcaaatgaa cgctctccaa gaagatactc cacccggacc atcaacggtg ttcaggccac 540
caacaagttc acggccgttg gaaacccctc actgcagaga gatccggatt ggtatcgctg 600
gaattacaat cactctatcg ctgtgtggct gcgcgaatgc tcgcgctccc acgctaagat 660
ctgcaactgc ggacaattca gaaagcactg gtttcaagaa tgtgccggac ttgaggaccg 720
atcaacccaa gcctccctcg aagaagcgat cctgcgaccc ctccgagtac agggtaagcg 780
agctaaaaga aagcttgatt accactactc ccagccgacc ccgaaccgca aaaaggcgta 840
taagactgta agatggcaag acgagctcgc agaccgagag gccgatttta ctccttcaga 900
agaggacggt ggcaccacct caagcgactt cgacgaagat ataaatttcg acatcggagg 960
agacagcggt atcgtagacg agcttttagg aaggcctttc acaacccccg ccccggtacg 1020
tatagtgtga ggctgccgaa cccccaatct actatgacta tccgcttcca aggggtcatc 1080
tttctcacgg aaggactcat tctgcctaaa aacagcacag cggggggcta tgcagaccac 1140
atgtacgggg cgagagtcgc caagatctct gtgaacctga aagagttcct gctagcctca 1200
atgaacctga catacgtgag caaaatcgga ggccccatcg ccggtgagtt gattgcggac 1260
gggtctaaat cacaagccgc ggacaattgg cctaattgct ggctgccgct agataataac 1320
gtgccctccg ctacaccatc ggcatggtgg agatgggcct taatgatgat gcagcccacg 1380
gactcttgcc ggttctttaa tcacccaaag cagatgaccc tgcaagacat gggtcgcatg 1440
tttgggggct ggcacctgtt ccgacacatt gaaacccgct ttcagctcct tgccactaag 1500
aatgagggat ccttcagccc cgtggcgagt cttctctccc agggagagta cctcacgcgt 1560
cgggacgatg ttaagtacag cagcgatcac cagaaccggt ggcaaaaagg cggacaaccg 1620
atgacggggg gcattgctta tgcgaccggg aaaatgagac ccgacgagca acagtaccct 1680
gctatgcccc cagaccccc gatcatcacc gctactacag cgcaaggcac gcaagtccgc 1740
tgcatgaata gcacgcaagc ttggtggtca tgggacacat atatgagctt tgcaacactc 1800
acagcactcg gtgcacaatg gtcttttcct ccagggcaac gttcagtttc tagacggtcc 1860
ttcaaccacc acaaggcgag aggagccggg gaccccaagg gccagagatg gcacacgctg 1920
gtgccgctcg gcacggagac catcaccgac agctacatgt cagcacccgc atcagagctg 1980
gacactaatt tctttacgct ttacgtagcg caaggcacaa ataagtcgca acagtacaag 2040
ttcggcacag ctacatacgc gctaaaggag ccggtaatga agagcgatgc atgggcagtg 2100
gtacgcgtcc agtcggtctg gcagctgggt aacaggcaga ggccataccc atggacgtc 2160 aactgggcga acagcaccat gtactggggg acgcagccct gaaaaggggg gggggctaaa 2220

```
gcccccccccc cttaaacccc cccctggggg ggattccccc ccagaccccc cctttatata   2280

gcactcaata aacgcagaaa atagatttat cgcactatc                          2319
```

<210> SEQ ID NO 9
<211> LENGTH: 651
<212> TYPE: DNA
<213> ORGANISM: chicken anemia virus
<220> FEATURE:
<221> NAME/KEY: misc_feature
<223> OTHER INFORMATION: CAV ORF1 VP1

<400> SEQUENCE: 9

```
atgcacggga acggcggaca accggccgct gggggcagtg aatcggcgct tagccgagag     60

gggcaacctg ggcccagcgg agccgcgcag ggcaagtaa tttcaaatga acgctctcca    120

agaagatact ccacccggac catcaacggt gttcaggcca ccaacaagtt cacggccgtt    180

ggaaacccct cactgcagag agatccggat tggtatcgct ggaattacaa tcactctatc    240

gctgtgtggc tgcgcgaatg ctcgcgctcc cacgctaaga tctgcaactg cggacaattc    300

agaaagcact ggtttcaaga atgtgccgga cttgaggacc gatcaaccca agcctccctc    360

gaagaagcga tcctgcgacc cctccgagta cagggtaagc gagctaaaag aaagcttgat    420

taccactact cccagccgac cccgaaccgc aaaaaggcgt ataagactgt aagatggcaa    480

gacgagctcg cagaccgaga ggccgatttt actccttcag aagaggacgg tggcaccacc    540

tcaagcgact tcgacgaaga tataaatttc gacatcggag gagacagcgg tatcgtagac    600

gagcttttag gaaggccttt cacaaccccc gccccggtac gtatagtgtg a            651
```

<210> SEQ ID NO 10
<211> LENGTH: 366
<212> TYPE: DNA
<213> ORGANISM: chicken anemia virus
<220> FEATURE:
<221> NAME/KEY: misc_feature
<223> OTHER INFORMATION: CAV ORF2 VP2

<400> SEQUENCE: 10

```
atgaacgctc tccaagaaga tactccaccc ggaccatcaa cggtgttcag gccaccaaca     60

agttcacggc cgttggaaac ccctcactgc agagagatcc ggattggtat cgctggaatt    120

acaatcactc tatcgctgtg tggctgcgcg aatgctcgcg ctcccacgct aagatctgca    180

actgcggaca attcagaaag cactggtttc aagaatgtgc cggacttgag gaccgatcaa    240

cccaagcctc cctcgaagaa gcgatcctgc gacccctccg agtacagggt aagcgagcta    300

aaagaaagct tgattaccac tactcccagc cgaccccgaa ccgcaaaaag gcgtataaga    360

ctgtaa                                                               366
```

<210> SEQ ID NO 11
<211> LENGTH: 1350
<212> TYPE: DNA
<213> ORGANISM: chicken anemia virus
<220> FEATURE:
<221> NAME/KEY: misc_feature
<223> OTHER INFORMATION: CAV ORF3 VP3

<400> SEQUENCE: 11

```
atggcaagac gagctcgcag accgagaggc cgattttact ccttcagaag aggacggtgg     60

caccacctca agcgacttcg acgaagatat aaatttcgac atcggaggag acagcggtat    120

cgtagacgag cttttaggaa ggcctttcac aacccccgcc ccggtacgta tagtgtgagg    180
```

-continued

```
ctgccgaacc cccaatctac tatgactatc cgcttccaag ggtcatcttt tctcacggaa    240

ggactcattc tgcctaaaaa cagcacagcg gggggctatg cagaccacat gtacggggcg    300

agagtcgcca agatctctgt gaacctgaaa gagttcctgc tagcctcaat gaacctgaca    360

tacgtgagca aaatcggagg ccccatcgcc ggtgagttga ttgcggacgg gtctaaatca    420

caagccgcgg acaattggcc taattgctgg ctgccgctag ataataacgt gccctccgct    480

acaccatcgg catggtggag atgggcctta atgatgatgc agcccacgga ctcttgccgg    540

ttctttaatc acccaaagca gatgaccctg caagacatgg gtcgcatgtt tgggggctgg    600

cacctgttcc gacacattga aacccgcttt cagctccttg ccactaagaa tgagggatcc    660

ttcagccccg tggcgagtct tctctcccag ggagagtacc tcacgcgtcg ggacgatgtt    720

aagtacagca gcgatcacca gaaccggtgg caaaaaggcg gacaaccgat gacgggggc     780

attgcttatg cgaccgggaa aatgagaccc gacgagcaac agtaccctgc tatgccccca    840

gaccccccga tcatcaccgc tactacagcg caaggcacgc aagtccgctg catgaatagc    900

acgcaagctt ggtggtcatg ggacacatat atgagctttg caacactcac agcactcggt    960

gcacaatggt cttttcctcc agggcaacgt tcagtttcta gacggtcctt caaccaccac   1020

aaggcgagag gagccgggga ccccaagggc cagagatggc acacgctggt gccgctcggc   1080

acggagacca tcaccgacag ctacatgtca gcacccgcat cagagctgga cactaatttc   1140

tttacgcttt acgtagcgca aggcacaaat aagtcgcaac agtacaagtt cggcacagct   1200

acatacgcgc taaaggagcc ggtaatgaag agcgatgcat gggcagtggt acgcgtccag   1260

tcggtctggc agctgggtaa caggcagagg ccatacccat gggacgtcaa ctgggcgaac   1320

agcaccatgt actgggggac gcagccctga                                    1350
```

```
<210> SEQ ID NO 12
<211> LENGTH: 449
<212> TYPE: PRT
<213> ORGANISM: chicken anemia virus

<400> SEQUENCE: 12

Met Ala Arg Arg Ala Arg Arg Pro Arg Gly Arg Phe Tyr Ala Phe Arg
1               5                   10                  15

Arg Gly Arg Trp His Asn Leu Lys Arg Leu Arg Arg Arg Tyr Lys Phe
            20                  25                  30

Arg His Arg Arg Arg Gln Arg Tyr Arg Arg Arg Ala Phe Arg Lys Ala
        35                  40                  45

Phe His Asn Pro Arg Pro Gly Thr Tyr Ser Val Arg Leu Pro Asn Pro
    50                  55                  60

Gln Ser Thr Met Thr Ile Arg Phe Gln Gly Ile Ile Phe Leu Thr Glu
65                  70                  75                  80

Gly Leu Ile Leu Pro Lys Asn Ser Thr Ala Gly Gly Tyr Ala Asp His
                85                  90                  95

Leu Tyr Gly Ala Arg Val Ala Lys Ile Ser Val Asn Leu Lys Glu Phe
            100                 105                 110

Leu Leu Ala Ser Met Asn Leu Thr Tyr Val Ser Lys Ile Gly Gly Pro
        115                 120                 125

Ile Ala Gly Glu Leu Ile Ala Asp Gly Ser Gln Ser Gln Ala Ala Gln
    130                 135                 140

Asn Trp Pro Asn Cys Trp Leu Pro Leu Asp Asn Asn Val Pro Ser Ala
145                 150                 155                 160
```

-continued

```
Thr Pro Ser Ala Trp Trp Arg Trp Ala Leu Met Met Met Gln Pro Thr
                165                 170                 175

Asp Ser Cys Arg Phe Phe Asn His Pro Lys Gln Met Thr Leu Gln Asp
            180                 185                 190

Met Gly Arg Met Phe Gly Gly Trp His Leu Phe Arg His Ile Glu Thr
        195                 200                 205

Arg Phe Gln Leu Leu Ala Thr Lys Asn Glu Gly Ser Phe Ser Pro Val
    210                 215                 220

Ala Ser Leu Leu Ser Gln Gly Glu Tyr Leu Thr Arg Arg Asp Asp Val
225                 230                 235                 240

Lys Tyr Ser Ser Asp His Gln Asn Arg Trp Arg Lys Gly Glu Gln Pro
                245                 250                 255

Met Thr Gly Gly Ile Ala Tyr Ala Thr Gly Lys Met Arg Pro Asp Glu
            260                 265                 270

Gln Gln Tyr Pro Ala Met Pro Pro Asp Pro Pro Ile Ile Thr Ala Thr
        275                 280                 285

Thr Ala Gln Gly Thr Gln Val Arg Cys Met Asn Ser Thr Gln Ala Trp
    290                 295                 300

Trp Ser Trp Asp Thr Tyr Met Ser Phe Ala Thr Leu Thr Ala Leu Gly
305                 310                 315                 320

Ala Gln Trp Ser Phe Pro Pro Gly Gln Arg Ser Val Ser Arg Arg Ser
                325                 330                 335

Phe Asn His His Lys Ala Arg Gly Ala Gly Asp Pro Lys Gly Gln Arg
            340                 345                 350

Trp His Thr Leu Val Pro Leu Gly Thr Glu Thr Ile Thr Asp Ser Tyr
        355                 360                 365

Met Ser Ala Pro Ala Ser Glu Leu Asp Thr Asn Phe Phe Thr Leu Tyr
    370                 375                 380

Val Ala Gln Gly Thr Asn Lys Ser Gln Gln Tyr Lys Phe Gly Thr Ala
385                 390                 395                 400

Thr Tyr Ala Leu Lys Glu Pro Val Met Lys Ser Asp Ala Trp Ala Val
                405                 410                 415

Val Arg Val Gln Ser Val Trp Gln Leu Gly Asn Arg Gln Arg Pro Tyr
            420                 425                 430

Pro Trp Asp Val Asn Trp Ala Asn Ser Thr Met Tyr Trp Gly Ser Gln
        435                 440                 445

Pro


<210> SEQ ID NO 13
<211> LENGTH: 216
<212> TYPE: PRT
<213> ORGANISM: chicken anemia virus

<400> SEQUENCE: 13

Met His Gly Asn Gly Gly Gln Pro Ala Ala Gly Gly Ser Glu Ser Ala
1               5                   10                  15

Leu Ser Arg Glu Gly Gln Pro Gly Pro Ser Gly Ala Ala Gln Gly Gln
            20                  25                  30

Val Ile Ser Asn Glu Arg Ser Pro Arg Arg Tyr Ser Thr Arg Thr Ile
        35                  40                  45

Asn Gly Val Gln Ala Thr Asn Lys Phe Thr Ala Val Gly Asn Pro Ser
    50                  55                  60

Leu Gln Arg Asp Pro Asp Trp Tyr Arg Trp Asn Tyr Asn His Ser Ile
65                  70                  75                  80
```

-continued

```
Ala Val Trp Leu Arg Glu Cys Ser Arg Ser His Ala Lys Ile Cys Asn
                85                  90                  95

Cys Gly Gln Phe Arg Lys His Trp Phe Gln Glu Cys Ala Gly Leu Glu
            100                 105                 110

Asp Arg Ser Thr Gln Ala Ser Leu Glu Glu Ala Ile Leu Arg Pro Leu
        115                 120                 125

Arg Val Gln Gly Lys Arg Ala Lys Arg Lys Leu Asp Tyr His Tyr Ser
    130                 135                 140

Gln Pro Thr Pro Asn Arg Lys Lys Val Tyr Lys Thr Val Arg Trp Gln
145                 150                 155                 160

Asp Glu Leu Ala Asp Arg Glu Ala Asp Phe Thr Pro Ser Glu Glu Asp
                165                 170                 175

Gly Gly Thr Thr Ser Ser Asp Phe Asp Glu Asp Ile Asn Phe Asp Ile
            180                 185                 190

Gly Gly Asp Ser Gly Ile Val Asp Glu Leu Leu Gly Arg Pro Phe Thr
        195                 200                 205

Thr Pro Ala Pro Val Arg Ile Val
    210                 215


<210> SEQ ID NO 14
<211> LENGTH: 121
<212> TYPE: PRT
<213> ORGANISM: chicken anemia virus

<400> SEQUENCE: 14

Met Asn Ala Leu Gln Glu Asp Thr Pro Pro Gly Pro Ser Thr Val Phe
1               5                   10                  15

Arg Pro Pro Thr Ser Ser Arg Pro Leu Glu Thr Pro His Cys Arg Glu
            20                  25                  30

Ile Arg Ile Gly Ile Ala Gly Ile Thr Ile Thr Leu Ser Leu Cys Gly
        35                  40                  45

Cys Ala Asn Ala Arg Ala Pro Thr Leu Arg Ser Ala Thr Ala Asp Asn
    50                  55                  60

Ser Glu Ser Thr Gly Phe Lys Asn Val Pro Asp Leu Arg Thr Asp Gln
65                  70                  75                  80

Pro Lys Pro Pro Ser Lys Lys Arg Ser Cys Asp Pro Ser Glu Tyr Arg
                85                  90                  95

Val Ser Glu Leu Lys Glu Ser Leu Ile Thr Thr Thr Pro Ser Arg Pro
            100                 105                 110

Arg Thr Ala Lys Arg Arg Ile Arg Leu
        115                 120


<210> SEQ ID NO 15
<211> LENGTH: 380
<212> TYPE: PRT
<213> ORGANISM: artificial
<220> FEATURE:
<223> OTHER INFORMATION: promoter region of HGyV

<400> SEQUENCE: 15

Cys Gly Gly Cys Gly Cys Gly Cys Gly Cys Gly Gly Cys Ala Gly Cys
1               5                   10                  15

Ala Gly Cys Cys Thr Gly Thr Ala Cys Ala Cys Ala Gly Ala Gly Ala
            20                  25                  30

Cys Gly Thr Cys Gly Cys Thr Cys Gly Gly Gly Thr Cys Cys Thr Cys
        35                  40                  45

Cys Gly Gly Ala Cys Cys Cys Thr Cys Gly Cys Thr Cys Cys Thr Cys
```

50 55 60

Ala Ala Cys Cys Thr Thr Thr Thr Cys Thr Thr Ala Thr Thr Ala Ala
65 70 75 80

Ala Ala Thr Cys Ala Thr Cys Ala Cys Cys Cys Ala Gly Cys Gly Cys
85 90 95

Gly Ala Cys Ala Ala Ala Cys Gly Cys Cys Ala Cys Ala Ala Gly Gly
100 105 110

Cys Gly Thr Gly Gly Thr Ala Ala Cys Cys Ala Ala Cys Gly Ala Thr
115 120 125

Ala Thr Gly Thr Ala Ala Gly Thr Ala Ala Ala Cys Thr Gly Ala Gly
130 135 140

Ala Cys Thr Cys Ala Thr Ala Cys Cys Gly Gly Thr Ala Cys Ala Gly
145 150 155 160

Gly Gly Gly Gly Gly Thr Ala Cys Gly Thr Cys Ala Cys Cys Ala Thr
165 170 175

Gly Thr Ala Cys Ala Gly Gly Gly Gly Gly Gly Thr Ala Cys Gly Thr
180 185 190

Cys Ala Cys Cys Ala Thr Gly Thr Ala Cys Ala Gly Gly Gly Gly Gly
195 200 205

Gly Thr Ala Cys Gly Thr Cys Ala Thr Cys Ala Thr Gly Thr Ala Cys
210 215 220

Ala Gly Gly Gly Gly Gly Gly Thr Ala Cys Gly Thr Cys Ala Cys Cys
225 230 235 240

Ala Thr Gly Thr Ala Cys Ala Gly Gly Gly Gly Gly Gly Thr Ala Cys
245 250 255

Gly Thr Cys Ala Cys Cys Ala Thr Gly Thr Ala Cys Ala Gly Gly Gly
260 265 270

Gly Gly Gly Thr Ala Cys Gly Thr Cys Ala Cys Ala Gly Cys Cys Ala
275 280 285

Ala Thr Cys Ala Gly Ala Ala Thr Thr Gly Ala Gly Cys Ala Cys Gly
290 295 300

Cys Cys Cys Ala Gly Gly Ala Ala Cys Gly Cys Cys Cys Cys Thr Gly
305 310 315 320

Gly Gly Cys Gly Gly Gly Gly Ala Gly Ala Thr Gly Cys Thr Ala Thr
325 330 335

Cys Ala Ala Thr Thr Thr Ala Gly Gly Gly Ala Thr Ala Thr Ala Ala
340 345 350

Gly Cys Ala Gly Ala Gly Cys Ala Cys Ala Thr Ala Cys Cys Gly Gly
355 360 365

Ala Cys Gly Gly Cys Gly Gly Thr Ala Gly Gly Thr
370 375 380

<210> SEQ ID NO 16
<211> LENGTH: 22
<212> TYPE: DNA
<213> ORGANISM: artificial
<220> FEATURE:
<223> OTHER INFORMATION: conserved repetition

<400> SEQUENCE: 16
mkgtacaggg gggtacgtca ym 22

<210> SEQ ID NO 17
<211> LENGTH: 12
<212> TYPE: DNA
<213> ORGANISM: artificial

<220> FEATURE:
<223> OTHER INFORMATION: palindromic sequence

<400> SEQUENCE: 17
caatcagaat tg 12

<210> SEQ ID NO 18
<211> LENGTH: 2432
<212> TYPE: DNA
<213> ORGANISM: artificial
<220> FEATURE:
<223> OTHER INFORMATION: consensus between CAV M55918 and HGyV
<220> FEATURE:
<221> NAME/KEY: misc_feature
<222> LOCATION: (1)..(5)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (14)..(16)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (62)..(66)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (71)..(71)
<223> OTHER INFORMATION: n is a, c, g, or t
<220> FEATURE:
<221> NAME/KEY: misc_feature
<222> LOCATION: (73)..(78)
<223> OTHER INFORMATION: n is a, c, g, or t
<220> FEATURE:
<221> NAME/KEY: misc_feature
<222> LOCATION: (80)..(80)
<223> OTHER INFORMATION: n is a, c, g, or t
<220> FEATURE:
<221> NAME/KEY: misc_feature
<222> LOCATION: (83)..(85)
<223> OTHER INFORMATION: n is a, c, g, or t
<220> FEATURE:
<221> NAME/KEY: misc_feature
<222> LOCATION: (87)..(91)
<223> OTHER INFORMATION: n is a, c, g, or t
<220> FEATURE:
<221> NAME/KEY: misc_feature
<222> LOCATION: (93)..(94)
<223> OTHER INFORMATION: n is a, c, g, or t
<220> FEATURE:
<221> NAME/KEY: misc_feature
<222> LOCATION: (96)..(97)
<223> OTHER INFORMATION: n is a, c, g, or t
<220> FEATURE:

<221> NAME/KEY: misc_feature
<222> LOCATION: (100)..(101)
<223> OTHER INFORMATION: n is a, c, g, or t
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (112)..(112)
<223> OTHER INFORMATION: n is a, c, g, or t
<220> FEATURE:
<221> NAME/KEY: misc_feature
<222> LOCATION: (114)..(114)
<223> OTHER INFORMATION: n is a, c, g, or t
<220> FEATURE:
<221> NAME/KEY: misc_feature
<222> LOCATION: (116)..(116)
<223> OTHER INFORMATION: n is a, c, g, or t
<220> FEATURE:
<221> NAME/KEY: misc_feature
<222> LOCATION: (118)..(119)
<223> OTHER INFORMATION: n is a, c, g, or t
<220> FEATURE:
<221> NAME/KEY: misc_feature
<222> LOCATION: (121)..(121)
<223> OTHER INFORMATION: n is a, c, g, or t
<220> FEATURE:
<221> NAME/KEY: misc_feature
<222> LOCATION: (125)..(125)
<223> OTHER INFORMATION: n is a, c, g, or t
<220> FEATURE:
<221> NAME/KEY: misc_feature
<222> LOCATION: (127)..(127)
<223> OTHER INFORMATION: n is a, c, g, or t
<220> FEATURE:
<221> NAME/KEY: misc_feature
<222> LOCATION: (133)..(133)
<223> OTHER INFORMATION: n is a, c, g, or t
<220> FEATURE:
<221> NAME/KEY: misc_feature
<222> LOCATION: (137)..(138)
<223> OTHER INFORMATION: n is a, c, g, or t
<220> FEATURE:
<221> NAME/KEY: misc_feature
<222> LOCATION: (141)..(142)
<223> OTHER INFORMATION: n is a, c, g, or t
<220> FEATURE:
<221> NAME/KEY: misc_feature
<222> LOCATION: (144)..(151)
<223> OTHER INFORMATION: n is a, c, g, or t
<220> FEATURE:
<221> NAME/KEY: misc_feature
<222> LOCATION: (155)..(156)
<223> OTHER INFORMATION: n is a, c, g, or t
<220> FEATURE:
<221> NAME/KEY: misc_feature
<222> LOCATION: (169)..(169)
<223> OTHER INFORMATION: n is a, c, g, or t
<220> FEATURE:
<221> NAME/KEY: misc_feature
<222> LOCATION: (171)..(172)
<223> OTHER INFORMATION: n is a, c, g, or t
<220> FEATURE:
<221> NAME/KEY: misc_feature
<222> LOCATION: (191)..(191)
<223> OTHER INFORMATION: n is a, c, g, or t
<220> FEATURE:
<221> NAME/KEY: misc_feature
<222> LOCATION: (194)..(194)
<223> OTHER INFORMATION: n is a, c, g, or t
<220> FEATURE:
<221> NAME/KEY: misc_feature
<222> LOCATION: (213)..(213)
<223> OTHER INFORMATION: n is a, c, g, or t
<220> FEATURE:
<221> NAME/KEY: misc_feature
<222> LOCATION: (216)..(216)
<223> OTHER INFORMATION: n is a, c, g, or t
<220> FEATURE:
<221> NAME/KEY: misc_feature
<222> LOCATION: (244)..(245)
<223> OTHER INFORMATION: n is a, c, g, or t
<220> FEATURE:
<221> NAME/KEY: misc_feature
<222> LOCATION: (247)..(247)
<223> OTHER INFORMATION: n is a, c, g, or t
<220> FEATURE:
<221> NAME/KEY: misc_feature
<222> LOCATION: (250)..(254)
<223> OTHER INFORMATION: n is a, c, g, or t
<220> FEATURE:
<221> NAME/KEY: misc_feature
<222> LOCATION: (260)..(260)
<223> OTHER INFORMATION: n is a, c, g, or t
<220> FEATURE:
<221> NAME/KEY: misc_feature
<222> LOCATION: (281)..(282)
<223> OTHER INFORMATION: n is a, c, g, or t
<220> FEATURE:
<221> NAME/KEY: misc_feature
<222> LOCATION: (311)..(311)
<223> OTHER INFORMATION: n is a, c, g, or t
<220> FEATURE:
<221> NAME/KEY: misc_feature
<222> LOCATION: (314)..(318)
<223> OTHER INFORMATION: n is a, c, g, or t
<220> FEATURE:
<221> NAME/KEY: misc_feature
<222> LOCATION: (323)..(324)
<223> OTHER INFORMATION: n is a, c, g, or t
<220> FEATURE:
<221> NAME/KEY: misc_feature
<222> LOCATION: (327)..(329)
<223> OTHER INFORMATION: n is a, c, g, or t
<220> FEATURE:
<221> NAME/KEY: misc_feature
<222> LOCATION: (331)..(332)
<223> OTHER INFORMATION: n is a, c, g, or t
<220> FEATURE:
<221> NAME/KEY: misc_feature
<222> LOCATION: (334)..(334)
<223> OTHER INFORMATION: n is a, c, g, or t
<220> FEATURE:
<221> NAME/KEY: misc_feature
<222> LOCATION: (336)..(337)
<223> OTHER INFORMATION: n is a, c, g, or t
<220> FEATURE:
<221> NAME/KEY: misc_feature
<222> LOCATION: (339)..(340)
<223> OTHER INFORMATION: n is a, c, g, or t
<220> FEATURE:
<221> NAME/KEY: misc_feature
<222> LOCATION: (342)..(347)
<223> OTHER INFORMATION: n is a, c, g, or t
<220> FEATURE:
<221> NAME/KEY: misc_feature
<222> LOCATION: (349)..(350)
<223> OTHER INFORMATION: n is a, c, g, or t
<220> FEATURE:
<221> NAME/KEY: misc_feature
<222> LOCATION: (352)..(356)
<223> OTHER INFORMATION: n is a, c, g, or t
<220> FEATURE:
<221> NAME/KEY: misc_feature
<222> LOCATION: (358)..(360)
<223> OTHER INFORMATION: n is a, c, g, or t
<220> FEATURE:
<221> NAME/KEY: misc_feature
<222> LOCATION: (362)..(365)
<223> OTHER INFORMATION: n is a, c, g, or t
<220> FEATURE:
<221> NAME/KEY: misc_feature
<222> LOCATION: (371)..(373)
<223> OTHER INFORMATION: n is a, c, g, or t
<220> FEATURE:
<221> NAME/KEY: misc_feature
<222> LOCATION: (376)..(376)

<223> OTHER INFORMATION: n is a, c, g, or t
<220> FEATURE:
<221> NAME/KEY: misc_feature
<222> LOCATION: (388)..(388)
<223> OTHER INFORMATION: n is a, c, g, or t
<220> FEATURE:
<221> NAME/KEY: misc_feature
<222> LOCATION: (393)..(393)
<223> OTHER INFORMATION: n is a, c, g, or t
<220> FEATURE:
<221> NAME/KEY: misc_feature
<222> LOCATION: (402)..(402)
<223> OTHER INFORMATION: n is a, c, g, or t
<220> FEATURE:
<221> NAME/KEY: misc_feature
<222> LOCATION: (405)..(408)
<223> OTHER INFORMATION: n is a, c, g, or t
<220> FEATURE:
<221> NAME/KEY: misc_feature
<222> LOCATION: (416)..(417)
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (422)..(423)
<223> OTHER INFORMATION: n is a, c, g, or t
<220> FEATURE:
<221> NAME/KEY: misc_feature
<222> LOCATION: (431)..(433)
<223> OTHER INFORMATION: n is a, c, g, or t
<220> FEATURE:
<221> NAME/KEY: misc_feature
<222> LOCATION: (435)..(435)
<223> OTHER INFORMATION: n is a, c, g, or t
<220> FEATURE:
<221> NAME/KEY: misc_feature
<222> LOCATION: (437)..(437)
<223> OTHER INFORMATION: n is a, c, g, or t
<220> FEATURE:
<221> NAME/KEY: misc_feature
<222> LOCATION: (439)..(441)
<223> OTHER INFORMATION: n is a, c, g, or t
<220> FEATURE:
<221> NAME/KEY: misc_feature
<222> LOCATION: (443)..(443)
<223> OTHER INFORMATION: n is a, c, g, or t
<220> FEATURE:
<221> NAME/KEY: misc_feature
<222> LOCATION: (445)..(446)
<223> OTHER INFORMATION: n is a, c, g, or t
<220> FEATURE:
<221> NAME/KEY: misc_feature
<222> LOCATION: (466)..(466)
<223> OTHER INFORMATION: n is a, c, g, or t
<220> FEATURE:
<221> NAME/KEY: misc_feature
<222> LOCATION: (468)..(468)
<223> OTHER INFORMATION: n is a, c, g, or t
<220> FEATURE:
<221> NAME/KEY: misc_feature
<222> LOCATION: (476)..(476)
<223> OTHER INFORMATION: n is a, c, g, or t
<220> FEATURE:
<221> NAME/KEY: misc_feature
<222> LOCATION: (478)..(478)
<223> OTHER INFORMATION: n is a, c, g, or t
<220> FEATURE:
<221> NAME/KEY: misc_feature
<222> LOCATION: (490)..(490)
<223> OTHER INFORMATION: n is a, c, g, or t
<220> FEATURE:
<221> NAME/KEY: misc_feature
<222> LOCATION: (508)..(509)
<223> OTHER INFORMATION: n is a, c, g, or t
<220> FEATURE:
<221> NAME/KEY: misc_feature
<222> LOCATION: (514)..(514)
<223> OTHER INFORMATION: n is a, c, g, or t
<220> FEATURE:
<221> NAME/KEY: misc_feature
<222> LOCATION: (522)..(523)
<223> OTHER INFORMATION: n is a, c, g, or t
<220> FEATURE:
<221> NAME/KEY: misc_feature
<222> LOCATION: (525)..(525)
<223> OTHER INFORMATION: n is a, c, g, or t
<220> FEATURE:
<221> NAME/KEY: misc_feature
<222> LOCATION: (527)..(528)
<223> OTHER INFORMATION: n is a, c, g, or t
<220> FEATURE:
<221> NAME/KEY: misc_feature
<222> LOCATION: (530)..(534)
<223> OTHER INFORMATION: n is a, c, g, or t
<220> FEATURE:
<221> NAME/KEY: misc_feature
<222> LOCATION: (548)..(550)
<223> OTHER INFORMATION: n is a, c, g, or t
<220> FEATURE:
<221> NAME/KEY: misc_feature
<222> LOCATION: (553)..(553)
<223> OTHER INFORMATION: n is a, c, g, or t
<220> FEATURE:
<221> NAME/KEY: misc_feature
<222> LOCATION: (569)..(571)
<223> OTHER INFORMATION: n is a, c, g, or t
<220> FEATURE:
<221> NAME/KEY: misc_feature
<222> LOCATION: (573)..(573)
<223> OTHER INFORMATION: n is a, c, g, or t
<220> FEATURE:
<221> NAME/KEY: misc_feature
<222> LOCATION: (575)..(575)
<223> OTHER INFORMATION: n is a, c, g, or t
<220> FEATURE:
<221> NAME/KEY: misc_feature
<222> LOCATION: (578)..(578)
<223> OTHER INFORMATION: n is a, c, g, or t
<220> FEATURE:
<221> NAME/KEY: misc_feature
<222> LOCATION: (581)..(581)
<223> OTHER INFORMATION: n is a, c, g, or t
<220> FEATURE:
<221> NAME/KEY: misc_feature
<222> LOCATION: (587)..(588)
<223> OTHER INFORMATION: n is a, c, g, or t
<220> FEATURE:
<221> NAME/KEY: misc_feature
<222> LOCATION: (590)..(590)
<223> OTHER INFORMATION: n is a, c, g, or t
<220> FEATURE:
<221> NAME/KEY: misc_feature
<222> LOCATION: (592)..(593)
<223> OTHER INFORMATION: n is a, c, g, or t
<220> FEATURE:
<221> NAME/KEY: misc_feature
<222> LOCATION: (596)..(597)
<223> OTHER INFORMATION: n is a, c, g, or t
<220> FEATURE:
<221> NAME/KEY: misc_feature
<222> LOCATION: (609)..(612)
<223> OTHER INFORMATION: n is a, c, g, or t
<220> FEATURE:
<221> NAME/KEY: misc_feature
<222> LOCATION: (616)..(618)
<223> OTHER INFORMATION: n is a, c, g, or t
<220> FEATURE:
<221> NAME/KEY: misc_feature
<222> LOCATION: (620)..(620)
<223> OTHER INFORMATION: n is a, c, g, or t
<220> FEATURE:
<221> NAME/KEY: misc_feature
<222> LOCATION: (622)..(625)
<223> OTHER INFORMATION: n is a, c, g, or t
<220> FEATURE:

<221> NAME/KEY: misc_feature
<222> LOCATION: (627)..(629)
<223> OTHER INFORMATION: n is a, c, g, or t
<220> FEATURE:
<221> NAME/KEY: misc_feature
<222> LOCATION: (632)..(633)
<223> OTHER INFORMATION: n is a, c, g, or t
<220> FEATURE:
<221> NAME/KEY: misc_feature
<222> LOCATION: (635)..(635)
<223> OTHER INFORMATION: n is a, c, g, or t
<220> FEATURE:
<221> NAME/KEY: misc_feature
<222> LOCATION: (644)..(645)
<223> OTHER INFORMATION: n is a, c, g, or t
<220> FEATURE:
<221> NAME/KEY: misc_feature
<222> LOCATION: (656)..(659)
<223> OTHER INFORMATION: n is a, c, g, or t
<220> FEATURE:
<221> NAME/KEY: misc_feature
<222> LOCATION: (662)..(662)
<223> OTHER INFORMATION: n is a, c, g, or t
<220> FEATURE:
<221> NAME/KEY: misc_feature
<222> LOCATION: (665)..(665)
<223> OTHER INFORMATION: n is a, c, g, or t
<220> FEATURE:
<221> NAME/KEY: misc_feature
<222> LOCATION: (669)..(669)
<223> OTHER INFORMATION: n is a, c, g, or t
<220> FEATURE:
<221> NAME/KEY: misc_feature
<222> LOCATION: (681)..(683)
<223> OTHER INFORMATION: n is a, c, g, or t
<220> FEATURE:
<221> NAME/KEY: misc_feature
<222> LOCATION: (689)..(689)
<223> OTHER INFORMATION: n is a, c, g, or t
<220> FEATURE:
<221> NAME/KEY: misc_feature
<222> LOCATION: (693)..(693)
<223> OTHER INFORMATION: n is a, c, g, or t
<220> FEATURE:
<221> NAME/KEY: misc_feature
<222> LOCATION: (695)..(695)
<223> OTHER INFORMATION: n is a, c, g, or t
<220> FEATURE:
<221> NAME/KEY: misc_feature
<222> LOCATION: (698)..(699)
<223> OTHER INFORMATION: n is a, c, g, or t
<220> FEATURE:
<221> NAME/KEY: misc_feature
<222> LOCATION: (704)..(704)
<223> OTHER INFORMATION: n is a, c, g, or t
<220> FEATURE:
<221> NAME/KEY: misc_feature
<222> LOCATION: (707)..(707)
<223> OTHER INFORMATION: n is a, c, g, or t
<220> FEATURE:
<221> NAME/KEY: misc_feature
<222> LOCATION: (712)..(714)
<223> OTHER INFORMATION: n is a, c, g, or t
<220> FEATURE:
<221> NAME/KEY: misc_feature
<222> LOCATION: (724)..(724)
<223> OTHER INFORMATION: n is a, c, g, or t
<220> FEATURE:
<221> NAME/KEY: misc_feature
<222> LOCATION: (733)..(733)
<223> OTHER INFORMATION: n is a, c, g, or t
<220> FEATURE:
<221> NAME/KEY: misc_feature
<222> LOCATION: (736)..(737)
<223> OTHER INFORMATION: n is a, c, g, or t
<220> FEATURE:
<221> NAME/KEY: misc_feature
<222> LOCATION: (740)..(740)
<223> OTHER INFORMATION: n is a, c, g, or t
<220> FEATURE:
<221> NAME/KEY: misc_feature
<222> LOCATION: (742)..(743)
<223> OTHER INFORMATION: n is a, c, g, or t
<220> FEATURE:
<221> NAME/KEY: misc_feature
<222> LOCATION: (752)..(752)
<223> OTHER INFORMATION: n is a, c, g, or t
<220> FEATURE:
<221> NAME/KEY: misc_feature
<222> LOCATION: (755)..(755)
<223> OTHER INFORMATION: n is a, c, g, or t
<220> FEATURE:
<221> NAME/KEY: misc_feature
<222> LOCATION: (758)..(760)
<223> OTHER INFORMATION: n is a, c, g, or t
<220> FEATURE:
<221> NAME/KEY: misc_feature
<222> LOCATION: (762)..(764)
<223> OTHER INFORMATION: n is a, c, g, or t
<220> FEATURE:
<221> NAME/KEY: misc_feature
<222> LOCATION: (772)..(776)
<223> OTHER INFORMATION: n is a, c, g, or t
<220> FEATURE:
<221> NAME/KEY: misc_feature
<222> LOCATION: (778)..(782)
<223> OTHER INFORMATION: n is a, c, g, or t
<220> FEATURE:
<221> NAME/KEY: misc_feature
<222> LOCATION: (788)..(789)
<223> OTHER INFORMATION: n is a, c, g, or t
<220> FEATURE:
<221> NAME/KEY: misc_feature
<222> LOCATION: (795)..(797)
<223> OTHER INFORMATION: n is a, c, g, or t
<220> FEATURE:
<221> NAME/KEY: misc_feature
<222> LOCATION: (802)..(805)
<223> OTHER INFORMATION: n is a, c, g, or t
<220> FEATURE:
<221> NAME/KEY: misc_feature
<222> LOCATION: (808)..(810)
<223> OTHER INFORMATION: n is a, c, g, or t
<220> FEATURE:
<221> NAME/KEY: misc_feature
<222> LOCATION: (812)..(812)
<223> OTHER INFORMATION: n is a, c, g, or t
<220> FEATURE:
<221> NAME/KEY: misc_feature
<222> LOCATION: (814)..(815)
<223> OTHER INFORMATION: n is a, c, g, or t
<220> FEATURE:
<221> NAME/KEY: misc_feature
<222> LOCATION: (818)..(818)
<223> OTHER INFORMATION: n is a, c, g, or t
<220> FEATURE:
<221> NAME/KEY: misc_feature
<222> LOCATION: (820)..(821)
<223> OTHER INFORMATION: n is a, c, g, or t
<220> FEATURE:
<221> NAME/KEY: misc_feature
<222> LOCATION: (823)..(823)
<223> OTHER INFORMATION: n is a, c, g, or t
<220> FEATURE:
<221> NAME/KEY: misc_feature
<222> LOCATION: (829)..(829)
<223> OTHER INFORMATION: n is a, c, g, or t
<220> FEATURE:
<221> NAME/KEY: misc_feature
<222> LOCATION: (831)..(831)
<223> OTHER INFORMATION: n is a, c, g, or t
<220> FEATURE:
<221> NAME/KEY: misc_feature
<222> LOCATION: (835)..(836)
<223> OTHER INFORMATION: n is a, c, g, or t
<220> FEATURE:
<221> NAME/KEY: misc_feature
<222> LOCATION: (845)..(845)

<223> OTHER INFORMATION: n is a, c, g, or t
<220> FEATURE:
<221> NAME/KEY: misc_feature
<222> LOCATION: (854)..(854)
<223> OTHER INFORMATION: n is a, c, g, or t
<220> FEATURE:
<221> NAME/KEY: misc_feature
<222> LOCATION: (865)..(867)
<223> OTHER INFORMATION: n is a, c, g, or t
<220> FEATURE:
<221> NAME/KEY: misc_feature
<222> LOCATION: (869)..(873)
<223> OTHER INFORMATION: n is a, c, g, or t
<220> FEATURE:
<221> NAME/KEY: misc_feature
<222> LOCATION: (875)..(875)
<223> OTHER INFORMATION: n is a, c, g, or t
<220> FEATURE:
<221> NAME/KEY: misc_feature
<222> LOCATION: (877)..(877)
<223> OTHER INFORMATION: n is a, c, g, or t
<220> FEATURE:
<221> NAME/KEY: misc_feature
<222> LOCATION: (888)..(890)
<223> OTHER INFORMATION: n is a, c, g, or t
<220> FEATURE:
<221> NAME/KEY: misc_feature
<222> LOCATION: (896)..(896)
<223> OTHER INFORMATION: n is a, c, g, or t
<220> FEATURE:
<221> NAME/KEY: misc_feature
<222> LOCATION: (913)..(913)
<223> OTHER INFORMATION: n is a, c, g, or t
<220> FEATURE:
<221> NAME/KEY: misc_feature
<222> LOCATION: (929)..(932)
<223> OTHER INFORMATION: n is a, c, g, or t
<220> FEATURE:
<221> NAME/KEY: misc_feature
<222> LOCATION: (934)..(935)
<223> OTHER INFORMATION: n is a, c, g, or t
<220> FEATURE:
<221> NAME/KEY: misc_feature
<222> LOCATION: (940)..(941)
<223> OTHER INFORMATION: n is a, c, g, or t
<220> FEATURE:
<221> NAME/KEY: misc_feature
<222> LOCATION: (943)..(943)
<223> OTHER INFORMATION: n is a, c, g, or t
<220> FEATURE:
<221> NAME/KEY: misc_feature
<222> LOCATION: (946)..(946)
<223> OTHER INFORMATION: n is a, c, g, or t
<220> FEATURE:
<221> NAME/KEY: misc_feature
<222> LOCATION: (949)..(949)
<223> OTHER INFORMATION: n is a, c, g, or t
<220> FEATURE:
<221> NAME/KEY: misc_feature
<222> LOCATION: (953)..(954)
<223> OTHER INFORMATION: n is a, c, g, or t
<220> FEATURE:
<221> NAME/KEY: misc_feature
<222> LOCATION: (957)..(957)
<223> OTHER INFORMATION: n is a, c, g, or t
<220> FEATURE:
<221> NAME/KEY: misc_feature
<222> LOCATION: (960)..(960)
<223> OTHER INFORMATION: n is a, c, g, or t
<220> FEATURE:
<221> NAME/KEY: misc_feature
<222> LOCATION: (962)..(964)
<223> OTHER INFORMATION: n is a, c, g, or t
<220> FEATURE:
<221> NAME/KEY: misc_feature
<222> LOCATION: (973)..(973)
<223> OTHER INFORMATION: n is a, c, g, or t
<220> FEATURE:
<221> NAME/KEY: misc_feature -continued
<222> LOCATION: (980)..(986)
<223> OTHER INFORMATION: n is a, c, g, or t
<220> FEATURE:
<221> NAME/KEY: misc_feature
<222> LOCATION: (988)..(989)
<223> OTHER INFORMATION: n is a, c, g, or t
<220> FEATURE:
<221> NAME/KEY: misc_feature
<222> LOCATION: (994)..(994)
<223> OTHER INFORMATION: n is a, c, g, or t
<220> FEATURE:
<221> NAME/KEY: misc_feature
<222> LOCATION: (1004)..(1005)
<223> OTHER INFORMATION: n is a, c, g, or t
<220> FEATURE:
<221> NAME/KEY: misc_feature
<222> LOCATION: (1031)..(1031)
<223> OTHER INFORMATION: n is a, c, g, or t
<220> FEATURE:
<221> NAME/KEY: misc_feature
<222> LOCATION: (1034)..(1035)
<223> OTHER INFORMATION: n is a, c, g, or t
<220> FEATURE:
<221> NAME/KEY: misc_feature
<222> LOCATION: (1037)..(1037)
<223> OTHER INFORMATION: n is a, c, g, or t
<220> FEATURE:
<221> NAME/KEY: misc_feature
<222> LOCATION: (1039)..(1039)
<223> OTHER INFORMATION: n is a, c, g, or t
<220> FEATURE:
<221> NAME/KEY: misc_feature
<222> LOCATION: (1043)..(1048)
<223> OTHER INFORMATION: n is a, c, g, or t
<220> FEATURE:
<221> NAME/KEY: misc_feature
<222> LOCATION: (1050)..(1050)
<223> OTHER INFORMATION: n is a, c, g, or t
<220> FEATURE:
<221> NAME/KEY: misc_feature
<222> LOCATION: (1052)..(1053)
<223> OTHER INFORMATION: n is a, c, g, or t
<220> FEATURE:
<221> NAME/KEY: misc_feature
<222> LOCATION: (1055)..(1055)
<223> OTHER INFORMATION: n is a, c, g, or t
<220> FEATURE:
<221> NAME/KEY: misc_feature
<222> LOCATION: (1057)..(1057)
<223> OTHER INFORMATION: n is a, c, g, or t
<220> FEATURE:
<221> NAME/KEY: misc_feature
<222> LOCATION: (1060)..(1060)
<223> OTHER INFORMATION: n is a, c, g, or t
<220> FEATURE:
<221> NAME/KEY: misc_feature
<222> LOCATION: (1062)..(1062)
<223> OTHER INFORMATION: n is a, c, g, or t
<220> FEATURE:
<221> NAME/KEY: misc_feature
<222> LOCATION: (1064)..(1066)
<223> OTHER INFORMATION: n is a, c, g, or t
<220> FEATURE:
<221> NAME/KEY: misc_feature
<222> LOCATION: (1071)..(1071)
<223> OTHER INFORMATION: n is a, c, g, or t
<220> FEATURE:
<221> NAME/KEY: misc_feature
<222> LOCATION: (1073)..(1074)
<223> OTHER INFORMATION: n is a, c, g, or t
<220> FEATURE:
<221> NAME/KEY: misc_feature
<222> LOCATION: (1087)..(1087)
<223> OTHER INFORMATION: n is a, c, g, or t
<220> FEATURE:
<221> NAME/KEY: misc_feature
<222> LOCATION: (1089)..(1089)
<223> OTHER INFORMATION: n is a, c, g, or t
<220> FEATURE:

<221> NAME/KEY: misc_feature
<222> LOCATION: (1093)..(1093)
<223> OTHER INFORMATION: n is a, c, g, or t
<220> FEATURE:
<221> NAME/KEY: misc_feature
<222> LOCATION: (1096)..(1097)
<223> OTHER INFORMATION: n is a, c, g, or t
<220> FEATURE:
<221> NAME/KEY: misc_feature
<222> LOCATION: (1099)..(1099)
<223> OTHER INFORMATION: n is a, c, g, or t
<220> FEATURE:
<221> NAME/KEY: misc_feature
<222> LOCATION: (1103)..(1105)
<223> OTHER INFORMATION: n is a, c, g, or t
<220> FEATURE:
<221> NAME/KEY: misc_feature
<222> LOCATION: (1108)..(1108)
<223> OTHER INFORMATION: n is a, c, g, or t
<220> FEATURE:
<221> NAME/KEY: misc_feature
<222> LOCATION: (1114)..(1114)
<223> OTHER INFORMATION: n is a, c, g, or t
<220> FEATURE:
<221> NAME/KEY: misc_feature
<222> LOCATION: (1123)..(1124)
<223> OTHER INFORMATION: n is a, c, g, or t
<220> FEATURE:
<221> NAME/KEY: misc_feature
<222> LOCATION: (1131)..(1133)
<223> OTHER INFORMATION: n is a, c, g, or t
<220> FEATURE:
<221> NAME/KEY: misc_feature
<222> LOCATION: (1135)..(1135)
<223> OTHER INFORMATION: n is a, c, g, or t
<220> FEATURE:
<221> NAME/KEY: misc_feature
<222> LOCATION: (1138)..(1139)
<223> OTHER INFORMATION: n is a, c, g, or t
<220> FEATURE:
<221> NAME/KEY: misc_feature
<222> LOCATION: (1142)..(1144)
<223> OTHER INFORMATION: n is a, c, g, or t
<220> FEATURE:
<221> NAME/KEY: misc_feature
<222> LOCATION: (1153)..(1154)
<223> OTHER INFORMATION: n is a, c, g, or t
<220> FEATURE:
<221> NAME/KEY: misc_feature
<222> LOCATION: (1156)..(1157)
<223> OTHER INFORMATION: n is a, c, g, or t
<220> FEATURE:
<221> NAME/KEY: misc_feature
<222> LOCATION: (1159)..(1159)
<223> OTHER INFORMATION: n is a, c, g, or t
<220> FEATURE:
<221> NAME/KEY: misc_feature
<222> LOCATION: (1162)..(1163)
<223> OTHER INFORMATION: n is a, c, g, or t
<220> FEATURE:
<221> NAME/KEY: misc_feature
<222> LOCATION: (1165)..(1166)
<223> OTHER INFORMATION: n is a, c, g, or t
<220> FEATURE:
<221> NAME/KEY: misc_feature
<222> LOCATION: (1171)..(1171)
<223> OTHER INFORMATION: n is a, c, g, or t
<220> FEATURE:
<221> NAME/KEY: misc_feature
<222> LOCATION: (1173)..(1174)
<223> OTHER INFORMATION: n is a, c, g, or t
<220> FEATURE:
<221> NAME/KEY: misc_feature
<222> LOCATION: (1176)..(1179)
<223> OTHER INFORMATION: n is a, c, g, or t
<220> FEATURE:
<221> NAME/KEY: misc_feature
<222> LOCATION: (1181)..(1181)
<223> OTHER INFORMATION: n is a, c, g, or t -continued
<220> FEATURE:
<221> NAME/KEY: misc_feature
<222> LOCATION: (1183)..(1185)
<223> OTHER INFORMATION: n is a, c, g, or t
<220> FEATURE:
<221> NAME/KEY: misc_feature
<222> LOCATION: (1191)..(1191)
<223> OTHER INFORMATION: n is a, c, g, or t
<220> FEATURE:
<221> NAME/KEY: misc_feature
<222> LOCATION: (1194)..(1194)
<223> OTHER INFORMATION: n is a, c, g, or t
<220> FEATURE:
<221> NAME/KEY: misc_feature
<222> LOCATION: (1196)..(1197)
<223> OTHER INFORMATION: n is a, c, g, or t
<220> FEATURE:
<221> NAME/KEY: misc_feature
<222> LOCATION: (1210)..(1212)
<223> OTHER INFORMATION: n is a, c, g, or t
<220> FEATURE:
<221> NAME/KEY: misc_feature
<222> LOCATION: (1217)..(1217)
<223> OTHER INFORMATION: n is a, c, g, or t
<220> FEATURE:
<221> NAME/KEY: misc_feature
<222> LOCATION: (1219)..(1222)
<223> OTHER INFORMATION: n is a, c, g, or t
<220> FEATURE:
<221> NAME/KEY: misc_feature
<222> LOCATION: (1228)..(1230)
<223> OTHER INFORMATION: n is a, c, g, or t
<220> FEATURE:
<221> NAME/KEY: misc_feature
<222> LOCATION: (1232)..(1233)
<223> OTHER INFORMATION: n is a, c, g, or t
<220> FEATURE:
<221> NAME/KEY: misc_feature
<222> LOCATION: (1238)..(1238)
<223> OTHER INFORMATION: n is a, c, g, or t
<220> FEATURE:
<221> NAME/KEY: misc_feature
<222> LOCATION: (1242)..(1244)
<223> OTHER INFORMATION: n is a, c, g, or t
<220> FEATURE:
<221> NAME/KEY: misc_feature
<222> LOCATION: (1247)..(1249)
<223> OTHER INFORMATION: n is a, c, g, or t
<220> FEATURE:
<221> NAME/KEY: misc_feature
<222> LOCATION: (1253)..(1253)
<223> OTHER INFORMATION: n is a, c, g, or t
<220> FEATURE:
<221> NAME/KEY: misc_feature
<222> LOCATION: (1259)..(1261)
<223> OTHER INFORMATION: n is a, c, g, or t
<220> FEATURE:
<221> NAME/KEY: misc_feature
<222> LOCATION: (1265)..(1265)
<223> OTHER INFORMATION: n is a, c, g, or t
<220> FEATURE:
<221> NAME/KEY: misc_feature
<222> LOCATION: (1268)..(1269)
<223> OTHER INFORMATION: n is a, c, g, or t
<220> FEATURE:
<221> NAME/KEY: misc_feature
<222> LOCATION: (1274)..(1274)
<223> OTHER INFORMATION: n is a, c, g, or t
<220> FEATURE:
<221> NAME/KEY: misc_feature
<222> LOCATION: (1277)..(1278)
<223> OTHER INFORMATION: n is a, c, g, or t
<220> FEATURE:
<221> NAME/KEY: misc_feature
<222> LOCATION: (1284)..(1287)
<223> OTHER INFORMATION: n is a, c, g, or t
<220> FEATURE:
<221> NAME/KEY: misc_feature
<222> LOCATION: (1289)..(1297)

<223> OTHER INFORMATION: n is a, c, g, or t
<220> FEATURE:
<221> NAME/KEY: misc_feature
<222> LOCATION: (1316)..(1316)
<223> OTHER INFORMATION: n is a, c, g, or t
<220> FEATURE:
<221> NAME/KEY: misc_feature
<222> LOCATION: (1318)..(1318)
<223> OTHER INFORMATION: n is a, c, g, or t
<220> FEATURE:
<221> NAME/KEY: misc_feature
<222> LOCATION: (1320)..(1320)
<223> OTHER INFORMATION: n is a, c, g, or t
<220> FEATURE:
<221> NAME/KEY: misc_feature
<222> LOCATION: (1322)..(1324)
<223> OTHER INFORMATION: n is a, c, g, or t
<220> FEATURE:
<221> NAME/KEY: misc_feature
<222> LOCATION: (1326)..(1330)
<223> OTHER INFORMATION: n is a, c, g, or t
<220> FEATURE:
<221> NAME/KEY: misc_feature
<222> LOCATION: (1332)..(1336)
<223> OTHER INFORMATION: n is a, c, g, or t
<220> FEATURE:
<221> NAME/KEY: misc_feature
<222> LOCATION: (1338)..(1338)
<223> OTHER INFORMATION: n is a, c, g, or t
<220> FEATURE:
<221> NAME/KEY: misc_feature
<222> LOCATION: (1340)..(1340)
<223> OTHER INFORMATION: n is a, c, g, or t
<220> FEATURE:
<221> NAME/KEY: misc_feature
<222> LOCATION: (1345)..(1347)
<223> OTHER INFORMATION: n is a, c, g, or t
<220> FEATURE:
<221> NAME/KEY: misc_feature
<222> LOCATION: (1362)..(1362)
<223> OTHER INFORMATION: n is a, c, g, or t
<220> FEATURE:
<221> NAME/KEY: misc_feature
<222> LOCATION: (1364)..(1365)
<223> OTHER INFORMATION: n is a, c, g, or t
<220> FEATURE:
<221> NAME/KEY: misc_feature
<222> LOCATION: (1368)..(1368)
<223> OTHER INFORMATION: n is a, c, g, or t
<220> FEATURE:
<221> NAME/KEY: misc_feature
<222> LOCATION: (1370)..(1371)
<223> OTHER INFORMATION: n is a, c, g, or t
<220> FEATURE:
<221> NAME/KEY: misc_feature
<222> LOCATION: (1373)..(1373)
<223> OTHER INFORMATION: n is a, c, g, or t
<220> FEATURE:
<221> NAME/KEY: misc_feature
<222> LOCATION: (1378)..(1378)
<223> OTHER INFORMATION: n is a, c, g, or t
<220> FEATURE:
<221> NAME/KEY: misc_feature
<222> LOCATION: (1380)..(1383)
<223> OTHER INFORMATION: n is a, c, g, or t
<220> FEATURE:
<221> NAME/KEY: misc_feature
<222> LOCATION: (1385)..(1387)
<223> OTHER INFORMATION: n is a, c, g, or t
<220> FEATURE:
<221> NAME/KEY: misc_feature
<222> LOCATION: (1390)..(1390)
<223> OTHER INFORMATION: n is a, c, g, or t
<220> FEATURE:
<221> NAME/KEY: misc_feature
<222> LOCATION: (1398)..(1398)
<223> OTHER INFORMATION: n is a, c, g, or t
<220> FEATURE:
<221> NAME/KEY: misc_feature
<222> LOCATION: (1400)..(1401)
<223> OTHER INFORMATION: n is a, c, g, or t
<220> FEATURE:
<221> NAME/KEY: misc_feature
<222> LOCATION: (1405)..(1405)
<223> OTHER INFORMATION: n is a, c, g, or t
<220> FEATURE:
<221> NAME/KEY: misc_feature
<222> LOCATION: (1407)..(1408)
<223> OTHER INFORMATION: n is a, c, g, or t
<220> FEATURE:
<221> NAME/KEY: misc_feature
<222> LOCATION: (1411)..(1414)
<223> OTHER INFORMATION: n is a, c, g, or t
<220> FEATURE:
<221> NAME/KEY: misc_feature
<222> LOCATION: (1418)..(1419)
<223> OTHER INFORMATION: n is a, c, g, or t
<220> FEATURE:
<221> NAME/KEY: misc_feature
<222> LOCATION: (1422)..(1424)
<223> OTHER INFORMATION: n is a, c, g, or t
<220> FEATURE:
<221> NAME/KEY: misc_feature
<222> LOCATION: (1429)..(1432)
<223> OTHER INFORMATION: n is a, c, g, or t
<220> FEATURE:
<221> NAME/KEY: misc_feature
<222> LOCATION: (1434)..(1435)
<223> OTHER INFORMATION: n is a, c, g, or t
<220> FEATURE:
<221> NAME/KEY: misc_feature
<222> LOCATION: (1442)..(1442)
<223> OTHER INFORMATION: n is a, c, g, or t
<220> FEATURE:
<221> NAME/KEY: misc_feature
<222> LOCATION: (1444)..(1444)
<223> OTHER INFORMATION: n is a, c, g, or t
<220> FEATURE:
<221> NAME/KEY: misc_feature
<222> LOCATION: (1450)..(1451)
<223> OTHER INFORMATION: n is a, c, g, or t
<220> FEATURE:
<221> NAME/KEY: misc_feature
<222> LOCATION: (1453)..(1454)
<223> OTHER INFORMATION: n is a, c, g, or t
<220> FEATURE:
<221> NAME/KEY: misc_feature
<222> LOCATION: (1457)..(1457)
<223> OTHER INFORMATION: n is a, c, g, or t
<220> FEATURE:
<221> NAME/KEY: misc_feature
<222> LOCATION: (1465)..(1465)
<223> OTHER INFORMATION: n is a, c, g, or t
<220> FEATURE:
<221> NAME/KEY: misc_feature
<222> LOCATION: (1468)..(1468)
<223> OTHER INFORMATION: n is a, c, g, or t
<220> FEATURE:
<221> NAME/KEY: misc_feature
<222> LOCATION: (1470)..(1471)
<223> OTHER INFORMATION: n is a, c, g, or t
<220> FEATURE:
<221> NAME/KEY: misc_feature
<222> LOCATION: (1473)..(1475)
<223> OTHER INFORMATION: n is a, c, g, or t
<220> FEATURE:
<221> NAME/KEY: misc_feature
<222> LOCATION: (1478)..(1478)
<223> OTHER INFORMATION: n is a, c, g, or t
<220> FEATURE:
<221> NAME/KEY: misc_feature
<222> LOCATION: (1481)..(1481)
<223> OTHER INFORMATION: n is a, c, g, or t
<220> FEATURE:
<221> NAME/KEY: misc_feature
<222> LOCATION: (1483)..(1483)
<223> OTHER INFORMATION: n is a, c, g, or t
<220> FEATURE:

<221> NAME/KEY: misc_feature
<222> LOCATION: (1486)..(1486)
<223> OTHER INFORMATION: n is a, c, g, or t
<220> FEATURE:
<221> NAME/KEY: misc_feature
<222> LOCATION: (1488)..(1489)
<223> OTHER INFORMATION: n is a, c, g, or t
<220> FEATURE:
<221> NAME/KEY: misc_feature
<222> LOCATION: (1493)..(1494)
<223> OTHER INFORMATION: n is a, c, g, or t
<220> FEATURE:
<221> NAME/KEY: misc_feature
<222> LOCATION: (1503)..(1504)
<223> OTHER INFORMATION: n is a, c, g, or t
<220> FEATURE:
<221> NAME/KEY: misc_feature
<222> LOCATION: (1510)..(1510)
<223> OTHER INFORMATION: n is a, c, g, or t
<220> FEATURE:
<221> NAME/KEY: misc_feature
<222> LOCATION: (1514)..(1514)
<223> OTHER INFORMATION: n is a, c, g, or t
<220> FEATURE:
<221> NAME/KEY: misc_feature
<222> LOCATION: (1516)..(1516)
<223> OTHER INFORMATION: n is a, c, g, or t
<220> FEATURE:
<221> NAME/KEY: misc_feature
<222> LOCATION: (1518)..(1519)
<223> OTHER INFORMATION: n is a, c, g, or t
<220> FEATURE:
<221> NAME/KEY: misc_feature
<222> LOCATION: (1525)..(1527)
<223> OTHER INFORMATION: n is a, c, g, or t
<220> FEATURE:
<221> NAME/KEY: misc_feature
<222> LOCATION: (1529)..(1529)
<223> OTHER INFORMATION: n is a, c, g, or t
<220> FEATURE:
<221> NAME/KEY: misc_feature
<222> LOCATION: (1534)..(1534)
<223> OTHER INFORMATION: n is a, c, g, or t
<220> FEATURE:
<221> NAME/KEY: misc_feature
<222> LOCATION: (1546)..(1546)
<223> OTHER INFORMATION: n is a, c, g, or t
<220> FEATURE:
<221> NAME/KEY: misc_feature
<222> LOCATION: (1549)..(1549)
<223> OTHER INFORMATION: n is a, c, g, or t
<220> FEATURE:
<221> NAME/KEY: misc_feature
<222> LOCATION: (1553)..(1553)
<223> OTHER INFORMATION: n is a, c, g, or t
<220> FEATURE:
<221> NAME/KEY: misc_feature
<222> LOCATION: (1555)..(1555)
<223> OTHER INFORMATION: n is a, c, g, or t
<220> FEATURE:
<221> NAME/KEY: misc_feature
<222> LOCATION: (1558)..(1559)
<223> OTHER INFORMATION: n is a, c, g, or t
<220> FEATURE:
<221> NAME/KEY: misc_feature
<222> LOCATION: (1561)..(1562)
<223> OTHER INFORMATION: n is a, c, g, or t
<220> FEATURE:
<221> NAME/KEY: misc_feature
<222> LOCATION: (1568)..(1570)
<223> OTHER INFORMATION: n is a, c, g, or t
<220> FEATURE:
<221> NAME/KEY: misc_feature
<222> LOCATION: (1573)..(1577)
<223> OTHER INFORMATION: n is a, c, g, or t
<220> FEATURE:
<221> NAME/KEY: misc_feature
<222> LOCATION: (1579)..(1579)
<223> OTHER INFORMATION: n is a, c, g, or t
<220> FEATURE:
<221> NAME/KEY: misc_feature
<222> LOCATION: (1582)..(1582)
<223> OTHER INFORMATION: n is a, c, g, or t
<220> FEATURE:
<221> NAME/KEY: misc_feature
<222> LOCATION: (1585)..(1585)
<223> OTHER INFORMATION: n is a, c, g, or t
<220> FEATURE:
<221> NAME/KEY: misc_feature
<222> LOCATION: (1590)..(1590)
<223> OTHER INFORMATION: n is a, c, g, or t
<220> FEATURE:
<221> NAME/KEY: misc_feature
<222> LOCATION: (1592)..(1595)
<223> OTHER INFORMATION: n is a, c, g, or t
<220> FEATURE:
<221> NAME/KEY: misc_feature
<222> LOCATION: (1597)..(1597)
<223> OTHER INFORMATION: n is a, c, g, or t
<220> FEATURE:
<221> NAME/KEY: misc_feature
<222> LOCATION: (1600)..(1601)
<223> OTHER INFORMATION: n is a, c, g, or t
<220> FEATURE:
<221> NAME/KEY: misc_feature
<222> LOCATION: (1603)..(1603)
<223> OTHER INFORMATION: n is a, c, g, or t
<220> FEATURE:
<221> NAME/KEY: misc_feature
<222> LOCATION: (1607)..(1609)
<223> OTHER INFORMATION: n is a, c, g, or t
<220> FEATURE:
<221> NAME/KEY: misc_feature
<222> LOCATION: (1612)..(1612)
<223> OTHER INFORMATION: n is a, c, g, or t
<220> FEATURE:
<221> NAME/KEY: misc_feature
<222> LOCATION: (1615)..(1615)
<223> OTHER INFORMATION: n is a, c, g, or t
<220> FEATURE:
<221> NAME/KEY: misc_feature
<222> LOCATION: (1618)..(1618)
<223> OTHER INFORMATION: n is a, c, g, or t
<220> FEATURE:
<221> NAME/KEY: misc_feature
<222> LOCATION: (1621)..(1621)
<223> OTHER INFORMATION: n is a, c, g, or t
<220> FEATURE:
<221> NAME/KEY: misc_feature
<222> LOCATION: (1624)..(1624)
<223> OTHER INFORMATION: n is a, c, g, or t
<220> FEATURE:
<221> NAME/KEY: misc_feature
<222> LOCATION: (1627)..(1630)
<223> OTHER INFORMATION: n is a, c, g, or t
<220> FEATURE:
<221> NAME/KEY: misc_feature
<222> LOCATION: (1633)..(1636)
<223> OTHER INFORMATION: n is a, c, g, or t
<220> FEATURE:
<221> NAME/KEY: misc_feature
<222> LOCATION: (1639)..(1639)
<223> OTHER INFORMATION: n is a, c, g, or t
<220> FEATURE:
<221> NAME/KEY: misc_feature
<222> LOCATION: (1643)..(1645)
<223> OTHER INFORMATION: n is a, c, g, or t
<220> FEATURE:
<221> NAME/KEY: misc_feature
<222> LOCATION: (1656)..(1656)
<223> OTHER INFORMATION: n is a, c, g, or t
<220> FEATURE:
<221> NAME/KEY: misc_feature
<222> LOCATION: (1658)..(1658)
<223> OTHER INFORMATION: n is a, c, g, or t
<220> FEATURE:
<221> NAME/KEY: misc_feature
<222> LOCATION: (1660)..(1660)

<223> OTHER INFORMATION: n is a, c, g, or t
<220> FEATURE:
<221> NAME/KEY: misc_feature
<222> LOCATION: (1662)..(1662)
<223> OTHER INFORMATION: n is a, c, g, or t
<220> FEATURE:
<221> NAME/KEY: misc_feature
<222> LOCATION: (1664)..(1667)
<223> OTHER INFORMATION: n is a, c, g, or t
<220> FEATURE:
<221> NAME/KEY: misc_feature
<222> LOCATION: (1669)..(1671)
<223> OTHER INFORMATION: n is a, c, g, or t
<220> FEATURE:
<221> NAME/KEY: misc_feature
<222> LOCATION: (1673)..(1674)
<223> OTHER INFORMATION: n is a, c, g, or t
<220> FEATURE:
<221> NAME/KEY: misc_feature
<222> LOCATION: (1677)..(1677)
<223> OTHER INFORMATION: n is a, c, g, or t
<220> FEATURE:
<221> NAME/KEY: misc_feature
<222> LOCATION: (1685)..(1685)
<223> OTHER INFORMATION: n is a, c, g, or t
<220> FEATURE:
<221> NAME/KEY: misc_feature
<222> LOCATION: (1687)..(1690)
<223> OTHER INFORMATION: n is a, c, g, or t
<220> FEATURE:
<221> NAME/KEY: misc_feature
<222> LOCATION: (1692)..(1694)
<223> OTHER INFORMATION: n is a, c, g, or t
<220> FEATURE:
<221> NAME/KEY: misc_feature
<222> LOCATION: (1696)..(1696)
<223> OTHER INFORMATION: n is a, c, g, or t
<220> FEATURE:
<221> NAME/KEY: misc_feature
<222> LOCATION: (1700)..(1700)
<223> OTHER INFORMATION: n is a, c, g, or t
<220> FEATURE:
<221> NAME/KEY: misc_feature
<222> LOCATION: (1703)..(1707)
<223> OTHER INFORMATION: n is a, c, g, or t
<220> FEATURE:
<221> NAME/KEY: misc_feature
<222> LOCATION: (1712)..(1717)
<223> OTHER INFORMATION: n is a, c, g, or t
<220> FEATURE:
<221> NAME/KEY: misc_feature
<222> LOCATION: (1720)..(1721)
<223> OTHER INFORMATION: n is a, c, g, or t
<220> FEATURE:
<221> NAME/KEY: misc_feature
<222> LOCATION: (1725)..(1727)
<223> OTHER INFORMATION: n is a, c, g, or t
<220> FEATURE:
<221> NAME/KEY: misc_feature
<222> LOCATION: (1731)..(1731)
<223> OTHER INFORMATION: n is a, c, g, or t
<220> FEATURE:
<221> NAME/KEY: misc_feature
<222> LOCATION: (1734)..(1734)
<223> OTHER INFORMATION: n is a, c, g, or t
<220> FEATURE:
<221> NAME/KEY: misc_feature
<222> LOCATION: (1740)..(1740)
<223> OTHER INFORMATION: n is a, c, g, or t
<220> FEATURE:
<221> NAME/KEY: misc_feature
<222> LOCATION: (1744)..(1747)
<223> OTHER INFORMATION: n is a, c, g, or t
<220> FEATURE:
<221> NAME/KEY: misc_feature
<222> LOCATION: (1750)..(1753)
<223> OTHER INFORMATION: n is a, c, g, or t
<220> FEATURE:
<221> NAME/KEY: misc_feature
<222> LOCATION: (1755)..(1755)
<223> OTHER INFORMATION: n is a, c, g, or t
<220> FEATURE:
<221> NAME/KEY: misc_feature
<222> LOCATION: (1757)..(1757)
<223> OTHER INFORMATION: n is a, c, g, or t
<220> FEATURE:
<221> NAME/KEY: misc_feature
<222> LOCATION: (1760)..(1761)
<223> OTHER INFORMATION: n is a, c, g, or t
<220> FEATURE:
<221> NAME/KEY: misc_feature
<222> LOCATION: (1763)..(1764)
<223> OTHER INFORMATION: n is a, c, g, or t
<220> FEATURE:
<221> NAME/KEY: misc_feature
<222> LOCATION: (1770)..(1772)
<223> OTHER INFORMATION: n is a, c, g, or t
<220> FEATURE:
<221> NAME/KEY: misc_feature
<222> LOCATION: (1774)..(1774)
<223> OTHER INFORMATION: n is a, c, g, or t
<220> FEATURE:
<221> NAME/KEY: misc_feature
<222> LOCATION: (1776)..(1777)
<223> OTHER INFORMATION: n is a, c, g, or t
<220> FEATURE:
<221> NAME/KEY: misc_feature
<222> LOCATION: (1779)..(1781)
<223> OTHER INFORMATION: n is a, c, g, or t
<220> FEATURE:
<221> NAME/KEY: misc_feature
<222> LOCATION: (1786)..(1787)
<223> OTHER INFORMATION: n is a, c, g, or t
<220> FEATURE:
<221> NAME/KEY: misc_feature
<222> LOCATION: (1789)..(1790)
<223> OTHER INFORMATION: n is a, c, g, or t
<220> FEATURE:
<221> NAME/KEY: misc_feature
<222> LOCATION: (1793)..(1794)
<223> OTHER INFORMATION: n is a, c, g, or t
<220> FEATURE:
<221> NAME/KEY: misc_feature
<222> LOCATION: (1799)..(1799)
<223> OTHER INFORMATION: n is a, c, g, or t
<220> FEATURE:
<221> NAME/KEY: misc_feature
<222> LOCATION: (1803)..(1812)
<223> OTHER INFORMATION: n is a, c, g, or t
<220> FEATURE:
<221> NAME/KEY: misc_feature
<222> LOCATION: (1814)..(1814)
<223> OTHER INFORMATION: n is a, c, g, or t
<220> FEATURE:
<221> NAME/KEY: misc_feature
<222> LOCATION: (1817)..(1819)
<223> OTHER INFORMATION: n is a, c, g, or t
<220> FEATURE:
<221> NAME/KEY: misc_feature
<222> LOCATION: (1821)..(1825)
<223> OTHER INFORMATION: n is a, c, g, or t
<220> FEATURE:
<221> NAME/KEY: misc_feature
<222> LOCATION: (1828)..(1828)
<223> OTHER INFORMATION: n is a, c, g, or t
<220> FEATURE:
<221> NAME/KEY: misc_feature
<222> LOCATION: (1830)..(1830)
<223> OTHER INFORMATION: n is a, c, g, or t
<220> FEATURE:
<221> NAME/KEY: misc_feature
<222> LOCATION: (1836)..(1838)
<223> OTHER INFORMATION: n is a, c, g, or t
<220> FEATURE:
<221> NAME/KEY: misc_feature
<222> LOCATION: (1840)..(1840)
<223> OTHER INFORMATION: n is a, c, g, or t
<220> FEATURE:

-continued

<221> NAME/KEY: misc_feature
<222> LOCATION: (1848)..(1850)
<223> OTHER INFORMATION: n is a, c, g, or t
<220> FEATURE:
<221> NAME/KEY: misc_feature
<222> LOCATION: (1854)..(1856)
<223> OTHER INFORMATION: n is a, c, g, or t
<220> FEATURE:
<221> NAME/KEY: misc_feature
<222> LOCATION: (1858)..(1858)
<223> OTHER INFORMATION: n is a, c, g, or t
<220> FEATURE:
<221> NAME/KEY: misc_feature
<222> LOCATION: (1863)..(1866)
<223> OTHER INFORMATION: n is a, c, g, or t
<220> FEATURE:
<221> NAME/KEY: misc_feature
<222> LOCATION: (1868)..(1870)
<223> OTHER INFORMATION: n is a, c, g, or t
<220> FEATURE:
<221> NAME/KEY: misc_feature
<222> LOCATION: (1872)..(1873)
<223> OTHER INFORMATION: n is a, c, g, or t
<220> FEATURE:
<221> NAME/KEY: misc_feature
<222> LOCATION: (1875)..(1876)
<223> OTHER INFORMATION: n is a, c, g, or t
<220> FEATURE:
<221> NAME/KEY: misc_feature
<222> LOCATION: (1880)..(1881)
<223> OTHER INFORMATION: n is a, c, g, or t
<220> FEATURE:
<221> NAME/KEY: misc_feature
<222> LOCATION: (1884)..(1888)
<223> OTHER INFORMATION: n is a, c, g, or t
<220> FEATURE:
<221> NAME/KEY: misc_feature
<222> LOCATION: (1890)..(1894)
<223> OTHER INFORMATION: n is a, c, g, or t
<220> FEATURE:
<221> NAME/KEY: misc_feature
<222> LOCATION: (1904)..(1904)
<223> OTHER INFORMATION: n is a, c, g, or t
<220> FEATURE:
<221> NAME/KEY: misc_feature
<222> LOCATION: (1906)..(1906)
<223> OTHER INFORMATION: n is a, c, g, or t
<220> FEATURE:
<221> NAME/KEY: misc_feature
<222> LOCATION: (1909)..(1910)
<223> OTHER INFORMATION: n is a, c, g, or t
<220> FEATURE:
<221> NAME/KEY: misc_feature
<222> LOCATION: (1912)..(1912)
<223> OTHER INFORMATION: n is a, c, g, or t
<220> FEATURE:
<221> NAME/KEY: misc_feature
<222> LOCATION: (1915)..(1916)
<223> OTHER INFORMATION: n is a, c, g, or t
<220> FEATURE:
<221> NAME/KEY: misc_feature
<222> LOCATION: (1918)..(1918)
<223> OTHER INFORMATION: n is a, c, g, or t
<220> FEATURE:
<221> NAME/KEY: misc_feature
<222> LOCATION: (1926)..(1927)
<223> OTHER INFORMATION: n is a, c, g, or t
<220> FEATURE:
<221> NAME/KEY: misc_feature
<222> LOCATION: (1933)..(1933)
<223> OTHER INFORMATION: n is a, c, g, or t
<220> FEATURE:
<221> NAME/KEY: misc_feature
<222> LOCATION: (1940)..(1945)
<223> OTHER INFORMATION: n is a, c, g, or t
<220> FEATURE:
<221> NAME/KEY: misc_feature
<222> LOCATION: (1949)..(1952)
<223> OTHER INFORMATION: n is a, c, g, or t -continued
<220> FEATURE:
<221> NAME/KEY: misc_feature
<222> LOCATION: (1954)..(1955)
<223> OTHER INFORMATION: n is a, c, g, or t
<220> FEATURE:
<221> NAME/KEY: misc_feature
<222> LOCATION: (1958)..(1960)
<223> OTHER INFORMATION: n is a, c, g, or t
<220> FEATURE:
<221> NAME/KEY: misc_feature
<222> LOCATION: (1964)..(1964)
<223> OTHER INFORMATION: n is a, c, g, or t
<220> FEATURE:
<221> NAME/KEY: misc_feature
<222> LOCATION: (1966)..(1966)
<223> OTHER INFORMATION: n is a, c, g, or t
<220> FEATURE:
<221> NAME/KEY: misc_feature
<222> LOCATION: (1969)..(1969)
<223> OTHER INFORMATION: n is a, c, g, or t
<220> FEATURE:
<221> NAME/KEY: misc_feature
<222> LOCATION: (1972)..(1972)
<223> OTHER INFORMATION: n is a, c, g, or t
<220> FEATURE:
<221> NAME/KEY: misc_feature
<222> LOCATION: (1976)..(1976)
<223> OTHER INFORMATION: n is a, c, g, or t
<220> FEATURE:
<221> NAME/KEY: misc_feature
<222> LOCATION: (1978)..(1978)
<223> OTHER INFORMATION: n is a, c, g, or t
<220> FEATURE:
<221> NAME/KEY: misc_feature
<222> LOCATION: (1982)..(1987)
<223> OTHER INFORMATION: n is a, c, g, or t
<220> FEATURE:
<221> NAME/KEY: misc_feature
<222> LOCATION: (1989)..(1990)
<223> OTHER INFORMATION: n is a, c, g, or t
<220> FEATURE:
<221> NAME/KEY: misc_feature
<222> LOCATION: (1993)..(1994)
<223> OTHER INFORMATION: n is a, c, g, or t
<220> FEATURE:
<221> NAME/KEY: misc_feature
<222> LOCATION: (1996)..(1996)
<223> OTHER INFORMATION: n is a, c, g, or t
<220> FEATURE:
<221> NAME/KEY: misc_feature
<222> LOCATION: (2006)..(2006)
<223> OTHER INFORMATION: n is a, c, g, or t
<220> FEATURE:
<221> NAME/KEY: misc_feature
<222> LOCATION: (2013)..(2015)
<223> OTHER INFORMATION: n is a, c, g, or t
<220> FEATURE:
<221> NAME/KEY: misc_feature
<222> LOCATION: (2017)..(2017)
<223> OTHER INFORMATION: n is a, c, g, or t
<220> FEATURE:
<221> NAME/KEY: misc_feature
<222> LOCATION: (2021)..(2023)
<223> OTHER INFORMATION: n is a, c, g, or t
<220> FEATURE:
<221> NAME/KEY: misc_feature
<222> LOCATION: (2026)..(2026)
<223> OTHER INFORMATION: n is a, c, g, or t
<220> FEATURE:
<221> NAME/KEY: misc_feature
<222> LOCATION: (2030)..(2030)
<223> OTHER INFORMATION: n is a, c, g, or t
<220> FEATURE:
<221> NAME/KEY: misc_feature
<222> LOCATION: (2035)..(2038)
<223> OTHER INFORMATION: n is a, c, g, or t
<220> FEATURE:
<221> NAME/KEY: misc_feature
<222> LOCATION: (2041)..(2044)

-continued

<223> OTHER INFORMATION: n is a, c, g, or t
<220> FEATURE:
<221> NAME/KEY: misc_feature
<222> LOCATION: (2048)..(2050)
<223> OTHER INFORMATION: n is a, c, g, or t
<220> FEATURE:
<221> NAME/KEY: misc_feature
<222> LOCATION: (2053)..(2053)
<223> OTHER INFORMATION: n is a, c, g, or t
<220> FEATURE:
<221> NAME/KEY: misc_feature
<222> LOCATION: (2056)..(2056)
<223> OTHER INFORMATION: n is a, c, g, or t
<220> FEATURE:
<221> NAME/KEY: misc_feature
<222> LOCATION: (2060)..(2061)
<223> OTHER INFORMATION: n is a, c, g, or t
<220> FEATURE:
<221> NAME/KEY: misc_feature
<222> LOCATION: (2063)..(2064)
<223> OTHER INFORMATION: n is a, c, g, or t
<220> FEATURE:
<221> NAME/KEY: misc_feature
<222> LOCATION: (2073)..(2073)
<223> OTHER INFORMATION: n is a, c, g, or t
<220> FEATURE:
<221> NAME/KEY: misc_feature
<222> LOCATION: (2077)..(2078)
<223> OTHER INFORMATION: n is a, c, g, or t
<220> FEATURE:
<221> NAME/KEY: misc_feature
<222> LOCATION: (2080)..(2081)
<223> OTHER INFORMATION: n is a, c, g, or t
<220> FEATURE:
<221> NAME/KEY: misc_feature
<222> LOCATION: (2086)..(2086)
<223> OTHER INFORMATION: n is a, c, g, or t
<220> FEATURE:
<221> NAME/KEY: misc_feature
<222> LOCATION: (2095)..(2096)
<223> OTHER INFORMATION: n is a, c, g, or t
<220> FEATURE:
<221> NAME/KEY: misc_feature
<222> LOCATION: (2098)..(2099)
<223> OTHER INFORMATION: n is a, c, g, or t
<220> FEATURE:
<221> NAME/KEY: misc_feature
<222> LOCATION: (2101)..(2104)
<223> OTHER INFORMATION: n is a, c, g, or t
<220> FEATURE:
<221> NAME/KEY: misc_feature
<222> LOCATION: (2107)..(2107)
<223> OTHER INFORMATION: n is a, c, g, or t
<220> FEATURE:
<221> NAME/KEY: misc_feature
<222> LOCATION: (2110)..(2110)
<223> OTHER INFORMATION: n is a, c, g, or t
<220> FEATURE:
<221> NAME/KEY: misc_feature
<222> LOCATION: (2112)..(2112)
<223> OTHER INFORMATION: n is a, c, g, or t
<220> FEATURE:
<221> NAME/KEY: misc_feature
<222> LOCATION: (2114)..(2114)
<223> OTHER INFORMATION: n is a, c, g, or t
<220> FEATURE:
<221> NAME/KEY: misc_feature
<222> LOCATION: (2116)..(2116)
<223> OTHER INFORMATION: n is a, c, g, or t
<220> FEATURE:
<221> NAME/KEY: misc_feature
<222> LOCATION: (2119)..(2119)
<223> OTHER INFORMATION: n is a, c, g, or t
<220> FEATURE:
<221> NAME/KEY: misc_feature
<222> LOCATION: (2127)..(2134)
<223> OTHER INFORMATION: n is a, c, g, or t
<220> FEATURE:
<221> NAME/KEY: misc_feature
<222> LOCATION: (2136)..(2136)
<223> OTHER INFORMATION: n is a, c, g, or t
<220> FEATURE:
<221> NAME/KEY: misc_feature
<222> LOCATION: (2138)..(2139)
<223> OTHER INFORMATION: n is a, c, g, or t
<220> FEATURE:
<221> NAME/KEY: misc_feature
<222> LOCATION: (2142)..(2143)
<223> OTHER INFORMATION: n is a, c, g, or t
<220> FEATURE:
<221> NAME/KEY: misc_feature
<222> LOCATION: (2149)..(2149)
<223> OTHER INFORMATION: n is a, c, g, or t
<220> FEATURE:
<221> NAME/KEY: misc_feature
<222> LOCATION: (2155)..(2155)
<223> OTHER INFORMATION: n is a, c, g, or t
<220> FEATURE:
<221> NAME/KEY: misc_feature
<222> LOCATION: (2158)..(2160)
<223> OTHER INFORMATION: n is a, c, g, or t
<220> FEATURE:
<221> NAME/KEY: misc_feature
<222> LOCATION: (2162)..(2165)
<223> OTHER INFORMATION: n is a, c, g, or t
<220> FEATURE:
<221> NAME/KEY: misc_feature
<222> LOCATION: (2167)..(2167)
<223> OTHER INFORMATION: n is a, c, g, or t
<220> FEATURE:
<221> NAME/KEY: misc_feature
<222> LOCATION: (2171)..(2171)
<223> OTHER INFORMATION: n is a, c, g, or t
<220> FEATURE:
<221> NAME/KEY: misc_feature
<222> LOCATION: (2173)..(2175)
<223> OTHER INFORMATION: n is a, c, g, or t
<220> FEATURE:
<221> NAME/KEY: misc_feature
<222> LOCATION: (2177)..(2180)
<223> OTHER INFORMATION: n is a, c, g, or t
<220> FEATURE:
<221> NAME/KEY: misc_feature
<222> LOCATION: (2182)..(2182)
<223> OTHER INFORMATION: n is a, c, g, or t
<220> FEATURE:
<221> NAME/KEY: misc_feature
<222> LOCATION: (2184)..(2185)
<223> OTHER INFORMATION: n is a, c, g, or t
<220> FEATURE:
<221> NAME/KEY: misc_feature
<222> LOCATION: (2189)..(2189)
<223> OTHER INFORMATION: n is a, c, g, or t
<220> FEATURE:
<221> NAME/KEY: misc_feature
<222> LOCATION: (2193)..(2193)
<223> OTHER INFORMATION: n is a, c, g, or t
<220> FEATURE:
<221> NAME/KEY: misc_feature
<222> LOCATION: (2195)..(2198)
<223> OTHER INFORMATION: n is a, c, g, or t
<220> FEATURE:
<221> NAME/KEY: misc_feature
<222> LOCATION: (2200)..(2200)
<223> OTHER INFORMATION: n is a, c, g, or t
<220> FEATURE:
<221> NAME/KEY: misc_feature
<222> LOCATION: (2204)..(2206)
<223> OTHER INFORMATION: n is a, c, g, or t
<220> FEATURE:
<221> NAME/KEY: misc_feature
<222> LOCATION: (2212)..(2215)
<223> OTHER INFORMATION: n is a, c, g, or t
<220> FEATURE:
<221> NAME/KEY: misc_feature
<222> LOCATION: (2220)..(2221)
<223> OTHER INFORMATION: n is a, c, g, or t
<220> FEATURE:

<221> NAME/KEY: misc_feature
<222> LOCATION: (2224)..(2225)
<223> OTHER INFORMATION: n is a, c, g, or t
<220> FEATURE:
<221> NAME/KEY: misc_feature
<222> LOCATION: (2236)..(2236)
<223> OTHER INFORMATION: n is a, c, g, or t
<220> FEATURE:
<221> NAME/KEY: misc_feature
<222> LOCATION: (2239)..(2239)
<223> OTHER INFORMATION: n is a, c, g, or t
<220> FEATURE:
<221> NAME/KEY: misc_feature
<222> LOCATION: (2243)..(2250)
<223> OTHER INFORMATION: n is a, c, g, or t
<220> FEATURE:
<221> NAME/KEY: misc_feature
<222> LOCATION: (2254)..(2254)
<223> OTHER INFORMATION: n is a, c, g, or t
<220> FEATURE:
<221> NAME/KEY: misc_feature
<222> LOCATION: (2264)..(2264)
<223> OTHER INFORMATION: n is a, c, g, or t
<220> FEATURE:
<221> NAME/KEY: misc_feature
<222> LOCATION: (2266)..(2266)
<223> OTHER INFORMATION: n is a, c, g, or t
<220> FEATURE:
<221> NAME/KEY: misc_feature
<222> LOCATION: (2269)..(2269)
<223> OTHER INFORMATION: n is a, c, g, or t
<220> FEATURE:
<221> NAME/KEY: misc_feature
<222> LOCATION: (2276)..(2278)
<223> OTHER INFORMATION: n is a, c, g, or t
<220> FEATURE:
<221> NAME/KEY: misc_feature
<222> LOCATION: (2288)..(2289)
<223> OTHER INFORMATION: n is a, c, g, or t
<220> FEATURE:
<221> NAME/KEY: misc_feature
<222> LOCATION: (2292)..(2292)
<223> OTHER INFORMATION: n is a, c, g, or t
<220> FEATURE:
<221> NAME/KEY: misc_feature
<222> LOCATION: (2294)..(2295)
<223> OTHER INFORMATION: n is a, c, g, or t
<220> FEATURE:
<221> NAME/KEY: misc_feature
<222> LOCATION: (2298)..(2298)
<223> OTHER INFORMATION: n is a, c, g, or t
<220> FEATURE:
<221> NAME/KEY: misc_feature
<222> LOCATION: (2300)..(2300)
<223> OTHER INFORMATION: n is a, c, g, or t
<220> FEATURE:
<221> NAME/KEY: misc_feature
<222> LOCATION: (2303)..(2304)
<223> OTHER INFORMATION: n is a, c, g, or t
<220> FEATURE:
<221> NAME/KEY: misc_feature
<222> LOCATION: (2307)..(2307)
<223> OTHER INFORMATION: n is a, c, g, or t
<220> FEATURE:
<221> NAME/KEY: misc_feature
<222> LOCATION: (2376)..(2376)
<223> OTHER INFORMATION: n is a, c, g, or t
<220> FEATURE:
<221> NAME/KEY: misc_feature
<222> LOCATION: (2383)..(2383)
<223> OTHER INFORMATION: n is a, c, g, or t
<220> FEATURE:
<221> NAME/KEY: misc_feature
<222> LOCATION: (2385)..(2386)
<223> OTHER INFORMATION: n is a, c, g, or t
<220> FEATURE:
<221> NAME/KEY: misc_feature
<222> LOCATION: (2390)..(2390)
<223> OTHER INFORMATION: n is a, c, g, or t
<220> FEATURE:
<221> NAME/KEY: misc_feature
<222> LOCATION: (2392)..(2393)
<223> OTHER INFORMATION: n is a, c, g, or t
<220> FEATURE:
<221> NAME/KEY: misc_feature
<222> LOCATION: (2395)..(2395)
<223> OTHER INFORMATION: n is a, c, g, or t
<220> FEATURE:
<221> NAME/KEY: misc_feature
<222> LOCATION: (2397)..(2397)
<223> OTHER INFORMATION: n is a, c, g, or t
<220> FEATURE:
<221> NAME/KEY: misc_feature
<222> LOCATION: (2405)..(2405)
<223> OTHER INFORMATION: n is a, c, g, or t
<220> FEATURE:
<221> NAME/KEY: misc_feature
<222> LOCATION: (2414)..(2414)
<223> OTHER INFORMATION: n is a, c, g, or t
<220> FEATURE:
<221> NAME/KEY: misc_feature
<222> LOCATION: (2417)..(2417)
<223> OTHER INFORMATION: n is a, c, g, or t
<220> FEATURE:
<221> NAME/KEY: misc_feature
<222> LOCATION: (2422)..(2426)
<223> OTHER INFORMATION: n is a, c, g, or t
<220> FEATURE:
<221> NAME/KEY: misc_feature
<222> LOCATION: (2430)..(2430)
<223> OTHER INFORMATION: n is a, c, g, or t

<400> SEQUENCE: 18
nnnnnccgng nggnnnctat tccatcacca ttctagcctg tacacagana ngtcgctcnn 60
gnnnnncgna ncnnnnnncn tcnnncnnnn ntnntnnaan ncntcaccca gngngncnna 120
ngccncnagg cgnggtnncc nncnnnnnnn nagtnnactg agactcatnc nngtacaggg 180
gggtacgtca ncangtacag gggggtacgt cancangtac agggggtac gtcatcatgt 240 acanngnggn nnnncaccan gtacaggggg gtacgtcacc nngtacaggg gggtacgtca 300
cagccaatca naannnnnca cgnngcnnna nngncnntnn gnnnnnngnn gnnnnnannn 360
tnnnnatata nnnagngcac ataccggncg gcngtaggta tntcnnnngg cggtcnnggn 420
gnntgcacgg nnncngngnn nancnngccg ctgggggcag tgaatngncg cttagncnag 480
aggggcaacn tgggcccagc ggagccgnnt ccangggcaa gnnantnnan nnnnaccccc 540
cgctctcnnn gangagcaac aactactcnn ncngnacnat naacggnntn cnngcnncca 600
acaagttcnn nnccgnnngn annnncnnnc tnnanagaga tccnnattgg tatcgnnnna 660
antanaatna ctctatcgct nnntggctnc gcnantgnnc gcgntcncac gnnnagatct 720
gcanctgcgg acnatnnagn anncactggt tncangannn tnnnggactt gnnnnncnnn 780
nnacccannc ggacnnnctc gnnnnagnnn tncnncgncn ncnccgagna naggnnaagc 840
gagcnaaaag aaancttgat taccnnnann nnnancngac cccgaacnnn aaaaangcgt 900
ataagactgt aanatggcaa gactacgann nngnngaccn ngnggncgnt ttnnctnctn 960
cnnnagagga cgntggcacn nnnnnnanng actncgacga aganncttatt cccggagggg 1020 taaatttcga natnngngna gannnnnntn tnntngncgn gntnnnagga ngnnctttca 1080
caacccncnc ccnggnncnt atnnngtnag gctnccgaac ccnnaatcta nnntnacnnt 1140
cnnnttccaa ggnntnntnt tnntnncgga ngnncnnnnt ntnnntaaaa ncancnnagc 1200
ggggggctan nnagacnann nntacggnnn gnnatgtngc cnnnatnnnt gtnaacctnn 1260
naganttnnt gctngcnnca atgnnnntnn nnnnnnngag caaaatcgga ggcccnancn 1320

```
cnnntnnnnn gnnnnngnan gggtnnnaat ggtcagcaca ancnncgnan nantggcntn   1380

nnngnnngcn gcgggcangn naganannaa nnnncccnnc gnnncaccnn nngnntggtg   1440

gngntgggcn ntnntgntga tgcanccnan ngnnnctngc ngnttntnna atnncccaaa   1500

gcnnatgacn ctgnangnna tgggnnncnt gttngggggc tggcanctnt tcngncannt   1560

nnaaaccnnn ttnnnnntnc tngcnactan gnnnnanggn ncnttcnnnc cngtngcnag   1620

nctnctnnnn cannnngant acnnnagcag gaggcncntn gngnnnntnn nanntanagg   1680

tgcancnnnn annngnaccn tgnnnnnaaa annnnnncan nacgnnnacg nggngtccan   1740

tgcnnnngcn nnngngnaan ngnnacccgn nnancnncnn nacccnncnn tgnncccana   1800

ccnnnnnnnn nncnccnnna nnnnngcncn aggcannnan cggcttgnnn gctnnnanag   1860

cannnnannn tnntnntcan nggnnnnntn nnnnagcttt gcancnctnn cngcnntngg   1920

tgcacnntgg tcntttcctn nnnnncaann nncnnttnnn agangntcnt tnaacnanca   1980

cnnnnnnann ggnncngggg accccnaggg ccnnngntgg nnnacncttn tgccnnnngg   2040

nnnngagnnn atnacngacn ncnncatgtc agnaccnncn ncaganctgg acacnnannt   2100

nnnnacnctn tncntngcnc aaggcannnn nnnntngnna cnntacaant tcggnacnnn   2160

tnnnnangcg ntnnngnnnn cngnnatgna gancnnnncn tggnnngtgg tnnnngtccn   2220

ntcnntctgg cagctnggna acnnnnnnnn gccntaccca tggnangtna actggnnnaa   2280

cgagcacnnt gnanngggncn ganncanccc tgaaaagggg gggggctaa agcccccccc   2340

ccttaaaccc cccctgggg gggattcccc cccagncccc ccntnnatan annantnaat   2400

aaacncagaa aatngantta tnnnnntatn tt                                 2432
```

```
<210> SEQ ID NO 19
<211> LENGTH: 470
<212> TYPE: PRT
<213> ORGANISM: artificial
<220> FEATURE:
<223> OTHER INFORMATION: consensus between CAV P54088 and HGyV VP1
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (14)..(17)
<223> OTHER INFORMATION: Xaa can be any naturally occurring amino acid
<220> FEATURE:
<221> NAME/KEY: misc_feature
<222> LOCATION: (23)..(25)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (40)..(41)
<223> OTHER INFORMATION: Xaa can be any naturally occurring amino acid
<220> FEATURE:
<221> NAME/KEY: misc_feature
<222> LOCATION: (44)..(47)
<223> OTHER INFORMATION: Xaa can be any naturally occurring amino acid
<220> FEATURE:
<221> NAME/KEY: misc_feature
<222> LOCATION: (50)..(51)
<223> OTHER INFORMATION: Xaa can be any naturally occurring amino acid
<220> FEATURE:
<221> NAME/KEY: misc_feature
<222> LOCATION: (53)..(54)
<223> OTHER INFORMATION: Xaa can be any naturally occurring amino acid
<220> FEATURE:
<221> NAME/KEY: misc_feature
```

```
<222> LOCATION: (59)..(59)
<223> OTHER INFORMATION: Xaa can be any naturally occurring amino acid
<220> FEATURE:
<221> NAME/KEY: misc_feature
<222> LOCATION: (62)..(62)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (71)..(74)
<223> OTHER INFORMATION: Xaa can be any naturally occurring amino acid
<220> FEATURE:
<221> NAME/KEY: misc_feature
<222> LOCATION: (76)..(77)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (84)..(85)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid
<220> FEATURE:
<221> NAME/KEY: misc_feature
<222> LOCATION: (93)..(96)
<223> OTHER INFORMATION: Xaa can be any naturally occurring amino acid
<220> FEATURE:
<221> NAME/KEY: misc_feature
<222> LOCATION: (100)..(102)
<223> OTHER INFORMATION: Xaa can be any naturally occurring amino acid
<220> FEATURE:
<221> NAME/KEY: misc_feature
<222> LOCATION: (104)..(107)
<223> OTHER INFORMATION: Xaa can be any naturally occurring amino acid
<220> FEATURE:
<221> NAME/KEY: misc_feature
<222> LOCATION: (110)..(110)
<223> OTHER INFORMATION: Xaa can be any naturally occurring amino acid
<220> FEATURE:
<221> NAME/KEY: misc_feature
<222> LOCATION: (112)..(112)
<223> OTHER INFORMATION: Xaa can be any naturally occurring amino acid
<220> FEATURE:
<221> NAME/KEY: misc_feature
<222> LOCATION: (116)..(116)
<223> OTHER INFORMATION: Xaa can be any naturally occurring amino acid
<220> FEATURE:
<221> NAME/KEY: misc_feature
<222> LOCATION: (119)..(119)
<223> OTHER INFORMATION: Xaa can be any naturally occurring amino acid
<220> FEATURE:
<221> NAME/KEY: misc_feature
<222> LOCATION: (122)..(122)
<223> OTHER INFORMATION: Xaa can be any naturally occurring amino acid
<220> FEATURE:
<221> NAME/KEY: misc_feature
<222> LOCATION: (124)..(124)
<223> OTHER INFORMATION: Xaa can be any naturally occurring amino acid
<220> FEATURE:
<221> NAME/KEY: misc_feature
<222> LOCATION: (126)..(128)
<223> OTHER INFORMATION: Xaa can be any naturally occurring amino acid
<220> FEATURE:
<221> NAME/KEY: misc_feature
<222> LOCATION: (135)..(142)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
```

<221> NAME/KEY: misc_feature
<222> LOCATION: (148)..(148)
<223> OTHER INFORMATION: Xaa can be any naturally occurring amino acid
<220> FEATURE:
<221> NAME/KEY: misc_feature
<222> LOCATION: (150)..(151)
<223> OTHER INFORMATION: Xaa can be any naturally occurring amino acid
<220> FEATURE:
<221> NAME/KEY: misc_feature
<222> LOCATION: (153)..(153)
<223> OTHER INFORMATION: Xaa can be any naturally occurring amino acid
<220> FEATURE:
<221> NAME/KEY: misc_feature
<222> LOCATION: (157)..(166)
<223> OTHER INFORMATION: Xaa can be any naturally occurring amino acid
<220> FEATURE:
<221> NAME/KEY: misc_feature
<222> LOCATION: (169)..(170)
<223> OTHER INFORMATION: Xaa can be any naturally occurring amino acid
<220> FEATURE:
<221> NAME/KEY: misc_feature
<222> LOCATION: (173)..(173)
<223> OTHER INFORMATION: Xaa can be any naturally occurring amino acid
<220> FEATURE:
<221> NAME/KEY: misc_feature
<222> LOCATION: (180)..(181)
<223> OTHER INFORMATION: Xaa can be any naturally occurring amino acid
<220> FEATURE:
<221> NAME/KEY: misc_feature
<222> LOCATION: (183)..(183)
<223> OTHER INFORMATION: Xaa can be any naturally occurring amino acid
<220> FEATURE:
<221> NAME/KEY: misc_feature
<222> LOCATION: (185)..(188)
<223> OTHER INFORMATION: Xaa can be any naturally occurring amino acid
<220> FEATURE:
<221> NAME/KEY: misc_feature
<222> LOCATION: (191)..(191)
<223> OTHER INFORMATION: Xaa can be any naturally occurring amino acid
<220> FEATURE:
<221> NAME/KEY: misc_feature
<222> LOCATION: (193)..(193)
<223> OTHER INFORMATION: Xaa can be any naturally occurring amino acid
<220> FEATURE:
<221> NAME/KEY: misc_feature
<222> LOCATION: (196)..(196)
<223> OTHER INFORMATION: Xaa can be any naturally occurring amino acid
<220> FEATURE:
<221> NAME/KEY: misc_feature
<222> LOCATION: (200)..(201)
<223> OTHER INFORMATION: Xaa can be any naturally occurring amino acid
<220> FEATURE:
<221> NAME/KEY: misc_feature
<222> LOCATION: (204)..(206)
<223> OTHER INFORMATION: Xaa can be any naturally occurring amino acid
<220> FEATURE:
<221> NAME/KEY: misc_feature
<222> LOCATION: (210)..(210)
<223> OTHER INFORMATION: Xaa can be any naturally occurring amino acid
<220> FEATURE:
<221> NAME/KEY: misc_feature
<222> LOCATION: (215)..(216)
<223> OTHER INFORMATION: Xaa can be any naturally occurring amino acid
<220> FEATURE:
<221> NAME/KEY: misc_feature
<222> LOCATION: (218)..(218)
<223> OTHER INFORMATION: Xaa can be any naturally occurring amino acid
<220> FEATURE:
<221> NAME/KEY: misc_feature
<222> LOCATION: (220)..(221)
<223> OTHER INFORMATION: Xaa can be any naturally occurring amino acid
<220> FEATURE:
<221> NAME/KEY: misc_feature
<222> LOCATION: (225)..(227)
<223> OTHER INFORMATION: Xaa can be any naturally occurring amino acid
<220> FEATURE:
<221> NAME/KEY: misc_feature
<222> LOCATION: (229)..(229)
<223> OTHER INFORMATION: Xaa can be any naturally occurring amino acid
<220> FEATURE:
<221> NAME/KEY: misc_feature
<222> LOCATION: (238)..(238)
<223> OTHER INFORMATION: Xaa can be any naturally occurring amino acid
<220> FEATURE:
<221> NAME/KEY: misc_feature
<222> LOCATION: (240)..(241)
<223> OTHER INFORMATION: Xaa can be any naturally occurring amino acid
<220> FEATURE:
<221> NAME/KEY: misc_feature
<222> LOCATION: (243)..(244)
<223> OTHER INFORMATION: Xaa can be any naturally occurring amino acid
<220> FEATURE:
<221> NAME/KEY: misc_feature
<222> LOCATION: (247)..(247)
<223> OTHER INFORMATION: Xaa can be any naturally occurring amino acid
<220> FEATURE:
<221> NAME/KEY: misc_feature
<222> LOCATION: (252)..(252)
<223> OTHER INFORMATION: Xaa can be any naturally occurring amino acid
<220> FEATURE:
<221> NAME/KEY: misc_feature
<222> LOCATION: (255)..(263)
<223> OTHER INFORMATION: Xaa can be any naturally occurring amino acid
<220> FEATURE:
<221> NAME/KEY: misc_feature
<222> LOCATION: (266)..(267)
<223> OTHER INFORMATION: Xaa can be any naturally occurring amino acid
<220> FEATURE:
<221> NAME/KEY: misc_feature
<222> LOCATION: (271)..(271)
<223> OTHER INFORMATION: Xaa can be any naturally occurring amino acid
<220> FEATURE:
<221> NAME/KEY: misc_feature
<222> LOCATION: (273)..(275)
<223> OTHER INFORMATION: Xaa can be any naturally occurring amino acid
<220> FEATURE:
<221> NAME/KEY: misc_feature
<222> LOCATION: (279)..(283)
<223> OTHER INFORMATION: Xaa can be any naturally occurring amino acid
<220> FEATURE:
<221> NAME/KEY: misc_feature
<222> LOCATION: (287)..(288)
<223> OTHER INFORMATION: Xaa can be any naturally occurring amino acid
<220> FEATURE:
<221> NAME/KEY: misc_feature
<222> LOCATION: (290)..(291)
<223> OTHER INFORMATION: Xaa can be any naturally occurring amino acid
<220> FEATURE:
<221> NAME/KEY: misc_feature
<222> LOCATION: (297)..(298)
<223> OTHER INFORMATION: Xaa can be any naturally occurring amino acid
<220> FEATURE:
<221> NAME/KEY: misc_feature
<222> LOCATION: (305)..(308)
<223> OTHER INFORMATION: Xaa can be any naturally occurring amino acid
<220> FEATURE:
<221> NAME/KEY: misc_feature
<222> LOCATION: (310)..(310)
<223> OTHER INFORMATION: Xaa can be any naturally occurring amino acid
<220> FEATURE:
<221> NAME/KEY: misc_feature
<222> LOCATION: (312)..(313)
<223> OTHER INFORMATION: Xaa can be any naturally occurring amino acid
<220> FEATURE:
<221> NAME/KEY: misc_feature
<222> LOCATION: (316)..(320)
<223> OTHER INFORMATION: Xaa can be any naturally occurring amino acid
<220> FEATURE:
<221> NAME/KEY: misc_feature
<222> LOCATION: (322)..(326)
<223> OTHER INFORMATION: Xaa can be any naturally occurring amino acid
<220> FEATURE:
<221> NAME/KEY: misc_feature
<222> LOCATION: (328)..(332)
<223> OTHER INFORMATION: Xaa can be any naturally occurring amino acid
<220> FEATURE:
<221> NAME/KEY: misc_feature
<222> LOCATION: (336)..(336)

<223> OTHER INFORMATION: Xaa can be any naturally occurring amino acid
<220> FEATURE:
<221> NAME/KEY: misc_feature
<222> LOCATION: (338)..(338)
<223> OTHER INFORMATION: Xaa can be any naturally occurring amino acid
<220> FEATURE:
<221> NAME/KEY: misc_feature
<222> LOCATION: (340)..(340)
<223> OTHER INFORMATION: Xaa can be any naturally occurring amino acid
<220> FEATURE:
<221> NAME/KEY: misc_feature
<222> LOCATION: (343)..(343)
<223> OTHER INFORMATION: Xaa can be any naturally occurring amino acid
<220> FEATURE:
<221> NAME/KEY: misc_feature
<222> LOCATION: (348)..(349)
<223> OTHER INFORMATION: Xaa can be any naturally occurring amino acid
<220> FEATURE:
<221> NAME/KEY: misc_feature
<222> LOCATION: (351)..(354)
<223> OTHER INFORMATION: Xaa can be any naturally occurring amino acid
<220> FEATURE:
<221> NAME/KEY: misc_feature
<222> LOCATION: (356)..(356)
<223> OTHER INFORMATION: Xaa can be any naturally occurring amino acid
<220> FEATURE:
<221> NAME/KEY: misc_feature
<222> LOCATION: (360)..(360)
<223> OTHER INFORMATION: Xaa can be any naturally occurring amino acid
<220> FEATURE:
<221> NAME/KEY: misc_feature
<222> LOCATION: (362)..(364)
<223> OTHER INFORMATION: Xaa can be any naturally occurring amino acid
<220> FEATURE:
<221> NAME/KEY: misc_feature
<222> LOCATION: (366)..(366)
<223> OTHER INFORMATION: Xaa can be any naturally occurring amino acid
<220> FEATURE:
<221> NAME/KEY: misc_feature
<222> LOCATION: (370)..(370)
<223> OTHER INFORMATION: Xaa can be any naturally occurring amino acid
<220> FEATURE:
<221> NAME/KEY: misc_feature
<222> LOCATION: (372)..(372)
<223> OTHER INFORMATION: Xaa can be any naturally occurring amino acid
<220> FEATURE:
<221> NAME/KEY: misc_feature
<222> LOCATION: (375)..(375)
<223> OTHER INFORMATION: Xaa can be any naturally occurring amino acid
<220> FEATURE:
<221> NAME/KEY: misc_feature
<222> LOCATION: (380)..(380)
<223> OTHER INFORMATION: Xaa can be any naturally occurring amino acid
<220> FEATURE:
<221> NAME/KEY: misc_feature
<222> LOCATION: (382)..(382)
<223> OTHER INFORMATION: Xaa can be any naturally occurring amino acid
<220> FEATURE:
<221> NAME/KEY: misc_feature
<222> LOCATION: (384)..(384)
<223> OTHER INFORMATION: Xaa can be any naturally occurring amino acid
<220> FEATURE:
<221> NAME/KEY: misc_feature
<222> LOCATION: (388)..(389)
<223> OTHER INFORMATION: Xaa can be any naturally occurring amino acid
<220> FEATURE:
<221> NAME/KEY: misc_feature
<222> LOCATION: (391)..(392)
<223> OTHER INFORMATION: Xaa can be any naturally occurring amino acid
<220> FEATURE:
<221> NAME/KEY: misc_feature
<222> LOCATION: (395)..(396)
<223> OTHER INFORMATION: Xaa can be any naturally occurring amino acid
<220> FEATURE:
<221> NAME/KEY: misc_feature
<222> LOCATION: (400)..(402)
<223> OTHER INFORMATION: Xaa can be any naturally occurring amino acid
<220> FEATURE:
<221> NAME/KEY: misc_feature
<222> LOCATION: (405)..(406)
<223> OTHER INFORMATION: Xaa can be any naturally occurring amino acid
<220> FEATURE:
<221> NAME/KEY: misc_feature
<222> LOCATION: (410)..(415)
<223> OTHER INFORMATION: Xaa can be any naturally occurring amino acid
<220> FEATURE:
<221> NAME/KEY: misc_feature
<222> LOCATION: (421)..(423)
<223> OTHER INFORMATION: Xaa can be any naturally occurring amino acid
<220> FEATURE:
<221> NAME/KEY: misc_feature
<222> LOCATION: (425)..(429)
<223> OTHER INFORMATION: Xaa can be any naturally occurring amino acid
<220> FEATURE:
<221> NAME/KEY: misc_feature
<222> LOCATION: (431)..(434)
<223> OTHER INFORMATION: Xaa can be any naturally occurring amino acid
<220> FEATURE:
<221> NAME/KEY: misc_feature
<222> LOCATION: (436)..(436)
<223> OTHER INFORMATION: Xaa can be any naturally occurring amino acid
<220> FEATURE:
<221> NAME/KEY: misc_feature
<222> LOCATION: (439)..(439)
<223> OTHER INFORMATION: Xaa can be any naturally occurring amino acid
<220> FEATURE:
<221> NAME/KEY: misc_feature
<222> LOCATION: (441)..(441)
<223> OTHER INFORMATION: Xaa can be any naturally occurring amino acid
<220> FEATURE:
<221> NAME/KEY: misc_feature
<222> LOCATION: (443)..(443)
<223> OTHER INFORMATION: Xaa can be any naturally occurring amino acid
<220> FEATURE:
<221> NAME/KEY: misc_feature
<222> LOCATION: (449)..(451)
<223> OTHER INFORMATION: Xaa can be any naturally occurring amino acid
<220> FEATURE:
<221> NAME/KEY: misc_feature
<222> LOCATION: (456)..(456)
<223> OTHER INFORMATION: Xaa can be any naturally occurring amino acid
<220> FEATURE:
<221> NAME/KEY: misc_feature
<222> LOCATION: (460)..(460)
<223> OTHER INFORMATION: Xaa can be any naturally occurring amino acid
<220> FEATURE:
<221> NAME/KEY: misc_feature
<222> LOCATION: (462)..(470)
<223> OTHER INFORMATION: Xaa can be any naturally occurring amino acid

<400> SEQUENCE: 19

```
Met Ala Arg Leu Arg Xaa Arg Arg Pro Arg Gly Arg Phe Xaa Xaa Xaa
1               5                   10                  15

Xaa Arg Gly Arg Trp His Xaa Xaa Xaa Arg Leu Arg Arg Arg Xaa Tyr
            20                  25                  30

Ser Arg Arg Gly Lys Phe Arg Xaa Xaa Arg Arg Xaa Xaa Xaa Xaa Arg
        35                  40                  45

Arg Xaa Xaa Arg Xaa Xaa Phe His Asn Pro Xaa Pro Gly Xaa Tyr Xaa
    50                  55                  60

Val Arg Leu Pro Asn Pro Xaa Xaa Xaa Xaa Thr Xaa Xaa Phe Gln Gly
65                  70                  75                  80

Ile Xaa Phe Xaa Xaa Glu Xaa Xaa Xaa Xaa Xaa Lys Xaa Xaa Xaa Xaa
                85                  90                  95

Gly Gly Tyr Xaa Xaa Xaa Leu Xaa Xaa Xaa Xaa Val Ala Xaa Ile Xaa
            100                 105                 110

Val Asn Leu Xaa Glu Phe Xaa Leu Ala Xaa Met Xaa Leu Xaa Xaa Xaa
        115                 120                 125

Ser Lys Ile Gly Gly Pro Xaa Xaa Xaa Xaa Xaa Xaa Xaa Xaa Gly Xaa
    130                 135                 140
```

```
Gln Trp Ser Xaa Gln Xaa Xaa Gln Xaa Ala Trp Pro Xaa Xaa Xaa Xaa
145                 150                 155                 160

Xaa Xaa Xaa Xaa Xaa Xaa Pro Ser Xaa Xaa Pro Ser Xaa Trp Trp Arg
                165                 170                 175

Trp Ala Leu Xaa Xaa Met Xaa Pro Xaa Xaa Xaa Xaa Arg Phe Xaa Asn
            180                 185                 190

Xaa Pro Lys Xaa Met Thr Leu Xaa Xaa Met Gly Xaa Xaa Xaa Gly Gly
        195                 200                 205

Trp Xaa Leu Phe Arg His Xaa Xaa Thr Xaa Phe Xaa Xaa Leu Ala Thr
    210                 215                 220

Xaa Xaa Xaa Gly Xaa Phe Ser Pro Val Ala Ser Leu Leu Xaa Gln Xaa
225                 230                 235                 240

Xaa Tyr Xaa Xaa Arg Arg Xaa Leu Glu Gly Phe Xaa Val Lys Xaa Xaa
                245                 250                 255

Xaa Xaa Xaa Xaa Xaa Xaa Xaa Arg Lys Xaa Xaa Gln Pro Met Xaa Gly
            260                 265                 270

Xaa Xaa Xaa Tyr Ala Thr Xaa Xaa Xaa Xaa Xaa Asp Glu Gln Xaa Xaa
        275                 280                 285

Pro Xaa Xaa Pro Pro Asp Pro Pro Xaa Xaa Pro Asn Gln Gly Gly Cys
    290                 295                 300

Xaa Xaa Xaa Xaa Ala Xaa Gly Xaa Xaa Arg Leu Xaa Xaa Xaa Xaa Xaa
305                 310                 315                 320

Ser Xaa Xaa Xaa Xaa Xaa Ser Xaa Xaa Xaa Xaa Xaa Ser Phe Ala Xaa
                325                 330                 335

Leu Xaa Ala Xaa Gly Ala Xaa Trp Ser Phe Pro Xaa Xaa Gln Xaa Xaa
            340                 345                 350

Xaa Xaa Arg Xaa Ser Phe Asn Xaa His Xaa Xaa Xaa Gly Xaa Gly Asp
        355                 360                 365

Pro Xaa Gly Xaa Arg Trp Xaa Thr Leu Val Pro Xaa Gly Xaa Glu Xaa
    370                 375                 380

Ile Thr Asp Xaa Xaa Met Xaa Xaa Pro Ala Xaa Xaa Leu Asp Thr Xaa
385                 390                 395                 400

Xaa Xaa Thr Leu Xaa Xaa Ala Gln Gly Xaa Xaa Xaa Xaa Xaa Xaa Tyr
                405                 410                 415

Lys Phe Gly Thr Xaa Xaa Xaa Ala Xaa Xaa Xaa Xaa Xaa Met Xaa Xaa
            420                 425                 430

Xaa Xaa Trp Xaa Val Val Xaa Val Xaa Ser Xaa Trp Gln Leu Gly Asn
        435                 440                 445

Xaa Xaa Xaa Pro Tyr Pro Trp Xaa Val Asn Trp Xaa Asn Xaa Xaa Xaa
    450                 455                 460

Xaa Xaa Xaa Xaa Xaa Xaa
465                 470
```

<210> SEQ ID NO 20
<211> LENGTH: 238
<212> TYPE: PRT
<213> ORGANISM: artificial
<220> FEATURE:
<223> OTHER INFORMATION: consensus between CAV P69485 and HGyV VP2
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: misc_feature
<222> LOCATION: (22)..(23)
<223> OTHER INFORMATION: Xaa can be any naturally occurring amino acid
<220> FEATURE:
<221> NAME/KEY: misc_feature
<222> LOCATION: (25)..(26)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (36)..(37)
<223> OTHER INFORMATION: Xaa can be any naturally occurring amino acid
<220> FEATURE:
<221> NAME/KEY: misc_feature
<222> LOCATION: (40)..(46)
<223> OTHER INFORMATION: Xaa can be any naturally occurring amino acid
<220> FEATURE:
<221> NAME/KEY: misc_feature
<222> LOCATION: (53)..(54)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (63)..(64)
<223> OTHER INFORMATION: Xaa can be any naturally occurring amino acid
<220> FEATURE:
<221> NAME/KEY: misc_feature
<222> LOCATION: (66)..(66)
<223> OTHER INFORMATION: Xaa can be any naturally occurring amino acid
<220> FEATURE:
<221> NAME/KEY: misc_feature
<222> LOCATION: (70)..(76)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (86)..(86)
<223> OTHER INFORMATION: Xaa can be any naturally occurring amino acid
<220> FEATURE:
<221> NAME/KEY: misc_feature
<222> LOCATION: (90)..(90)
<223> OTHER INFORMATION: Xaa can be any naturally occurring amino acid
<220> FEATURE:
<221> NAME/KEY: misc_feature
<222> LOCATION: (98)..(98)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid
<220> FEATURE:
<221> NAME/KEY: misc_feature
<222> LOCATION: (104)..(105)
<223> OTHER INFORMATION: Xaa can be any naturally occurring amino acid
<220> FEATURE:
<221> NAME/KEY: misc_feature
<222> LOCATION: (108)..(108)
<223> OTHER INFORMATION: Xaa can be any naturally occurring amino acid
<220> FEATURE:
<221> NAME/KEY: misc_feature
<222> LOCATION: (111)..(112)
<223> OTHER INFORMATION: Xaa can be any naturally occurring amino acid
<220> FEATURE:
<221> NAME/KEY: misc_feature
<222> LOCATION: (120)..(121)

<223> OTHER INFORMATION: Xaa can be any naturally occurring amino acid
<220> FEATURE:
<221> NAME/KEY: misc_feature
<222> LOCATION: (124)..(127)
<223> OTHER INFORMATION: Xaa can be any naturally occurring amino acid
<220> FEATURE:
<221> NAME/KEY: misc_feature
<222> LOCATION: (130)..(136)
<223> OTHER INFORMATION: Xaa can be any naturally occurring amino acid
<220> FEATURE:
<221> NAME/KEY: misc_feature
<222> LOCATION: (139)..(139)
<223> OTHER INFORMATION: Xaa can be any naturally occurring amino acid
<220> FEATURE:
<221> NAME/KEY: misc_feature
<222> LOCATION: (142)..(143)
<223> OTHER INFORMATION: Xaa can be any naturally occurring amino acid
<220> FEATURE:
<221> NAME/KEY: misc_feature
<222> LOCATION: (145)..(146)
<223> OTHER INFORMATION: Xaa can be any naturally occurring amino acid
<220> FEATURE:
<221> NAME/KEY: misc_feature
<222> LOCATION: (154)..(158)
<223> OTHER INFORMATION: Xaa can be any naturally occurring amino acid
<220> FEATURE:
<221> NAME/KEY: misc_feature
<222> LOCATION: (161)..(162)
<223> OTHER INFORMATION: Xaa can be any naturally occurring amino acid
<220> FEATURE:
<221> NAME/KEY: misc_feature
<222> LOCATION: (164)..(164)
<223> OTHER INFORMATION: Xaa can be any naturally occurring amino acid
<220> FEATURE:
<221> NAME/KEY: misc_feature
<222> LOCATION: (170)..(170)
<223> OTHER INFORMATION: Xaa can be any naturally occurring amino acid
<220> FEATURE:
<221> NAME/KEY: misc_feature
<222> LOCATION: (178)..(178)
<223> OTHER INFORMATION: Xaa can be any naturally occurring amino acid
<220> FEATURE:
<221> NAME/KEY: misc_feature
<222> LOCATION: (182)..(183)
<223> OTHER INFORMATION: Xaa can be any naturally occurring amino acid
<220> FEATURE:
<221> NAME/KEY: misc_feature
<222> LOCATION: (185)..(186)
<223> OTHER INFORMATION: Xaa can be any naturally occurring amino acid
<220> FEATURE:
<221> NAME/KEY: misc_feature
<222> LOCATION: (193)..(193)
<223> OTHER INFORMATION: Xaa can be any naturally occurring amino acid
<220> FEATURE:
<221> NAME/KEY: misc_feature
<222> LOCATION: (196)..(198)
<223> OTHER INFORMATION: Xaa can be any naturally occurring amino acid
<220> FEATURE:
<221> NAME/KEY: misc_feature
<222> LOCATION: (200)..(200)
<223> OTHER INFORMATION: Xaa can be any naturally occurring amino acid
<220> FEATURE:
<221> NAME/KEY: misc_feature
<222> LOCATION: (209)..(209)
<223> OTHER INFORMATION: Xaa can be any naturally occurring amino acid
<220> FEATURE:
<221> NAME/KEY: misc_feature
<222> LOCATION: (213)..(222)
<223> OTHER INFORMATION: Xaa can be any naturally occurring amino acid
<220> FEATURE:
<221> NAME/KEY: misc_feature
<222> LOCATION: (224)..(224)
<223> OTHER INFORMATION: Xaa can be any naturally occurring amino acid
<220> FEATURE:
<221> NAME/KEY: misc_feature
<222> LOCATION: (226)..(228)
<223> OTHER INFORMATION: Xaa can be any naturally occurring amino acid
<220> FEATURE:
<221> NAME/KEY: misc_feature
<222> LOCATION: (232)..(232)
<223> OTHER INFORMATION: Xaa can be any naturally occurring amino acid
<220> FEATURE:
<221> NAME/KEY: misc_feature
<222> LOCATION: (235)..(236)
<223> OTHER INFORMATION: Xaa can be any naturally occurring amino acid

<400> SEQUENCE: 20

```
Met Xaa Xaa Gly Gly Leu Gly Asp Cys Ser Ala Cys Glu Xaa Xaa Ala
1               5                   10                  15

Ala Gly Gly Ser Glu Xaa Xaa Leu Xaa Xaa Glu Gly Gln Xaa Gly Pro
            20                  25                  30

Ser Gly Ala Xaa Xaa Thr Gly Xaa Xaa Xaa Xaa Xaa Xaa Xaa Pro Leu
        35                  40                  45

Ser Pro Thr Ser Xaa Xaa Tyr Ser Xaa Arg Thr Ile Asn Gly Xaa Xaa
    50                  55                  60

Ala Xaa Asn Lys Phe Xaa Xaa Xaa Xaa Xaa Xaa Xaa Leu Xaa Arg Asp
65                  70                  75                  80

Pro Xaa Trp Tyr Arg Xaa Asn Tyr Asn Xaa Ser Ile Ala Thr Trp Leu
                85                  90                  95

Arg Xaa Cys Xaa Arg Ser His Xaa Xaa Ile Cys Xaa Cys Gly Xaa Xaa
            100                 105                 110

Arg Ser His Trp Phe Gln Glu Xaa Xaa Gly Leu Xaa Xaa Xaa Xaa Thr
        115                 120                 125

Gln Xaa Xaa Xaa Xaa Xaa Xaa Xaa Leu Arg Xaa Leu Arg Xaa Xaa Gly
    130                 135                 140

Xaa Xaa Ala Lys Arg Lys Leu Asp Tyr Xaa Xaa Xaa Xaa Xaa Thr Pro
145                 150                 155                 160

Xaa Xaa Lys Xaa Val Tyr Lys Thr Val Xaa Trp Gln Asp Tyr Glu Glu
                165                 170                 175

Asp Xaa Leu Ala Asp Xaa Xaa Ala Xaa Xaa Thr Pro Ser Glu Glu Asp
            180                 185                 190

Xaa Gly Thr Xaa Xaa Xaa Asp Xaa Asp Glu Asp Ala Ile Pro Gly Gly
        195                 200                 205

Xaa Asn Phe Asp Xaa Xaa Xaa Xaa Xaa Xaa Xaa Xaa Xaa Xaa Leu Xaa
    210                 215                 220

Gly Xaa Xaa Xaa Thr His Thr Xaa Ala Pro Xaa Xaa Ile Val
225                 230                 235
```

<210> SEQ ID NO 21
<211> LENGTH: 21
<212> TYPE: DNA
<213> ORGANISM: artificial
<220> FEATURE:
<223> OTHER INFORMATION: Primer

<400> SEQUENCE: 21
tccgttgcag tgtgctcgtt g 21

<210> SEQ ID NO 22
<211> LENGTH: 20
<212> TYPE: DNA
<213> ORGANISM: artificial
<220> FEATURE:
<223> OTHER INFORMATION: Primer

<400> SEQUENCE: 22
gcacttagag ggcttcccag 20

```
<210> SEQ ID NO 23
<211> LENGTH: 20
<212> TYPE: DNA
<213> ORGANISM: artificial
<220> FEATURE:
<223> OTHER INFORMATION: Primer

<400> SEQUENCE: 23

ctcatctgcc ggtgcattgg                                                 20


<210> SEQ ID NO 24
<211> LENGTH: 20
<212> TYPE: DNA
<213> ORGANISM: artificial
<220> FEATURE:
<223> OTHER INFORMATION: Primer

<400> SEQUENCE: 24

ccgggctcct atgtggtaag                                                 20


<210> SEQ ID NO 25
<211> LENGTH: 21
<212> TYPE: DNA
<213> ORGANISM: artificial
<220> FEATURE:
<223> OTHER INFORMATION: Primer

<400> SEQUENCE: 25

aaagcttgag cctccggaat g                                               21


<210> SEQ ID NO 26
<211> LENGTH: 21
<212> TYPE: DNA
<213> ORGANISM: artificial
<220> FEATURE:
<223> OTHER INFORMATION: Primer

<400> SEQUENCE: 26

taggcaagag gggcaacttg g                                               21


<210> SEQ ID NO 27
<211> LENGTH: 21
<212> TYPE: DNA
<213> ORGANISM: artificial
<220> FEATURE:
<223> OTHER INFORMATION: Primer

<400> SEQUENCE: 27

tagttgttgc tcgtcggcga g                                               21


<210> SEQ ID NO 28
<211> LENGTH: 20
<212> TYPE: DNA
<213> ORGANISM: artificial
<220> FEATURE:
<223> OTHER INFORMATION: Primer

<400> SEQUENCE: 28

ctttcaccac gcaccaaggg                                                 20


<210> SEQ ID NO 29
<211> LENGTH: 6
<212> TYPE: DNA
<213> ORGANISM: artificial
<220> FEATURE:
<223> OTHER INFORMATION: Direct repeats of sequence found in the CAV
      promoter
```

<400> SEQUENCE: 29 agctca 6

<210> SEQ ID NO 30
<211> LENGTH: 6
<212> TYPE: DNA
<213> ORGANISM: artificial
<220> FEATURE:
<223> OTHER INFORMATION: repeated cis-elements

<400> SEQUENCE: 30 aggtca 6

<210> SEQ ID NO 31
<211> LENGTH: 6
<212> TYPE: DNA
<213> ORGANISM: artificial
<220> FEATURE:
<223> OTHER INFORMATION: repeated cis-elements

<400> SEQUENCE: 31 acgtca 6

<210> SEQ ID NO 32
<211> LENGTH: 6
<212> TYPE: DNA
<213> ORGANISM: artificial
<220> FEATURE:
<223> OTHER INFORMATION: repeated cis-elements

<400> SEQUENCE: 32 acgtca 6

<210> SEQ ID NO 33
<211> LENGTH: 12
<212> TYPE: DNA
<213> ORGANISM: artificial
<220> FEATURE:
<223> OTHER INFORMATION: palindromic sequence

<400> SEQUENCE: 33
caatcagaat tg 12

<210> SEQ ID NO 34
<211> LENGTH: 1398
<212> TYPE: DNA
<213> ORGANISM: Artificial
<220> FEATURE:
<223> OTHER INFORMATION: H-VP1

<400> SEQUENCE: 34
atggcaagac tacgaagaag acgacctcgc ggacgctttg gcttctacca cagaggacga 60
tggcactgga gacacagact gcgacgaaga cgctattccc ggaggggtaa atttcgatat 120
gcgcgtagaa gatcctttga tcgccgcgtt aagaggagga tcttcaaccc acacccgggc 180
tcctatgtgg taaggctacc gaacccttac aataagctta ccctcttttt ccaaggcatt 240
gtattcattc cggaggctca agcttttgtt aaaagcacct ataaaaagac taaccttacg 300
gtttgccatg tagcctccat aaatgttaac ctccgagaat ttatgcttgc aacaatgcct 360
ttagatgcaa agagcaaaat cggaggccct aacccttatc ctcagcactt gcaggggtgc 420
caatggtcag cacaaacgac gcaggacgca tggccgtacg cagcgggcat gtcagaaaca 480

-continued

```
aaaagaccca gcgtaccacc gagtgagtgg tggcgctggg ctctcctggt gatgcaccct    540

agagcacctg gcagatttta caatgcccca aagctaatga ctctggacgc tatgggagac    600

ctgttagggg gctggcagct attcaggcat gtaaaaacca agttcagagt gctagcgact    660

atgggacaag ggcctttctc accagttgca agcctacttg tacaaaatga ctactggagc    720

aggaggcact tagagggctt cccagttaaa ggtgcaccac ctatgtgcac catgcaaaga    780

aaaactcagc agtacggcaa cgtggagtcc aatgcaccgg cagatgagca atggctaccc    840

gtaaatcccc cagacccacc agtgtaccca aaccagggag gatgctccca aaacgtggct    900

ccaggcatat accggcttgc aggcttagaa gacagcagca gatgctttta ttcaaaggct    960

tgtttcccca gctttgcagc gctttctgct atgggtgcac cctggtcatt tcctagcact   1020

caaaaaccta ttcaaagagg ctcatttaac aagcactcca tcacggggac aggggacccc   1080

cagggccgac ggtggttaac acttgtgcct aaaggagtcg agtggattac tgacgacacc   1140

atggaaccta cgcaactgga cacagacatt gcaacactct tcttggctca aggcagtcca   1200

gtatgggcac cctacaaatt cggaactttt cacaaagcga tggcgctaac agcgatgcag   1260

accacccctt ggtgcgtggt gaaagtccgt tccatctggc agctcggcaa ccaaagacag   1320

ccgtacccat ggcaagtgaa ctggtacaac gagcacactg caacggacag atacaacccg   1380

ccccccgtca ataaataa                                                  1398
```

```
<210> SEQ ID NO 35
<211> LENGTH: 465
<212> TYPE: PRT
<213> ORGANISM: Artificial
<220> FEATURE:
<223> OTHER INFORMATION: H-VP1

<400> SEQUENCE: 35

Met Ala Arg Leu Arg Arg Arg Arg Pro Arg Gly Arg Phe Gly Phe Tyr
1               5                   10                  15

His Arg Gly Arg Trp His Trp Arg His Arg Leu Arg Arg Arg Arg Tyr
            20                  25                  30

Ser Arg Arg Gly Lys Phe Arg Tyr Ala Arg Arg Arg Ser Phe Asp Arg
        35                  40                  45

Arg Val Lys Arg Arg Ile Phe Asn Pro His Pro Gly Ser Tyr Val Val
    50                  55                  60

Arg Leu Pro Asn Pro Tyr Asn Lys Leu Thr Leu Phe Phe Gln Gly Ile
65                  70                  75                  80

Val Phe Ile Pro Glu Ala Gln Ala Phe Val Lys Ser Thr Tyr Lys Lys
                85                  90                  95

Thr Asn Leu Thr Val Cys His Val Ala Ser Ile Asn Val Asn Leu Arg
            100                 105                 110

Glu Phe Met Leu Ala Thr Met Pro Leu Asp Ala Lys Ser Lys Ile Gly
        115                 120                 125

Gly Pro Asn Pro Tyr Pro Gln His Leu Gln Gly Cys Gln Trp Ser Ala
    130                 135                 140

Gln Thr Thr Gln Asp Ala Trp Pro Tyr Ala Ala Gly Met Ser Glu Thr
145                 150                 155                 160

Lys Arg Pro Ser Val Pro Pro Ser Glu Trp Trp Arg Trp Ala Leu Leu
                165                 170                 175

Val Met His Pro Arg Ala Pro Gly Arg Phe Tyr Asn Ala Pro Lys Leu
            180                 185                 190

Met Thr Leu Asp Ala Met Gly Asp Leu Leu Gly Gly Trp Gln Leu Phe
```

```
        195                 200                 205

Arg His Val Lys Thr Lys Phe Arg Val Leu Ala Thr Met Gly Gln Gly
    210                 215                 220

Ala Phe Ser Pro Val Ala Ser Leu Leu Val Gln Asn Asp Tyr Trp Ser
225                 230                 235                 240

Arg Arg His Leu Glu Gly Phe Pro Val Lys Gly Ala Pro Pro Met Cys
                245                 250                 255

Thr Met Gln Arg Lys Thr Gln Gln Tyr Gly Asn Val Glu Ser Asn Ala
            260                 265                 270

Pro Ala Asp Glu Gln Trp Leu Pro Val Asn Pro Pro Asp Pro Pro Val
        275                 280                 285

Tyr Pro Asn Gln Gly Gly Cys Ser Gln Asn Val Ala Pro Gly Ile Tyr
    290                 295                 300

Arg Leu Ala Gly Leu Glu Asp Ser Ser Arg Cys Phe Tyr Ser Lys Ala
305                 310                 315                 320

Cys Phe Pro Ser Phe Ala Ala Leu Ser Ala Met Gly Ala Pro Trp Ser
                325                 330                 335

Phe Pro Ser Thr Gln Lys Pro Ile Gln Arg Gly Ser Phe Asn Lys His
            340                 345                 350

Ser Ile Thr Gly Thr Gly Asp Pro Gln Gly Arg Arg Trp Leu Thr Leu
        355                 360                 365

Val Pro Lys Gly Val Glu Trp Ile Thr Asp Asp Thr Met Glu Pro Thr
    370                 375                 380

Gln Leu Asp Thr Asp Ile Ala Thr Leu Phe Leu Ala Gln Gly Ser Pro
385                 390                 395                 400

Val Trp Ala Pro Tyr Lys Phe Gly Thr Phe His Lys Ala Met Ala Leu
                405                 410                 415

Thr Ala Met Gln Thr Thr Pro Trp Cys Val Val Lys Val Arg Ser Ile
            420                 425                 430

Trp Gln Leu Gly Asn Gln Arg Gln Pro Tyr Pro Trp Gln Val Asn Trp
        435                 440                 445

Tyr Asn Glu His Thr Ala Thr Asp Arg Tyr Asn Pro Pro Pro Val Asn
    450                 455                 460

Lys
465
```

<210> SEQ ID NO 36
<211> LENGTH: 476
<212> TYPE: PRT
<213> ORGANISM: artificial
<220> FEATURE:
<223> OTHER INFORMATION: consensus between CAV P54088 and HGyV VP1
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (14)..(17)
<223> OTHER INFORMATION: Xaa can be any naturally occurring amino acid
<220> FEATURE:
<221> NAME/KEY: misc_feature
<222> LOCATION: (23)..(25)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (40)..(41)

<223> OTHER INFORMATION: Xaa can be any naturally occurring amino acid
<220> FEATURE:
<221> NAME/KEY: misc_feature
<222> LOCATION: (44)..(47)
<223> OTHER INFORMATION: Xaa can be any naturally occurring amino acid
<220> FEATURE:
<221> NAME/KEY: misc_feature
<222> LOCATION: (50)..(51)
<223> OTHER INFORMATION: Xaa can be any naturally occurring amino acid
<220> FEATURE:
<221> NAME/KEY: misc_feature
<222> LOCATION: (53)..(54)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (62)..(62)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (71)..(74)
<223> OTHER INFORMATION: Xaa can be any naturally occurring amino acid
<220> FEATURE:
<221> NAME/KEY: misc_feature
<222> LOCATION: (76)..(77)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (84)..(85)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid
<220> FEATURE:
<221> NAME/KEY: misc_feature
<222> LOCATION: (93)..(96)
<223> OTHER INFORMATION: Xaa can be any naturally occurring amino acid
<220> FEATURE:
<221> NAME/KEY: misc_feature
<222> LOCATION: (100)..(102)
<223> OTHER INFORMATION: Xaa can be any naturally occurring amino acid
<220> FEATURE:
<221> NAME/KEY: misc_feature
<222> LOCATION: (104)..(107)
<223> OTHER INFORMATION: Xaa can be any naturally occurring amino acid
<220> FEATURE:
<221> NAME/KEY: misc_feature
<222> LOCATION: (110)..(110)
<223> OTHER INFORMATION: Xaa can be any naturally occurring amino acid
<220> FEATURE:
<221> NAME/KEY: misc_feature
<222> LOCATION: (112)..(112)
<223> OTHER INFORMATION: Xaa can be any naturally occurring amino acid
<220> FEATURE:
<221> NAME/KEY: misc_feature
<222> LOCATION: (116)..(116)
<223> OTHER INFORMATION: Xaa can be any naturally occurring amino acid
<220> FEATURE:
<221> NAME/KEY: misc_feature
<222> LOCATION: (119)..(119)
<223> OTHER INFORMATION: Xaa can be any naturally occurring amino acid
<220> FEATURE:
<221> NAME/KEY: misc_feature
<222> LOCATION: (122)..(122)
<223> OTHER INFORMATION: Xaa can be any naturally occurring amino acid
<220> FEATURE:
<221> NAME/KEY: misc_feature
<222> LOCATION: (124)..(124)
<223> OTHER INFORMATION: Xaa can be any naturally occurring amino acid
<220> FEATURE:
<221> NAME/KEY: misc_feature
<222> LOCATION: (126)..(128)
<223> OTHER INFORMATION: Xaa can be any naturally occurring amino acid
<220> FEATURE:
<221> NAME/KEY: misc_feature
<222> LOCATION: (135)..(142)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (148)..(148)
<223> OTHER INFORMATION: Xaa can be any naturally occurring amino acid
<220> FEATURE:
<221> NAME/KEY: misc_feature
<222> LOCATION: (150)..(151)
<223> OTHER INFORMATION: Xaa can be any naturally occurring amino acid
<220> FEATURE:
<221> NAME/KEY: misc_feature
<222> LOCATION: (153)..(153)
<223> OTHER INFORMATION: Xaa can be any naturally occurring amino acid
<220> FEATURE:
<221> NAME/KEY: misc_feature
<222> LOCATION: (157)..(166)
<223> OTHER INFORMATION: Xaa can be any naturally occurring amino acid
<220> FEATURE:
<221> NAME/KEY: misc_feature
<222> LOCATION: (169)..(170)
<223> OTHER INFORMATION: Xaa can be any naturally occurring amino acid
<220> FEATURE:
<221> NAME/KEY: misc_feature
<222> LOCATION: (173)..(173)
<223> OTHER INFORMATION: Xaa can be any naturally occurring amino acid
<220> FEATURE:
<221> NAME/KEY: misc_feature
<222> LOCATION: (180)..(181)
<223> OTHER INFORMATION: Xaa can be any naturally occurring amino acid
<220> FEATURE:
<221> NAME/KEY: misc_feature
<222> LOCATION: (183)..(183)
<223> OTHER INFORMATION: Xaa can be any naturally occurring amino acid
<220> FEATURE:
<221> NAME/KEY: misc_feature
<222> LOCATION: (185)..(188)
<223> OTHER INFORMATION: Xaa can be any naturally occurring amino acid
<220> FEATURE:
<221> NAME/KEY: misc_feature
<222> LOCATION: (191)..(191)
<223> OTHER INFORMATION: Xaa can be any naturally occurring amino acid
<220> FEATURE:
<221> NAME/KEY: misc_feature
<222> LOCATION: (193)..(193)
<223> OTHER INFORMATION: Xaa can be any naturally occurring amino acid
<220> FEATURE:
<221> NAME/KEY: misc_feature
<222> LOCATION: (196)..(196)
<223> OTHER INFORMATION: Xaa can be any naturally occurring amino acid
<220> FEATURE:
<221> NAME/KEY: misc_feature
<222> LOCATION: (200)..(201)
<223> OTHER INFORMATION: Xaa can be any naturally occurring amino acid
<220> FEATURE:
<221> NAME/KEY: misc_feature
<222> LOCATION: (204)..(206)
<223> OTHER INFORMATION: Xaa can be any naturally occurring amino acid
<220> FEATURE:
<221> NAME/KEY: misc_feature
<222> LOCATION: (210)..(210)
<223> OTHER INFORMATION: Xaa can be any naturally occurring amino acid
<220> FEATURE:
<221> NAME/KEY: misc_feature
<222> LOCATION: (215)..(216)
<223> OTHER INFORMATION: Xaa can be any naturally occurring amino acid
<220> FEATURE:

```
<221> NAME/KEY: misc_feature
<222> LOCATION: (218)..(218)
<223> OTHER INFORMATION: Xaa can be any naturally occurring amino acid
<220> FEATURE:
<221> NAME/KEY: misc_feature
<222> LOCATION: (220)..(221)
<223> OTHER INFORMATION: Xaa can be any naturally occurring amino acid
<220> FEATURE:
<221> NAME/KEY: misc_feature
<222> LOCATION: (225)..(227)
<223> OTHER INFORMATION: Xaa can be any naturally occurring amino acid
<220> FEATURE:
<221> NAME/KEY: misc_feature
<222> LOCATION: (229)..(229)
<223> OTHER INFORMATION: Xaa can be any naturally occurring amino acid
<220> FEATURE:
<221> NAME/KEY: misc_feature
<222> LOCATION: (238)..(238)
<223> OTHER INFORMATION: Xaa can be any naturally occurring amino acid
<220> FEATURE:
<221> NAME/KEY: misc_feature
<222> LOCATION: (240)..(241)
<223> OTHER INFORMATION: Xaa can be any naturally occurring amino acid
<220> FEATURE:
<221> NAME/KEY: misc_feature
<222> LOCATION: (243)..(244)
<223> OTHER INFORMATION: Xaa can be any naturally occurring amino acid
<220> FEATURE:
<221> NAME/KEY: misc_feature
<222> LOCATION: (247)..(247)
<223> OTHER INFORMATION: Xaa can be any naturally occurring amino acid
<220> FEATURE:
<221> NAME/KEY: misc_feature
<222> LOCATION: (252)..(252)
<223> OTHER INFORMATION: Xaa can be any naturally occurring amino acid
<220> FEATURE:
<221> NAME/KEY: misc_feature
<222> LOCATION: (255)..(263)
<223> OTHER INFORMATION: Xaa can be any naturally occurring amino acid
<220> FEATURE:
<221> NAME/KEY: misc_feature
<222> LOCATION: (266)..(267)
<223> OTHER INFORMATION: Xaa can be any naturally occurring amino acid
<220> FEATURE:
<221> NAME/KEY: misc_feature
<222> LOCATION: (271)..(271)
<223> OTHER INFORMATION: Xaa can be any naturally occurring amino acid
<220> FEATURE:
<221> NAME/KEY: misc_feature
<222> LOCATION: (273)..(275)
<223> OTHER INFORMATION: Xaa can be any naturally occurring amino acid
<220> FEATURE:
<221> NAME/KEY: misc_feature
<222> LOCATION: (279)..(283)
<223> OTHER INFORMATION: Xaa can be any naturally occurring amino acid
<220> FEATURE:
<221> NAME/KEY: misc_feature
<222> LOCATION: (287)..(288)
<223> OTHER INFORMATION: Xaa can be any naturally occurring amino acid
<220> FEATURE:
<221> NAME/KEY: misc_feature
<222> LOCATION: (290)..(291)
<223> OTHER INFORMATION: Xaa can be any naturally occurring amino acid
<220> FEATURE:
<221> NAME/KEY: misc_feature
<222> LOCATION: (297)..(298)
<223> OTHER INFORMATION: Xaa can be any naturally occurring amino acid
<220> FEATURE:
<221> NAME/KEY: misc_feature
<222> LOCATION: (305)..(308)
<223> OTHER INFORMATION: Xaa can be any naturally occurring amino acid
<220> FEATURE:
<221> NAME/KEY: misc_feature
<222> LOCATION: (310)..(310)
<223> OTHER INFORMATION: Xaa can be any naturally occurring amino acid
<220> FEATURE:
<221> NAME/KEY: misc_feature
<222> LOCATION: (312)..(313)
<223> OTHER INFORMATION: Xaa can be any naturally occurring amino acid
```

<220> FEATURE:
<221> NAME/KEY: misc_feature
<222> LOCATION: (316)..(320)
<223> OTHER INFORMATION: Xaa can be any naturally occurring amino acid
<220> FEATURE:
<221> NAME/KEY: misc_feature
<222> LOCATION: (322)..(326)
<223> OTHER INFORMATION: Xaa can be any naturally occurring amino acid
<220> FEATURE:
<221> NAME/KEY: misc_feature
<222> LOCATION: (328)..(332)
<223> OTHER INFORMATION: Xaa can be any naturally occurring amino acid
<220> FEATURE:
<221> NAME/KEY: misc_feature
<222> LOCATION: (336)..(336)
<223> OTHER INFORMATION: Xaa can be any naturally occurring amino acid
<220> FEATURE:
<221> NAME/KEY: misc_feature
<222> LOCATION: (338)..(338)
<223> OTHER INFORMATION: Xaa can be any naturally occurring amino acid
<220> FEATURE:
<221> NAME/KEY: misc_feature
<222> LOCATION: (340)..(340)
<223> OTHER INFORMATION: Xaa can be any naturally occurring amino acid
<220> FEATURE:
<221> NAME/KEY: misc_feature
<222> LOCATION: (343)..(343)
<223> OTHER INFORMATION: Xaa can be any naturally occurring amino acid
<220> FEATURE:
<221> NAME/KEY: misc_feature
<222> LOCATION: (348)..(349)
<223> OTHER INFORMATION: Xaa can be any naturally occurring amino acid
<220> FEATURE:
<221> NAME/KEY: misc_feature
<222> LOCATION: (351)..(354)
<223> OTHER INFORMATION: Xaa can be any naturally occurring amino acid
<220> FEATURE:
<221> NAME/KEY: misc_feature
<222> LOCATION: (356)..(356)
<223> OTHER INFORMATION: Xaa can be any naturally occurring amino acid
<220> FEATURE:
<221> NAME/KEY: misc_feature
<222> LOCATION: (360)..(360)
<223> OTHER INFORMATION: Xaa can be any naturally occurring amino acid
<220> FEATURE:
<221> NAME/KEY: misc_feature
<222> LOCATION: (362)..(364)
<223> OTHER INFORMATION: Xaa can be any naturally occurring amino acid
<220> FEATURE:
<221> NAME/KEY: misc_feature
<222> LOCATION: (366)..(366)
<223> OTHER INFORMATION: Xaa can be any naturally occurring amino acid
<220> FEATURE:
<221> NAME/KEY: misc_feature
<222> LOCATION: (370)..(370)
<223> OTHER INFORMATION: Xaa can be any naturally occurring amino acid
<220> FEATURE:
<221> NAME/KEY: misc_feature
<222> LOCATION: (372)..(372)
<223> OTHER INFORMATION: Xaa can be any naturally occurring amino acid
<220> FEATURE:
<221> NAME/KEY: misc_feature
<222> LOCATION: (375)..(375)
<223> OTHER INFORMATION: Xaa can be any naturally occurring amino acid
<220> FEATURE:
<221> NAME/KEY: misc_feature
<222> LOCATION: (380)..(380)
<223> OTHER INFORMATION: Xaa can be any naturally occurring amino acid
<220> FEATURE:
<221> NAME/KEY: misc_feature
<222> LOCATION: (382)..(382)
<223> OTHER INFORMATION: Xaa can be any naturally occurring amino acid
<220> FEATURE:
<221> NAME/KEY: misc_feature
<222> LOCATION: (384)..(384)
<223> OTHER INFORMATION: Xaa can be any naturally occurring amino acid
<220> FEATURE:
<221> NAME/KEY: misc_feature
<222> LOCATION: (388)..(389)

<223> OTHER INFORMATION: Xaa can be any naturally occurring amino acid
<220> FEATURE:
<221> NAME/KEY: misc_feature
<222> LOCATION: (391)..(392)
<223> OTHER INFORMATION: Xaa can be any naturally occurring amino acid
<220> FEATURE:
<221> NAME/KEY: misc_feature
<222> LOCATION: (395)..(396)
<223> OTHER INFORMATION: Xaa can be any naturally occurring amino acid
<220> FEATURE:
<221> NAME/KEY: misc_feature
<222> LOCATION: (400)..(402)
<223> OTHER INFORMATION: Xaa can be any naturally occurring amino acid
<220> FEATURE:
<221> NAME/KEY: misc_feature
<222> LOCATION: (405)..(406)
<223> OTHER INFORMATION: Xaa can be any naturally occurring amino acid
<220> FEATURE:
<221> NAME/KEY: misc_feature
<222> LOCATION: (410)..(415)
<223> OTHER INFORMATION: Xaa can be any naturally occurring amino acid
<220> FEATURE:
<221> NAME/KEY: misc_feature
<222> LOCATION: (421)..(423)
<223> OTHER INFORMATION: Xaa can be any naturally occurring amino acid
<220> FEATURE:
<221> NAME/KEY: misc_feature
<222> LOCATION: (425)..(429)
<223> OTHER INFORMATION: Xaa can be any naturally occurring amino acid
<220> FEATURE:
<221> NAME/KEY: misc_feature
<222> LOCATION: (431)..(434)
<223> OTHER INFORMATION: Xaa can be any naturally occurring amino acid
<220> FEATURE:
<221> NAME/KEY: misc_feature
<222> LOCATION: (436)..(436)
<223> OTHER INFORMATION: Xaa can be any naturally occurring amino acid
<220> FEATURE:
<221> NAME/KEY: misc_feature
<222> LOCATION: (439)..(439)
<223> OTHER INFORMATION: Xaa can be any naturally occurring amino acid
<220> FEATURE:
<221> NAME/KEY: misc_feature
<222> LOCATION: (441)..(441)
<223> OTHER INFORMATION: Xaa can be any naturally occurring amino acid
<220> FEATURE:
<221> NAME/KEY: misc_feature
<222> LOCATION: (443)..(443)
<223> OTHER INFORMATION: Xaa can be any naturally occurring amino acid
<220> FEATURE:
<221> NAME/KEY: misc_feature
<222> LOCATION: (449)..(451)
<223> OTHER INFORMATION: Xaa can be any naturally occurring amino acid
<220> FEATURE:
<221> NAME/KEY: misc_feature
<222> LOCATION: (456)..(456)
<223> OTHER INFORMATION: Xaa can be any naturally occurring amino acid
<220> FEATURE:
<221> NAME/KEY: misc_feature
<222> LOCATION: (460)..(460)
<223> OTHER INFORMATION: Xaa can be any naturally occurring amino acid
<220> FEATURE:
<221> NAME/KEY: misc_feature
<222> LOCATION: (465)..(465)
<223> OTHER INFORMATION: Xaa can be any naturally occurring amino acid
<220> FEATURE:
<221> NAME/KEY: misc_feature
<222> LOCATION: (467)..(472)
<223> OTHER INFORMATION: Xaa can be any naturally occurring amino acid

<400> SEQUENCE: 36

```
Met Ala Arg Leu Arg Xaa Arg Arg Pro Arg Gly Arg Phe Xaa Xaa Xaa
1               5                   10                  15

Xaa Arg Gly Arg Trp His Xaa Xaa Xaa Arg Leu Arg Arg Arg Xaa Tyr
            20                  25                  30

Ser Arg Arg Gly Lys Phe Arg Xaa Xaa Arg Arg Xaa Xaa Xaa Xaa Arg
```

```
        35                  40                  45

Arg Xaa Xaa Arg Xaa Xaa Phe His Asn Pro Xaa Pro Gly Xaa Tyr Xaa
    50                  55                  60

Val Arg Leu Pro Asn Pro Xaa Xaa Xaa Xaa Thr Xaa Xaa Phe Gln Gly
65                  70                  75                  80

Ile Xaa Phe Xaa Xaa Glu Xaa Xaa Xaa Xaa Xaa Lys Xaa Xaa Xaa Xaa
                85                  90                  95

Gly Gly Tyr Xaa Xaa Xaa Leu Xaa Xaa Xaa Xaa Val Ala Xaa Ile Xaa
            100                 105                 110

Val Asn Leu Xaa Glu Phe Xaa Leu Ala Xaa Met Xaa Leu Xaa Xaa Xaa
        115                 120                 125

Ser Lys Ile Gly Gly Pro Xaa Xaa Xaa Xaa Xaa Xaa Xaa Xaa Gly Xaa
    130                 135                 140

Gln Trp Ser Xaa Gln Xaa Xaa Gln Xaa Ala Trp Pro Xaa Xaa Xaa Xaa
145                 150                 155                 160

Xaa Xaa Xaa Xaa Xaa Xaa Pro Ser Xaa Xaa Pro Ser Xaa Trp Trp Arg
                165                 170                 175

Trp Ala Leu Xaa Xaa Met Xaa Pro Xaa Xaa Xaa Xaa Arg Phe Xaa Asn
            180                 185                 190

Xaa Pro Lys Xaa Met Thr Leu Xaa Xaa Met Gly Xaa Xaa Xaa Gly Gly
        195                 200                 205

Trp Xaa Leu Phe Arg His Xaa Xaa Thr Xaa Phe Xaa Xaa Leu Ala Thr
    210                 215                 220

Xaa Xaa Xaa Gly Xaa Phe Ser Pro Val Ala Ser Leu Leu Xaa Gln Xaa
225                 230                 235                 240

Xaa Tyr Xaa Xaa Arg Arg Xaa Leu Glu Gly Phe Xaa Val Lys Xaa Xaa
                245                 250                 255

Xaa Xaa Xaa Xaa Xaa Xaa Xaa Arg Lys Xaa Xaa Gln Pro Met Xaa Gly
            260                 265                 270

Xaa Xaa Xaa Tyr Ala Thr Xaa Xaa Xaa Xaa Xaa Asp Glu Gln Xaa Xaa
        275                 280                 285

Pro Xaa Xaa Pro Pro Asp Pro Pro Xaa Xaa Pro Asn Gln Gly Gly Cys
    290                 295                 300

Xaa Xaa Xaa Xaa Ala Xaa Gly Xaa Xaa Arg Leu Xaa Xaa Xaa Xaa Xaa
305                 310                 315                 320

Ser Xaa Xaa Xaa Xaa Xaa Ser Xaa Xaa Xaa Xaa Xaa Ser Phe Ala Xaa
                325                 330                 335

Leu Xaa Ala Xaa Gly Ala Xaa Trp Ser Phe Pro Xaa Xaa Gln Xaa Xaa
            340                 345                 350

Xaa Xaa Arg Xaa Ser Phe Asn Xaa His Xaa Xaa Xaa Gly Xaa Gly Asp
        355                 360                 365

Pro Xaa Gly Xaa Arg Trp Xaa Thr Leu Val Pro Xaa Gly Xaa Glu Xaa
    370                 375                 380

Ile Thr Asp Xaa Xaa Met Xaa Xaa Pro Ala Xaa Xaa Leu Asp Thr Xaa
385                 390                 395                 400

Xaa Xaa Thr Leu Xaa Xaa Ala Gln Gly Xaa Xaa Xaa Xaa Xaa Xaa Tyr
                405                 410                 415

Lys Phe Gly Thr Xaa Xaa Xaa Ala Xaa Xaa Xaa Xaa Xaa Met Xaa Xaa
            420                 425                 430

Xaa Xaa Trp Xaa Val Val Xaa Val Xaa Ser Xaa Trp Gln Leu Gly Asn
        435                 440                 445

Xaa Xaa Xaa Pro Tyr Pro Trp Xaa Val Asn Trp Xaa Asn Glu His Thr
    450                 455                 460
```

Xaa Thr Xaa Xaa Xaa Xaa Xaa Xaa Pro Val Asn Lys
465 470 475

<210> SEQ ID NO 37
<211> LENGTH: 2375
<212> TYPE: DNA
<213> ORGANISM: Artificial Sequence
<220> FEATURE:
<223> OTHER INFORMATION: HGYV genome

<400> SEQUENCE: 37
cggcgcgcgc ggcagcagcc tgtacacaga gacgtcgctc gggtcctccg gaccctcgct 60
cctcaacctt ttcttattaa aatcatcacc cagcgcgaca aacgccacaa ggcgtggtaa 120
ccaacgatat gtaagtaaac tgagactcat accggtacag gggggtacgt caccatgtac 180 agggggtac gtcaccatgt acagggggt acgtcatcat gtacaggggg gtacgtcacc 240
atgtacaggg gggtacgtca ccatgtacag gggggtacgt cacagccaat cagaattgag 300
cacgcccagg aacgcccctg ggcggggaga tgctatcaat ttagggatat aagcagagca 360
cataccggac ggcggtaggt atgtcatccg gcggtctcgg ggattgcagc gcctgtgaga 420
accgagccgc tgggggcagt gaattgccgc ttaggcaaga ggggcaactt gggcccagcg 480
gagccggatc cacgggcaag acactaaatg cagacccccc gctctcgccg acgagcaaca 540
actactcagt cagaactatt aacggcatac gagcatccaa caagttcgtc tccgccagca 600
gaaacgacct cgatagagat ccaaattggt atcgggtcaa ctataattac tctatcgcta 660
cctggctacg ccagtgtgcg cgttctcacg acgagatctg cacctgcgga cgatggagga 720
gtcactggtt ccaggaggct agtggacttg tcacacagga gacccagacg gaccagctcg 780
ccagagatct acgtcggctt cgccgcaaag gagaagcagc aaaaagaaaa cttgattacc 840
ttaagggaaa acggaccccc tataaaaaag ctaagactgt aacatggcaa gactacgaag 900
aagacgacct cgcggacgct ttggcttcta ccacagagga cgatggcact ggagacacag 960
actgcgacga agacgctatt cccggagggg taaatttcga tatgcgcgta gaagatcctt 1020
tgatcgccgc gttaagagga ggatcttcaa ccccacacccg ggctcctatg tggtaaggct 1080
accgaaccct tacaataagc ttaccctctt tttccaaggc attgtattca ttccggaggc 1140
tcaagctttt gttaaaagca cctataaaaa gactaacctt acggtttgcc atgtagcctc 1200
cataaatgtt aacctccgag aatttatgct tgcaacaatg cctttagatg caaagagcaa 1260
aatcggaggc cctaaccctt atcctcagca cttgcagggg tgccaatggt cagcacaaac 1320
gacgcaggac gcatggccgt acgcagcggg catgtcagaa acaaaaagac ccagcgtacc 1380
accgagtgag tggtggcgct gggctctcct ggtgatgcac cctagagcac ctggcagatt 1440
ttacaatgcc ccaaagctaa tgactctgga cgctatggga gacctgttag ggggctggca 1500
gctattcagg catgtaaaaa ccaagttcag agtgctagcg actatgggac aaggggcttt 1560
ctcaccagtt gcaagcctac ttgtacaaaa tgactactgg agcaggaggc acttagaggg 1620
cttcccagtt aaaggtgcac cacctatgtg caccatgcaa agaaaaactc agcagtacgg 1680
caacgtggag tccaatgcac cggcagatga gcaatggcta cccgtaaatc ccccagaccc 1740
accagtgtac ccaaaccagg gaggatgctc ccaaaacgtg gctccaggca tataccggct 1800
tgcaggctta gaagacagca gcagatgctt ttattcaaag gcttgtttcc ccagctttgc 1860
agcgctttct gctatgggtg caccctggtc atttcctagc actcaaaaac ctattcaaag 1920
aggctcattt aacaagcact ccatcacggg gacaggggac ccccagggcc gacggtggtt 1980

```
aacacttgtg cctaaaggag tcgagtggat tactgacgac accatggaac ctacgcaact   2040

ggacacagac attgcaacac tcttcttggc tcaaggcagt ccagtatggg caccctacaa   2100

attcggaact tttcacaaag cgatggcgct aacagcgatg cagaccaccc cttggtgcgt   2160

ggtgaaagtc cgttccatct ggcagctcgg caaccaaaga cagccgtacc catggcaagt   2220

gaactggtac aacgagcaca ctgcaacgga cagatacaac ccgtaattgg ggggggcttc   2280

gccctcccca aacccccccc cggggggggat cctccccccc ggaccccccg tcaataaata   2340

attaaataaa ccaaatcgaa ttatttattt atttt                              2375
```

<210> SEQ ID NO 38
<211> LENGTH: 1383
<212> TYPE: DNA
<213> ORGANISM: Artificial Sequence
<220> FEATURE:
<223> OTHER INFORMATION: H-VP1

<400> SEQUENCE: 38

```
atggcaagac tacgaagaag acgacctcgc ggacgctttg gcttctacca cagaggacga     60

tggcactgga gacacagact gcgacgaaga cgctattccc ggaggggtaa atttcgatat    120

gcgcgtagaa gatcctttga tcgccgcgtt aagaggagga tcttcaaccc acacccgggc    180

tcctatgtgg taaggctacc gaacccttac aataagctta ccctcttttt ccaaggcatt    240

gtattcattc cggaggctca agcttttgtt aaaagcacct ataaaaagac taaccttacg    300

gtttgccatg tagcctccat aaatgttaac ctccgagaat ttatgcttgc aacaatgcct    360

ttagatgcaa agagcaaaat cggaggccct aacccttatc ctcagcactt gcaggggtgc    420

caatggtcag cacaaacgac gcaggacgca tggccgtacg cagcgggcat gtcagaaaca    480

aaaagaccca gcgtaccacc gagtgagtgg tggcgctggg ctctcctggt gatgcaccct    540

agagcacctg gcagatttta caatgcccca aagctaatga ctctggacgc tatgggagac    600

ctgttagggg gctggcagct attcaggcat gtaaaaacca agttcagagt gctagcgact    660

atgggacaag ggggctttctc accagttgca agcctacttg tacaaaatga ctactggagc    720

aggaggcact tagagggctt cccagttaaa ggtgcaccac ctatgtgcac catgcaaaga    780

aaaactcagc agtacggcaa cgtggagtcc aatgcaccgg cagatgagca atggctaccc    840

gtaaatcccc cagacccacc agtgtaccca aaccagggag gatgctccca aaacgtggct    900

ccaggcatat accggcttgc aggcttagaa gacagcagca gatgctttta ttcaaaggct    960

tgtttcccca gctttgcagc gctttctgct atgggtgcac cctggtcatt tcctagcact   1020

caaaaaccta ttcaaagagg ctcatttaac aagcactcca tcacggggac aggggacccc   1080

cagggccgac ggtggttaac acttgtgcct aaaggagtcg agtggattac tgacgacacc   1140

atggaaccta cgcaactgga cacagacatt gcaacactct tcttggctca aggcagtcca   1200

gtatgggcac cctacaaatt cggaactttt cacaaagcga tggcgctaac agcgatgcag   1260

accacccctt ggtgcgtggt gaaagtccgt tccatctggc agctcggcaa ccaaagacag   1320

ccgtacccat ggcaagtgaa ctggtacaac gagcacactg caacggacag atacaacccg   1380

taa                                                                 1383
```

<210> SEQ ID NO 39
<211> LENGTH: 460
<212> TYPE: PRT
<213> ORGANISM: Artificial Sequence
<220> FEATURE:

-continued

<223> OTHER INFORMATION: H-VP1

<400> SEQUENCE: 39

```
Met Ala Arg Leu Arg Arg Arg Arg Pro Arg Gly Arg Phe Gly Phe Tyr
1               5                   10                  15

His Arg Gly Arg Trp His Trp Arg His Arg Leu Arg Arg Arg Arg Tyr
            20                  25                  30

Ser Arg Arg Gly Lys Phe Arg Tyr Ala Arg Arg Arg Ser Phe Asp Arg
        35                  40                  45

Arg Val Lys Arg Arg Ile Phe Asn Pro His Pro Gly Ser Tyr Val Val
    50                  55                  60

Arg Leu Pro Asn Pro Tyr Asn Lys Leu Thr Leu Phe Phe Gln Gly Ile
65                  70                  75                  80

Val Phe Ile Pro Glu Ala Gln Ala Phe Val Lys Ser Thr Tyr Lys Lys
                85                  90                  95

Thr Asn Leu Thr Val Cys His Val Ala Ser Ile Asn Val Asn Leu Arg
            100                 105                 110

Glu Phe Met Leu Ala Thr Met Pro Leu Asp Ala Lys Ser Lys Ile Gly
        115                 120                 125

Gly Pro Asn Pro Tyr Pro Gln His Leu Gln Gly Cys Gln Trp Ser Ala
    130                 135                 140

Gln Thr Thr Gln Asp Ala Trp Pro Tyr Ala Ala Gly Met Ser Glu Thr
145                 150                 155                 160

Lys Arg Pro Ser Val Pro Pro Ser Glu Trp Trp Arg Trp Ala Leu Leu
                165                 170                 175

Val Met His Pro Arg Ala Pro Gly Arg Phe Tyr Asn Ala Pro Lys Leu
            180                 185                 190

Met Thr Leu Asp Ala Met Gly Asp Leu Leu Gly Gly Trp Gln Leu Phe
        195                 200                 205

Arg His Val Lys Thr Lys Phe Arg Val Leu Ala Thr Met Gly Gln Gly
    210                 215                 220

Ala Phe Ser Pro Val Ala Ser Leu Leu Val Gln Asn Asp Tyr Trp Ser
225                 230                 235                 240

Arg Arg His Leu Glu Gly Phe Pro Val Lys Gly Ala Pro Pro Met Cys
                245                 250                 255

Thr Met Gln Arg Lys Thr Gln Gln Tyr Gly Asn Val Glu Ser Asn Ala
            260                 265                 270

Pro Ala Asp Glu Gln Trp Leu Pro Val Asn Pro Pro Asp Pro Pro Val
        275                 280                 285

Tyr Pro Asn Gln Gly Gly Cys Ser Gln Asn Val Ala Pro Gly Ile Tyr
    290                 295                 300

Arg Leu Ala Gly Leu Glu Asp Ser Ser Arg Cys Phe Tyr Ser Lys Ala
305                 310                 315                 320

Cys Phe Pro Ser Phe Ala Ala Leu Ser Ala Met Gly Ala Pro Trp Ser
                325                 330                 335

Phe Pro Ser Thr Gln Lys Pro Ile Gln Arg Gly Ser Phe Asn Lys His
            340                 345                 350

Ser Ile Thr Gly Thr Gly Asp Pro Gln Gly Arg Arg Trp Leu Thr Leu
        355                 360                 365

Val Pro Lys Gly Val Glu Trp Ile Thr Asp Asp Thr Met Glu Pro Thr
    370                 375                 380

Gln Leu Asp Thr Asp Ile Ala Thr Leu Phe Leu Ala Gln Gly Ser Pro
385                 390                 395                 400
```

-continued

```
Val Trp Ala Pro Tyr Lys Phe Gly Thr Phe His Lys Ala Met Ala Leu
                405                 410                 415

Thr Ala Met Gln Thr Thr Pro Trp Cys Val Val Lys Val Arg Ser Ile
            420                 425                 430

Trp Gln Leu Gly Asn Gln Arg Gln Pro Tyr Pro Trp Gln Val Asn Trp
        435                 440                 445

Tyr Asn Glu His Thr Ala Thr Asp Arg Tyr Asn Pro
    450                 455                 460


<210> SEQ ID NO 40
<211> LENGTH: 11
<212> TYPE: PRT
<213> ORGANISM: Artificial Sequence
<220> FEATURE:
<223> OTHER INFORMATION: Tat (47-57)

<400> SEQUENCE: 40

Tyr Gly Arg Lys Lys Arg Arg Gln Arg Arg Arg
1               5                   10


<210> SEQ ID NO 41
<211> LENGTH: 17
<212> TYPE: PRT
<213> ORGANISM: Artificial Sequence
<220> FEATURE:
<223> OTHER INFORMATION: Rev-(34-50)

<400> SEQUENCE: 41

Thr Arg Gln Ala Arg Arg Asn Arg Arg Arg Arg Trp Arg Glu Arg Gln
1               5                   10                  15

Arg


<210> SEQ ID NO 42
<211> LENGTH: 16
<212> TYPE: PRT
<213> ORGANISM: Artificial Sequence
<220> FEATURE:
<223> OTHER INFORMATION: Antp-(43-58)

<400> SEQUENCE: 42

Arg Gln Ile Lys Ile Tyr Phe Gln Asn Arg Arg Met Lys Trp Lys Lys
1               5                   10                  15


<210> SEQ ID NO 43
<211> LENGTH: 15
<212> TYPE: PRT
<213> ORGANISM: Artificial Sequence
<220> FEATURE:
<223> OTHER INFORMATION: flock house virus (FHV) coat-(35-49)

<400> SEQUENCE: 43

Arg Arg Arg Arg Asn Arg Thr Arg Arg Asn Arg Arg Arg Val Arg
1               5                   10                  15


<210> SEQ ID NO 44
<211> LENGTH: 18
<212> TYPE: PRT
<213> ORGANISM: Artificial Sequence
<220> FEATURE:
<223> OTHER INFORMATION: MAP

<400> SEQUENCE: 44

Lys Leu Ala Leu Lys Leu Ala Leu Lys Ala Leu Lys Ala Ala Leu Lys
1               5                   10                  15
```

Leu Ala

<210> SEQ ID NO 45
<211> LENGTH: 27
<212> TYPE: PRT
<213> ORGANISM: Artificial Sequence
<220> FEATURE:
<223> OTHER INFORMATION: transportan

<400> SEQUENCE: 45

Gly Trp Thr Leu Asn Ser Ala Gly Tyr Leu Leu Gly Lys Ile Asn Leu
1 5 10 15

Lys Ala Leu Ala Ala Leu Ala Lys Lys Ile Leu
20 25

<210> SEQ ID NO 46
<211> LENGTH: 16
<212> TYPE: PRT
<213> ORGANISM: Artificial Sequence
<220> FEATURE:
<223> OTHER INFORMATION: plsl

<400> SEQUENCE: 46

Arg Val Ile Arg Val Trp Phe Gln Asn Lys Arg Cys Lys Asp Lys Lys
1 5 10 15

<210> SEQ ID NO 47
<211> LENGTH: 21
<212> TYPE: PRT
<213> ORGANISM: Artificial Sequence
<220> FEATURE:
<223> OTHER INFORMATION: Pep-1

<400> SEQUENCE: 47

Lys Glu Thr Trp Trp Glu Thr Trp Trp Thr Glu Trp Ser Gln Pro Lys
1 5 10 15

Lys Lys Arg Arg Val
20

<210> SEQ ID NO 48
<211> LENGTH: 11
<212> TYPE: PRT
<213> ORGANISM: Artificial Sequence
<220> FEATURE:
<223> OTHER INFORMATION: PTD4

<400> SEQUENCE: 48

Tyr Ala Arg Ala Ala Ala Arg Gln Ala Arg Ala
1 5 10

<210> SEQ ID NO 49
<211> LENGTH: 10
<212> TYPE: PRT
<213> ORGANISM: Artificial Sequence
<220> FEATURE:
<223> OTHER INFORMATION: PTD

<400> SEQUENCE: 49

Ala Arg Ala Ala Ala Ala Gln Ala Arg Ala
1 5 10

<210> SEQ ID NO 50
<211> LENGTH: 6
<212> TYPE: PRT
<213> ORGANISM: Artificial Sequence
<220> FEATURE:

<223> OTHER INFORMATION: Linker

<400> SEQUENCE: 50

Gly Gly Ser Gly Gly Ser
1 5

<210> SEQ ID NO 51
<211> LENGTH: 21
<212> TYPE: DNA
<213> ORGANISM: Artificial Sequence
<220> FEATURE:
<223> OTHER INFORMATION: Primer HGyV.12F

<400> SEQUENCE: 51
gaaagcgctg caaagctggg g 21

<210> SEQ ID NO 52
<211> LENGTH: 21
<212> TYPE: DNA
<213> ORGANISM: Artificial Sequence
<220> FEATURE:
<223> OTHER INFORMATION: Primer HGyV.12R

<400> SEQUENCE: 52
tgcagcgctt tctgctatgg g 21

<210> SEQ ID NO 53
<211> LENGTH: 22
<212> TYPE: DNA
<213> ORGANISM: Artificial Sequence
<220> FEATURE:
<223> OTHER INFORMATION: Primer HGyV-VP1-F2q

<400> SEQUENCE: 53
tgcttgcaac aatgccttta ga 22

<210> SEQ ID NO 54
<211> LENGTH: 21
<212> TYPE: DNA
<213> ORGANISM: Artificial Sequence
<220> FEATURE:
<223> OTHER INFORMATION: Primer HGyV-VP1-R2q

<400> SEQUENCE: 54
cgctgggtct ttttgtttct g 21

<210> SEQ ID NO 55
<211> LENGTH: 20
<212> TYPE: DNA
<213> ORGANISM: Artificial Sequence
<220> FEATURE:
<223> OTHER INFORMATION: Primer HGyV-VP2-F3q

<400> SEQUENCE: 55
ggcatacgag catccaacaa 20

<210> SEQ ID NO 56
<211> LENGTH: 18
<212> TYPE: DNA
<213> ORGANISM: Artificial Sequence
<220> FEATURE:
<223> OTHER INFORMATION: Primer HGyV-VP2-R3q

<400> SEQUENCE: 56
tcgtccgcag gtgcagat 18

<210> SEQ ID NO 57
<211> LENGTH: 429
<212> TYPE: DNA
<213> ORGANISM: Artificial Sequence
<220> FEATURE:
<223> OTHER INFORMATION: PTD4-HuAP

<400> SEQUENCE: 57
gctagcgcac gcgcagcagc agcacaggca agagccggtg gtagcggtgg ttcaacaccg 60
cgtagccgtc gtcgtgcaac caccacccag agcgaactgc tgaccgcata tgaacatccg 120
accagcagca gccctccggc agaaaccacc agtattgaaa ttcagattgg tattggcagc 180
accattatta ccctgagcct gcctggttat gcaagcgttc gtgttctgac cacccgtagc 240
gcaccggcag atgatggtgg tgttaccggt agtcgtcgtc tggttgatct gagccatcgt 300
cgtccgcgtc gtaccagcag tccggaaatt tatgttggtt ttgcagccaa agagaaacag 360
cagaaagaaa atctgattac cctgcgtgaa aatggtccgc ctatcaaaaa actgcgtctg 420
taaggatcc 429

<210> SEQ ID NO 58
<211> LENGTH: 138
<212> TYPE: PRT
<213> ORGANISM: Artificial Sequence
<220> FEATURE:
<223> OTHER INFORMATION: PTD GGSGGS-H-apoptin

<400> SEQUENCE: 58

Ala Arg Ala Ala Ala Ala Gln Ala Arg Ala Gly Gly Ser Gly Gly Ser
1 5 10 15

Thr Pro Arg Ser Arg Arg Arg Ala Thr Thr Thr Gln Ser Glu Leu Leu
20 25 30

Thr Ala Tyr Glu His Pro Thr Ser Ser Ser Pro Pro Ala Glu Thr Thr
35 40 45

Ser Ile Glu Ile Gln Ile Gly Ile Gly Ser Thr Ile Ile Thr Leu Ser
50 55 60

Leu Pro Gly Tyr Ala Ser Val Arg Val Leu Thr Thr Arg Ser Ala Pro
65 70 75 80

Ala Asp Asp Gly Gly Val Thr Gly Ser Arg Arg Leu Val Asp Leu Ser
85 90 95

His Arg Arg Pro Arg Arg Thr Ser Ser Pro Glu Ile Tyr Val Gly Phe
100 105 110

Ala Ala Lys Glu Lys Gln Gln Lys Glu Asn Leu Ile Thr Leu Arg Glu
115 120 125

Asn Gly Pro Pro Ile Lys Lys Leu Arg Leu
130 135

<210> SEQ ID NO 59
<211> LENGTH: 423
<212> TYPE: DNA
<213> ORGANISM: Artificial Sequence
<220> FEATURE:
<223> OTHER INFORMATION: PTD4-AvAP

<400> SEQUENCE: 59
gctagcgcac gcgcagcagc agcacaggca agagccggtg gtagcggtgg ttcaaatgca 60
ctgcaagaag atacccctcc gggtccgagc accgtttttc gtccgcctac cagcagccgt 120
ccgctggaaa caccgcattg tcgtgaaatt cgtattggta ttgcaggcat taccattacc 180

-continued

```
ctgagcctgt gtggttgtgc aaatgcacgt gcaccgaccc tgcgtagcgc aaccgcagat    240

aatagcgaaa gcaccggctt taaaaacgtt ccggatctgc gtaccgatca gccgaaaccg    300

cctagcaaaa aacgtagctg tgatccgagc gaatatcgtg ttagcgaact gaaagaaagc    360

ctgattacca ccaccccgag tcgtccgcgt accgcacgtc gttgtattcg tctgtaagga    420

tcc                                                                   423


<210> SEQ ID NO 60
<211> LENGTH: 136
<212> TYPE: PRT
<213> ORGANISM: Artificial Sequence
<220> FEATURE:
<223> OTHER INFORMATION: PTD- GGSGGS-A-apoptin

<400> SEQUENCE: 60

Ala Arg Ala Ala Ala Ala Gln Ala Arg Ala Gly Gly Ser Gly Gly Ser
1               5                   10                  15

Asn Ala Leu Gln Glu Asp Thr Pro Pro Gly Pro Ser Thr Val Phe Arg
            20                  25                  30

Pro Pro Thr Ser Ser Arg Pro Leu Glu Thr Pro His Cys Arg Glu Ile
        35                  40                  45

Arg Ile Gly Ile Ala Gly Ile Thr Ile Thr Leu Ser Leu Cys Gly Cys
    50                  55                  60

Ala Asn Ala Arg Ala Pro Thr Leu Arg Ser Ala Thr Ala Asp Asn Ser
65                  70                  75                  80

Glu Ser Thr Gly Phe Lys Asn Val Pro Asp Leu Arg Thr Asp Gln Pro
                85                  90                  95

Lys Pro Pro Ser Lys Lys Arg Ser Cys Asp Pro Ser Glu Tyr Arg Val
            100                 105                 110

Ser Glu Leu Lys Glu Ser Leu Ile Thr Thr Thr Pro Ser Arg Pro Arg
        115                 120                 125

Thr Ala Arg Arg Cys Ile Arg Leu
    130                 135
```